US008053197B2

(12) United States Patent
Vandenbark et al.

(10) Patent No.: US 8,053,197 B2
(45) Date of Patent: Nov. 8, 2011

(54) METHODS FOR DETECTING AND TREATING AUTOIMMUNE DISORDERS

(75) Inventors: Arthur A. Vandenbark, Portland, OR (US); Halina Offner, Portland, OR (US); Richard Bartholomew, San Diego, CA (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 702 days.

(21) Appl. No.: 11/658,834

(22) PCT Filed: Jul. 29, 2005

(86) PCT No.: PCT/US2005/026915
§ 371 (c)(1),
(2), (4) Date: Aug. 20, 2008

(87) PCT Pub. No.: WO2006/012641
PCT Pub. Date: Feb. 2, 2006

(65) Prior Publication Data
US 2009/0010885 A1 Jan. 8, 2009

Related U.S. Application Data

(60) Provisional application No. 60/592,431, filed on Jul. 30, 2004, provisional application No. 60/667,820, filed on Apr. 1, 2005.

(51) Int. Cl.
*G01N 33/53* (2006.01)
(52) U.S. Cl. .................................. 435/7.1; 435/7.24
(58) Field of Classification Search .................. None
See application file for complete search history.

(56) References Cited

U.S. PATENT DOCUMENTS

| | | | |
|---|---|---|---|
| 5,194,425 A | 3/1993 | Sharma et al. | |
| 5,223,426 A | 6/1993 | Skibbens et al. | |
| 5,569,585 A | 10/1996 | Goodwin et al. | |
| 5,612,035 A | 3/1997 | Howell et al. | |
| 5,614,192 A | 3/1997 | Vandenbark | |
| 5,776,459 A | 7/1998 | Vandenbark | |
| 5,837,246 A | 11/1998 | Howell et al. | |
| 5,856,446 A | 1/1999 | Weiner et al. | |
| 5,858,968 A | 1/1999 | Weiner et al. | |
| 5,869,093 A | 2/1999 | Weiner et al. | |
| 5,939,281 A | 8/1999 | Lehmann et al. | |
| 5,939,400 A | 8/1999 | Steinman et al. | |
| 6,019,971 A | 2/2000 | Weiner et al. | |
| 6,039,947 A | 3/2000 | Weiner et al. | |
| 6,045,796 A | 4/2000 | Sriram et al. | |
| 6,090,387 A | 7/2000 | Howell et al. | |
| 6,113,903 A | 9/2000 | Albertini et al. | |
| 6,159,470 A | 12/2000 | Howell et al. | |
| 6,197,926 B1 | 3/2001 | Gaur et al. | |
| 6,207,645 B1 | 3/2001 | Howell et al. | |
| 6,218,132 B1 | 4/2001 | Spack et al. | |
| 6,221,352 B1 | 4/2001 | Howell et al. | |
| 6,958,327 B1 | 10/2005 | Hillisch et al. | |
| 2002/0183299 A1 | 12/2002 | Voskuhl | |
| 2003/0170648 A1 | 9/2003 | Khattri et al. | |
| 2003/0190665 A1 | 10/2003 | Vandenbark | |
| 2005/0032725 A1* | 2/2005 | Rao et al. | 514/44 |
| 2005/0186207 A1* | 8/2005 | Bluestone et al. | 424/144.1 |
| 2006/0115899 A1* | 6/2006 | Buckner et al. | 435/372 |

FOREIGN PATENT DOCUMENTS

| | | |
|---|---|---|
| EP | 0 159 739 A1 | 10/1985 |
| EP | 10175854 | 6/1998 |
| EP | 957359 | 11/1999 |
| JP | 101175854 | 6/1998 |
| WO | WO 94/25063 | 11/1994 |
| WO | WO 99/58977 | 11/1999 |
| WO | WO 01/32680 A2 | 5/2001 |
| WO | WO 02/090600 | 11/2002 |

OTHER PUBLICATIONS

Yagi et al., International Immunology, vol. 16, No. 11, pp. 1643-1656.*
Buckner et al., Arthritis Res Ther. 2004;6(5):215-22. Epub Aug. 11, 2004.*
Gronski, "Novel Insights in the Regulation of the Immune System: A Report on the FASEB Summer Research Conference on Autoimmunity," *RDS, The Review of Diabetic Studies*, pp. 47-50, (Jun. 2003).
Notification of Transmittal of the International Search Report and The Written Opinion for PCT Application No. PCT/US05/26915 (dated Oct. 10, 2007).
Acha-Orbea et al., Limited Heterogeneity of Cell Receptors from Lymphocytes Mediating Autoimmune Encephalomyelitis Allows Specific Immune Intervention, *Cell* 54:263-273 (1988).
Arden et al., "Human T-cell receptor variable gene segment families," *Immunogenetics* 42:455-500 (1995).
Bebo et al., "Androgens Alter the Cytokine Profile and Reduce Encephalitogenicity of Myelin-reactive T-Cells," *J. Immunol.* 162:35 (1998).
Bebo et al., "Gender Differences in Experimental Autoimmune Encephalomyelitis Develop During the Induction of the Immune response to Encephalitogenic Peptides," *J. Neurosci. Res.* 52:420-429 (1998).
Bourdette et al., "Basic Protein-Specific T-Cell Lines That Induce Experimental Autoimmune Encephalomyelitis in SJL/J Mice: Comparison with Lewis Rat Lines," *Cell Immunol.* 112:351 (1988).
Bourdette et al., "A highly immunogenic trivalent T cell receptor peptide vaccine for multiple sclerosis," *Multiple Sclerosis* 11:1-10 (2005).

(Continued)

*Primary Examiner* — Zachary Skelding
(74) *Attorney, Agent, or Firm* — Klarquist Sparkman, LLP

(57) ABSTRACT

The present disclosure relates to methods for inhibiting an autoimmune disease by administering to a subject a therapeutically effective amount of a composition that increases FOXP3 expression, thereby inhibiting the autoimmune disease. Further disclosed herein are methods for detecting in a subject an autoimmune disease or a predisposition to an autoimmune disease, and methods for assessing the efficacy of a therapy for an autoimmune disease.

12 Claims, 15 Drawing Sheets

OTHER PUBLICATIONS

Brosterhus et al., "Enrichment and detection of live antigen-specific CD4+ T cells based on cytokine secretion," *Eur. J. Immunol.* 29:4053-4059 (1999).

Carlsten et al., "Additive effects of suboptimal doses of estrogen and cortisone on the suppression of T lymphocyte dependent inflammatory responses in mice," *Infamm Res.* 45:26-30 (1996).

Correale et al., "Steroid Hormone Regulations of Cytokine Secretion by Proteolipid Protein-Specific CD4+ T Cells Clones Isolated from Multiple Sclerosis Patients and Normal Control Subjects," *J. Immunol.* 161:3365-3374 (1998).

Choi et al., "Interaction of *Staphylococcus aureus* toxin 'superantigens' with human T cells," *Proc. Natl. Acad. Sci. USA* 86:8941-8945 (1989).

Chou et al., "Immunity to TCR peptides in multiple sclerosis," *J. Immunol.* 152:2520-2529 (1994).

Chou et al., "MHC-restriction, cytokine profile, and immunoregulatory effects of human T cells specific for TCR Vβ CDR2 peptides: comparison with myelin basic protein-specific T cells," *J. Neuroscience Res.* 45:838-851 (1996).

Cochlovius et al., "In vitro and in vivo induction of a Th cell response toward peptides of the melanoma-associated glycoprotein 100 protein selected by the TEPITOPE program," *J. Immunol.* 165:4731-4741 (2000).

Concannon et al., "Diversity and structure of human T-cell receptor β-chain variable region genes," *Proc. Natl. Acad. Sci. USA* 83:6598-6602 (1986).

Dalton et al., "Multiple Defects of Immune Cell Function in Mice with Disrupted Interferon-γ Genes," *Science* 259:1739-1742 (1993).

Evavold et al., "Tickling the TCR: selective T-cell functions stimulated by altered peptide ligands," *Immunology Today* 14:602-609 (1993).

Fairchild, "Altered peptide ligands: prospects for immune intervention in autoimmune disease," *Eur. J. Immunogenet.* 24:155-167 (1997).

Genevee et al., "An experimentally validated panel of subfamily-specific oligonucleotide primer (Vα-w29/Vβ1-w24) for the study of human T cell receptor variable V gene segment usage by polymerase chain reaction," *Eur. J. Immunol.* 22:1261-1269 (1992).

Gilmore et al., "Effect of Estradiol on Cytokine Secretion by Proteolipid Protein-Specific T Cell Clones Isolated from Multiple Sclerosis Patients and Normal Control Subjects," *J. Immunol.* 158:446-451 (1997).

Goverman et al., "Transgenic Mice that Express a Myelin Basic Protein-Specific T Cell Receptor Develop Spontaneous Autoimmunity," *Cell* 72:551-560 (1993).

Hashim et al., Antibodies Specific for VB8 Receptor Peptide Suppress Experimental Autoimmune Encephalomyelitis, *J. Immunol.* 144:4621-4627 (1990).

Huan et al., "Decreased FOXP3 Levels in Multiple Sclerosis Patients," *J. Neuroscience Research* 81:45-52 (2005).

Jansson et al., "Estrogen induces a potent suppression of experimental autoimmune encephalomyelitis and collagen-induced arthritis in mice," *Journal of Neuroimmunology* 53:203-207 (1994).

Kimura et al., "Sequences and repertoire of the human T cell receptor α and β chain variable region genes in thymocytes," *Eur. J. Immunol.* 17:375-383 (1987).

Kumar et al., "The Involvement of T Cell Receptor Peptide-specific Regulatory CD4+ T Cells in Recovery from Antigen-induced Autoimmune Disease," *J. Exp. Med.* 178:909-916 (1993).

Mancia et al., "Characterization of the T-cell receptor V-β repertoire in Kawasaki disease," *Scand. J. Immunol.* 48:443-449 (1998).

Martin et al., "Immunotherapy of multiple sclerosis: Where are we? Where should we go?" *Nat. Immunol.* 2:785-788 (2001).

Offner et al., "Vaccination with BV8S2 Protein Amplifies TCR-Specific Regulation and Protection Against Experimental Autoimmune Encephalomyelitis in TCR BV8S2 Transgenic Mice," *J. Immunol.* 161:2178-2186 (1998).

Offner et al., "Estrogen potentiates treatment with T-cell receptor protein of female mice with experimental encephalomyelitis," *Journal of Clinical Investigation* 105(10):1465-1472 (2000).

Olsson et al., "Autoreactive T lymphocytes in multiple sclerosis determined by antigen-induced secretion of interferon-γ," *J. Clin. Invest.* 86:981-985 (1990).

Robinson, "The human T cell receptor β-chain gene complex contains at least 57 variable gene segments," *J. Immunol.* 146:4392-4397 (1991).

Roselli et al., "Sex Differences in Androgen Responsiveness in the Rat Brain: Regional Differences in the Induction of Aromatase Activity," *Endocrine* 64:139 (1996).

Rovaris et al, The role of non-conventional MR techniques to study multiple sclerosis patients, *J. Neurol. Sci.* 186 Suppl. 1:S3-9 (2001).

Savoie et al., "Use of Bonsai decision trees for the identification of potential MHC class I peptide epitope motifs," *Pac. Symp. Biocomput.* 1999:182-189 (1999).

Sicotte et al., "Treatment of Multiple Sclerosis with the Pregnancy Hormone Estriol," *Ann. Neurol* 52:421-428 (2002).

Steinman et al., "Virtues and pitfalls of EAE for the development of therapies for multiple sclerosis," *Trends in Immunology* 26:565-571 (2005).

Thornton and Shevach, "CD4+CD25+ Immunoregulatory T Cells Suppress Polyclonal T Cell Activation In Vitro by Inhibiting Interleukin 2 Production," *J. Experimental Medicine* 188(2):287-296 (1998).

Vandenbark et al., "Treatment of multiple sclerosis with T-cell receptor peptides: Results of a double-blind pilot trail," *Nature Med.* 2:1109-1115 (1996).

Vandenbark, "TCR Peptide Vaccination in Multiple Sclerosis: Boosting a Deficient Natural Regulatory Network that may Involve TCR-Specific CD4+CD25+ Treg Cells," *Current Drug Targets* 4:217-229 (2005).

Vaniene et al., "Neonatal Injection of Lewis Rats with Recombinant Vβ8.2 Induces T Cell but not B Cell Tolerance and Increased Severity of Experimental Autoimmune Encephalomyelitis," *J. Neurosci. Res.* 45:475-486 (1996).

Venken et al., "Secondary Progressive in Contrast to Relapsing-Remitting Multiple Sclerosis Patients Show a Normal CD4+CD25+ Regulatory T-Cell Function and FOXP3 Expression," *J. Neuroscience Research* 83:1432-1446 (2006).

WPI Database, Derwent Publications Ltd., London, GB, AN 1998-422294, XP0021 89653 and JP 10 175854A (Doctors Cosmetic YG) (1998) Abstract.

Zipp et al., "Diversity of the anti-T-cell receptor immune response and its implications for T-cell vaccination therapy of multiple sclerosis," *Brain* 121:1395-1407 (1998).

* cited by examiner

SEQUENCE LISTING

```
<160> NUMBER OF SEQ ID NOS: 120

<210> SEQ ID NO 1
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 1

Tyr Pro Gly Gln His Leu Gln Leu Leu Leu Lys Tyr Phe Ser Gly Asp
1               5                   10                  15

Pro Leu Val Lys Gly
            20

<210> SEQ ID NO 2
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 2

Tyr Pro Asn Gln Gly Leu Gln Leu Leu Leu Lys Tyr Thr Ser Ala Ala
1               5                   10                  15

Thr Leu Val Lys Gly
            20

<210> SEQ ID NO 3
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 3

Tyr Pro Asn Gln Gly Leu Gln Leu Leu Leu Lys Tyr Thr Thr Gly Ala
1               5                   10                  15
```

```
Thr Leu Val Lys Gly
        20

<210> SEQ ID NO 4
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 4

Tyr Pro Asn Gln Gly Leu Gln Leu Leu Leu Lys Tyr Thr Ser Ala Ala
1               5                   10                  15

Thr Leu Val Lys Gly
        20

<210> SEQ ID NO 5
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 5

Tyr Pro Asn Gln Gly Leu Gln Leu Leu Leu Lys Tyr Leu Ser Gly Ser
1               5                   10                  15

Thr Leu Val Glu Ser
        20

<210> SEQ ID NO 6
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 6

Tyr Pro Asn Gln Gly Leu Gln Leu Leu Leu Lys Tyr Leu Ser Gly Ser
1               5                   10                  15

Thr Leu Val Lys Gly
        20

<210> SEQ ID NO 7
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 7

Ser Pro Gly Gln Gly Leu Gln Leu Leu Leu Lys Tyr Phe Ser Gly Asp
1               5                   10                  15

Thr Leu Val Gln Gly
        20

<210> SEQ ID NO 8
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 8

His Pro Asn Lys Gly Leu Gln Leu Leu Leu Lys Tyr Thr Ser Ala Ala
1               5                   10                  15
```

Thr Leu Val Lys Gly
        20

<210> SEQ ID NO 9
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 9

Tyr Ser Gly Lys Ser Pro Glu Leu Ile Met Phe Ile Tyr Ser Asn Gly
1               5                   10                  15

Asp Lys Glu Asp Gly
        20

<210> SEQ ID NO 10
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 10

Tyr Ser Gly Lys Ser Pro Glu Leu Ile Met Ser Ile Tyr Ser Asn Gly
1               5                   10                  15

Asp Lys Glu Asp Gly
        20

<210> SEQ ID NO 11
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 11

Tyr Ser Arg Lys Gly Pro Glu Leu Leu Met Tyr Thr Tyr Ser Ser Gly
1               5                   10                  15

Asn Lys Glu Asp Gly
        20

<210> SEQ ID NO 12
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 12

Tyr Ser Arg Ile Gly Pro Glu Leu Leu Met Tyr Thr Tyr Ser Ser Gly
1               5                   10                  15

Asn Lys Glu Asp Gly
        20

<210> SEQ ID NO 13
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 13

Asp Cys Arg Lys Glu Pro Lys Leu Leu Met Ser Val Tyr Ser Ser Gly
1               5                   10                  15

Asn Glu Asp Gly Arg
            20

<210> SEQ ID NO 14
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 14

Asn Ser Gly Arg Gly Leu Val His Leu Ile Leu Ile Arg Ser Asn Glu
1               5                   10                  15

Arg Glu Lys His Ser
            20

<210> SEQ ID NO 15
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 15

Leu Pro Ser Gln Gly Pro Glu Tyr Val Ile His Gly Leu Thr Ser Asn
1               5                   10                  15

Val Asn Asn Arg Met
            20

<210> SEQ ID NO 16
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 16

Ile His Ser Gln Gly Pro Gln Tyr Ile Ile His Gly Leu Lys Asn Asn
1               5                   10                  15

Glu Thr Asn Glu Met
            20

<210> SEQ ID NO 17
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 17

Ile His Ser Gln Gly Pro Gln Asn Ile Ile His Gly Leu Lys Asn Asn
1               5                   10                  15

Glu Thr Asn Glu Met
            20

<210> SEQ ID NO 18
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 18

Asp Pro Gly Arg Gly Pro Val Phe Leu Leu Leu Ile Arg Glu Asn Glu
1               5                   10                  15

Lys Glu Lys Arg Lys
            20

<210> SEQ ID NO 19
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 19

Ser Ser Gly Glu Met Ile Phe Leu Ile Tyr Gln Gly Ser Tyr Asp Gln
1               5                   10                  15

Gln Asn Ala Thr Glu
            20

<210> SEQ ID NO 20
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 20

Ser Ser Gly Glu Met Ile Phe Leu Ile Tyr Gln Gly Ser Tyr Asp Glu
1               5                   10                  15

Gln Asn Ala Thr Glu
            20

<210> SEQ ID NO 21
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 21

His Asp Gly Gly Ala Pro Thr Phe Leu Ser Tyr Asn Ala Leu Asp Gly
1               5                   10                  15

Leu Glu Glu Thr Gly
            20

<210> SEQ ID NO 22
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 22

His Asp Gly Gly Ala Pro Thr Phe Leu Ser Tyr Asn Gly Leu Asp Gly
1               5                   10                  15

Leu Glu Glu Thr Gly
            20

<210> SEQ ID NO 23
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 23

His Ala Gly Glu Ala Pro Thr Phe Leu Ser Tyr Asn Val Leu Asp Gly
1               5                   10                  15

Leu Glu Glu Lys Gly
            20

<210> SEQ ID NO 24
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 24

Glu Leu Gly Lys Arg Pro Gln Leu Ile Ile Asp Ile Arg Ser Asn Val
1               5                   10                  15

Gly Glu Lys Lys Asp
            20

<210> SEQ ID NO 25
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 25

Glu Leu Gly Lys Gly Pro Gln Leu Ile Ile Asp Ile Arg Ser Asn Val
1               5                   10                  15

Gly Glu Lys Lys Asp
            20

<210> SEQ ID NO 26
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 26

Glu Ser Gly Lys Gly Pro Gln Phe Ile Ile Asp Ile Arg Ser Asn Met
1               5                   10                  15

Asp Lys Arg Gln Gly
            20

<210> SEQ ID NO 27
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 27

Tyr Ser Arg Gln Arg Leu Gln Leu Leu Leu Arg His Ile Ser Arg Glu
1               5                   10                  15

Ser Ile Lys Gly Phe
            20

<210> SEQ ID NO 28
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 28

Glu Pro Gly Glu Gly Pro Val Leu Leu Val Thr Val Val Thr Gly Gly
1               5                   10                  15

Glu Val Lys Lys Leu
            20

<210> SEQ ID NO 29
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 29

Phe Pro Gly Cys Ala Pro Arg Leu Leu Val Lys Gly Ser Lys Pro Ser
1               5                   10                  15

Gln Gln Gly Arg Tyr
            20

<210> SEQ ID NO 30
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 30

Pro Pro Ser Gly Glu Leu Val Phe Leu Ile Arg Arg Asn Ser Phe Asp
1               5                   10                  15

Glu Gln Asn Glu Ile
            20

<210> SEQ ID NO 31
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 31

Asn Pro Trp Gly Gln Leu Ile Asn Leu Phe Tyr Ile Pro Ser Gly Thr
1               5                   10                  15

Lys Gln Asn Gly Arg
            20

<210> SEQ ID NO 32
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 32

Pro Pro Ser Arg Gln Met Ile Leu Val Ile Arg Gln Glu Ala Tyr Lys
1               5                   10                  15

Gln Gln Asn Ala Thr
            20

<210> SEQ ID NO 33
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 33

Glu Pro Gly Ala Gly Leu Gln Leu Leu Thr Tyr Ile Phe Ser Asn Met
1               5                   10                  15

Asp Met Lys Gln Asp
            20

<210> SEQ ID NO 34
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 34

Tyr Pro Asn Arg Gly Leu Gln Phe Leu Leu Lys Tyr Ile Thr Gly Asp
1               5                   10                  15

Asn Leu Val Lys Gly
            20

<210> SEQ ID NO 35
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 35

Phe Pro Gly Lys Gly Pro Ala Leu Leu Ile Ala Ile Arg Pro Asp Val
1               5                   10                  15

Ser Glu Lys Lys Glu
            20

<210> SEQ ID NO 36
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 36

Glu Thr Ala Lys Thr Pro Glu Ala Leu Phe Val Met Thr Leu Asn Gly
1               5                   10                  15

Asp Glu Lys Lys Lys
            20

<210> SEQ ID NO 37
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 37

His Pro Gly Gly Gly Ile Val Ser Leu Phe Met Leu Ser Ser Gly Lys
1               5                   10                  15

Lys Lys His Gly Arg
            20

<210> SEQ ID NO 38
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 38

Phe Pro Ser Gln Gly Pro Arg Phe Ile Ile Gln Gly Tyr Lys Thr Lys
1               5                   10                  15

```
Val Thr Asn Glu Val
            20

<210> SEQ ID NO 39
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 39

Tyr Pro Ala Glu Gly Pro Thr Phe Leu Ile Ser Ile Ser Ser Ile Lys
1               5                   10                  15

Asp Lys Asn Glu Asp
            20

<210> SEQ ID NO 40
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 40

Tyr Pro Gly Glu Gly Leu Gln Leu Leu Leu Lys Ala Thr Lys Ala Asp
1               5                   10                  15

Asp Lys Gly Ser Asn
            20

<210> SEQ ID NO 41
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 41

Asp Pro Gly Lys Gly Leu Thr Ser Leu Leu Leu Ile Gln Ser Ser Gln
1               5                   10                  15

Arg Glu Gln Thr Ser
            20

<210> SEQ ID NO 42
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 42

Asp Thr Gly Arg Gly Pro Val Ser Leu Thr Ile Met Thr Phe Ser Glu
1               5                   10                  15

Asn Thr Lys Ser Asn
            20

<210> SEQ ID NO 43
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 43

Asp Pro Gly Glu Gly Pro Val Leu Leu Ile Ala Leu Tyr Lys Ala Gly
1               5                   10                  15
```

Glu Leu Thr Ser Asn
            20

<210> SEQ ID NO 44
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 44

Lys Tyr Gly Glu Gly Leu Ile Phe Leu Met Met Leu Gln Lys Gly Gly
1               5                   10                  15

Glu Glu Lys Ser His
            20

<210> SEQ ID NO 45
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 45

Asp Pro Gly Lys Ser Leu Glu Ser Leu Phe Val Leu Leu Ser Asn Gly
1               5                   10                  15

Ala Val Lys Gln Glu
            20

<210> SEQ ID NO 46
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 46

Gln Glu Lys Lys Ala Pro Thr Phe Leu Phe Met Leu Thr Ser Ser Gly
1               5                   10                  15

Ile Glu Lys Lys Ser
            20

<210> SEQ ID NO 47
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 47

Lys His Gly Glu Ala Pro Val Phe Leu Met Ile Leu Leu Lys Gly Gly
1               5                   10                  15

Glu Gln Met Arg Arg
            20

<210> SEQ ID NO 48
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 48

Lys His Gly Glu Ala Pro Val Phe Leu Met Ile Leu Leu Lys Gly Gly
1               5                   10                  15

```
Glu Gln Lys Gly His
            20

<210> SEQ ID NO 49
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 49

Asp Pro Gly Lys Gly Pro Glu Phe Leu Phe Thr Leu Tyr Ser Ala Gly
1               5                   10                  15

Glu Glu Lys Glu Lys
            20

<210> SEQ ID NO 50
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 50

Tyr Pro Ser Lys Pro Leu Gln Leu Leu Gln Arg Glu Thr Met Glu Asn
1               5                   10                  15

Ser Lys Asn Phe Gly
            20

<210> SEQ ID NO 51
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 51

Arg Pro Gly Gly His Pro Val Phe Leu Ile Gln Leu Val Lys Ser Gly
1               5                   10                  15

Glu Val Lys Lys Gln
            20

<210> SEQ ID NO 52
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 52

Ser Leu Asp Gln Gly Leu Gln Phe Leu Ile Gln Tyr Tyr Asn Gly Glu
1               5                   10                  15

Glu Arg Ala Lys Gly
            20

<210> SEQ ID NO 53
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 53

Ser Leu Asp Gln Gly Leu Gln Phe Leu Ile His Tyr Tyr Asn Gly Glu
1               5                   10                  15
```

Glu Arg Ala Lys Gly
            20

<210> SEQ ID NO 54
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 54

Phe Pro Lys Gln Ser Leu Met Leu Met Ala Thr Ser Asn Glu Gly Ser
1               5                   10                  15

Lys Ala Thr Tyr Glu
            20

<210> SEQ ID NO 55
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 55

Phe Pro Lys Lys Ser Leu Met Leu Met Ala Thr Ser Asn Glu Gly Ser
1               5                   10                  15

Lys Ala Thr Tyr Glu
            20

<210> SEQ ID NO 56
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 56

Phe Pro Lys Gln Ser Leu Met Leu Met Ala Thr Ser Asn Glu Gly Cys
1               5                   10                  15

Lys Ala Thr Tyr Glu
            20

<210> SEQ ID NO 57
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 57

Phe Pro Lys Lys Ser Leu Met Gln Ile Ala Thr Ser Asn Glu Gly Ser
1               5                   10                  15

Lys Ala Thr Tyr Glu
            20

<210> SEQ ID NO 58
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 58

Asp Pro Gly Leu Gly Leu Arg Leu Ile Tyr Phe Ser Tyr Asp Val Lys
1               5                   10                  15

Met Lys Glu Lys Gly
            20

<210> SEQ ID NO 59
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 59

Gln Pro Gly Gln Ser Leu Thr Leu Ile Ala Thr Ala Asn Gln Gly Ser
1               5                   10                  15

Glu Ala Thr Tyr Glu
            20

<210> SEQ ID NO 60
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 60

Thr Pro Gly Gln Gly Leu Gln Phe Leu Phe Glu Tyr Phe Ser Glu Thr
1               5                   10                  15

Gln Arg Asn Lys Gly
            20

<210> SEQ ID NO 61
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 61

Thr Leu Gly Gln Gly Leu Gln Phe Leu Phe Glu Tyr Phe Ser Glu Thr
1               5                   10                  15

Gln Arg Asn Lys Gly
            20

<210> SEQ ID NO 62
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 62

Ala Leu Gly Gln Gly Pro Gln Phe Ile Phe Gln Thr Tyr Glu Glu Glu
1               5                   10                  15

Glu Arg Gln Arg Gly
            20

<210> SEQ ID NO 63
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 63

Val Leu Gly Gln Gly Pro Gln Phe Ile Phe Gln Tyr Tyr Glu Lys Glu
1               5                   10                  15

```
Glu Arg Gly Arg Gly
            20

<210> SEQ ID NO 64
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 64

Ala Leu Gly Leu Gly Leu Gln Leu Leu Trp Tyr Asp Gly Glu
1               5                   10                  15

Glu Arg Asn Arg Gly
            20

<210> SEQ ID NO 65
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 65

Ala Leu Gly Leu Gly Leu Gln Phe Leu Leu Trp Tyr Asp Gly Glu
1               5                   10                  15

Glu Arg Asn Arg Gly
            20

<210> SEQ ID NO 66
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 66

Ala Leu Gly Gln Gly Pro Gln Phe Ile Phe Gln Tyr Tyr Arg Glu Glu
1               5                   10                  15

Glu Asn Gly Arg Gly
            20

<210> SEQ ID NO 67
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 67

Ser Leu Gly Gln Gly Pro Glu Phe Leu Ile Tyr Phe Gln Gly Thr Gly
1               5                   10                  15

Ala Ala Asp Asp Ser
            20

<210> SEQ ID NO 68
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 68

Ser Leu Gly Gln Gly Pro Glu Leu Leu Ile Tyr Phe Gln Gly Thr Gly
1               5                   10                  15
```

Ala Ala Asp Asp Ser
            20

<210> SEQ ID NO 69
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 69

Ala Leu Gly Gln Gly Pro Glu Phe Leu Thr Tyr Phe Gln Asn Glu Ala
1               5                   10                  15

Gln Leu Asp Lys Ser
            20

<210> SEQ ID NO 70
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 70

Ala Leu Gly Gln Gly Pro Glu Phe Leu Thr Tyr Phe Asn Tyr Glu Ala
1               5                   10                  15

Gln Gln Asp Lys Ser
            20

<210> SEQ ID NO 71
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 71

Thr Leu Gly Gln Gly Pro Glu Phe Leu Thr Tyr Phe Gln Asn Glu Ala
1               5                   10                  15

Gln Leu Glu Lys Ser
            20

<210> SEQ ID NO 72
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 72

Asn Pro Gly Gln Gly Pro Glu Phe Leu Thr Tyr Phe Gln Asn Glu Ala
1               5                   10                  15

Gln Leu Glu Lys Ser
            20

<210> SEQ ID NO 73
<211> LENGTH: 20
<212> TYPE: PRT
<213> ORGANISM: Artificial Sequence
<220> FEATURE:
<223> OTHER INFORMATION: TCR CDR2 peptide.

<400> SEQUENCE: 73

Leu Gly Gln Gly Pro Glu Phe Leu Thr Tyr Phe Gln Asn Glu Ala Gln
1               5                   10                  15

Leu Glu Lys Ser
        20

<210> SEQ ID NO 74
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 74

Ala Leu Gly Gln Gly Pro Glu Phe Leu Thr Tyr Phe Asn Tyr Glu Ala
1               5                   10                  15

Gln Pro Asp Lys Ser
        20

<210> SEQ ID NO 75
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 75

Thr Leu Gly Gln Gly Ser Glu Val Leu Thr Tyr Ser Gln Ser Asp Ala
1               5                   10                  15

Gln Arg Asp Lys Ser
        20

<210> SEQ ID NO 76
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 76

Lys Ala Lys Lys Pro Pro Glu Leu Met Phe Val Tyr Ser Tyr Glu Lys
1               5                   10                  15

Leu Ser Ile Asn Glu
        20

<210> SEQ ID NO 77
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 77

Ser Ala Lys Lys Pro Leu Glu Leu Met Phe Val Tyr Ser Leu Glu Glu
1               5                   10                  15

Arg Val Glu Asn Asn
        20

<210> SEQ ID NO 78
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 78

Ser Ala Lys Lys Pro Leu Glu Leu Met Phe Val Tyr Asn Phe Lys Glu
1               5                   10                  15

Gln Thr Glu Asn Asn
            20

<210> SEQ ID NO 79
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 79

Thr Met Met Arg Gly Leu Glu Leu Leu Ile Tyr Phe Asn Asn Asn Val
1               5                   10                  15

Pro Ile Asp Asp Ser
            20

<210> SEQ ID NO 80
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 80

Thr Met Met Gln Gly Leu Glu Leu Leu Ala Tyr Phe Arg Asn Arg Ala
1               5                   10                  15

Pro Leu Asp Asp Ser
            20

<210> SEQ ID NO 81
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 81

Asp Ser Lys Lys Phe Leu Lys Ile Met Phe Ser Tyr Asn Asn Lys Glu
1               5                   10                  15

Leu Ile Ile Asn Glu
            20

<210> SEQ ID NO 82
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 82

Lys Leu Glu Glu Glu Leu Lys Phe Leu Val Tyr Phe Gln Asn Glu Glu
1               5                   10                  15

Leu Ile Gln Lys Ala
            20

<210> SEQ ID NO 83
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 83

Thr Leu Glu Glu Glu Leu Lys Phe Phe Ile Tyr Phe Gln Asn Glu Glu
1               5                   10                  15

Ile Ile Gln Lys Ala
            20

<210> SEQ ID NO 84
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 84

Asp Pro Gly Met Glu Leu His Leu Ile His Tyr Ser Tyr Gly Val Asn
1               5                   10                  15

Ser Thr Glu Lys Gly
            20

<210> SEQ ID NO 85
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 85

Asp Pro Gly His Gly Leu Arg Leu Ile His Tyr Ser Tyr Gly Val Lys
1               5                   10                  15

Asp Thr Asp Lys Gly
            20

<210> SEQ ID NO 86
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 86

Asp Leu Gly His Gly Leu Arg Leu Ile His Tyr Ser Tyr Gly Val Gln
1               5                   10                  15

Asp Thr Asn Lys Gly
            20

<210> SEQ ID NO 87
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 87

Asp Leu Gly His Gly Leu Arg Leu Ile His Tyr Ser Tyr Gly Val Lys
1               5                   10                  15

Asp Thr Asn Lys Gly
            20

<210> SEQ ID NO 88
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 88

Asp Leu Gly His Gly Leu Arg Leu Ile His Tyr Ser Tyr Gly Val His
1               5                   10                  15

```
Asp Thr Asn Lys Gly
         20

<210> SEQ ID NO 89
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 89

Asp Leu Gly His Gly Leu Arg Leu Ile Tyr Tyr Ser Ala Ala Ala Asp
1               5                   10                  15

Ile Thr Asp Lys Gly
         20

<210> SEQ ID NO 90
<211> LENGTH: 19
<212> TYPE: PRT
<213> ORGANISM: Artificial Sequence
<220> FEATURE:
<223> OTHER INFORMATION: TCR CDR2 peptide.

<400> SEQUENCE: 90

Gly Leu Arg Leu Ile His Tyr Ser Val Gly Ala Gly Ile Thr Asp Gln
1               5                   10                  15

Gly Glu Val

<210> SEQ ID NO 91
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 91

Asp Pro Gly Met Gly Leu Arg Leu Ile His Tyr Ser Val Gly Glu Gly
1               5                   10                  15

Thr Thr Ala Lys Gly
         20

<210> SEQ ID NO 92
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 92

Asp Pro Gly Met Gly Leu Arg Leu Ile Tyr Tyr Ser Ala Ser Glu Gly
1               5                   10                  15

Thr Thr Asp Lys Gly
         20

<210> SEQ ID NO 93
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 93

Asp Pro Gly Met Gly Leu Arg Arg Ile His Tyr Ser Val Ala Ala Gly
1               5                   10                  15
```

```
Ile Thr Asp Lys Gly
            20

<210> SEQ ID NO 94
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 94

Asp Leu Gly Leu Gly Leu Arg Leu Ile His Tyr Ser Asn Thr Ala Gly
1               5                  10                  15

Thr Thr Gly Lys Gly
            20

<210> SEQ ID NO 95
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 95

Asp Pro Gly Met Gly Leu Lys Leu Ile Tyr Tyr Ser Val Gly Ala Gly
1               5                  10                  15

Ile Thr Asp Lys Gly
            20

<210> SEQ ID NO 96
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 96

Asp Pro Gly Met Gly Leu Arg Leu Ile Tyr Tyr Ser Ala Ala Ala Gly
1               5                  10                  15

Thr Thr Asp Lys Glu
            20

<210> SEQ ID NO 97
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 97

Asp Pro Gly Leu Gly Leu Arg Gln Ile Tyr Tyr Ser Met Asn Val Glu
1               5                  10                  15

Val Thr Asp Lys Gly
            20

<210> SEQ ID NO 98
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 98

Asp Pro Gly Leu Gly Leu Arg Leu Ile Tyr Tyr Ser Phe Asp Val Lys
1               5                  10                  15
```

-continued

Asp Ile Asn Lys Gly
            20

<210> SEQ ID NO 99
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 99

Val Met Gly Lys Glu Ile Lys Phe Leu Leu His Phe Val Lys Glu Ser
1               5                   10                  15

Lys Gln Asp Glu Ser
            20

<210> SEQ ID NO 100
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 100

Asp Pro Gly Gln Gly Leu Arg Leu Ile Tyr Tyr Ser Gln Ile Val Asn
1               5                   10                  15

Asp Phe Gln Lys Gly
            20

<210> SEQ ID NO 101
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 101

Asp Pro Gly Gln Gly Leu Arg Leu Ile Tyr Tyr Ser His Ile Val Asn
1               5                   10                  15

Asp Phe Gln Lys Gly
            20

<210> SEQ ID NO 102
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 102

Leu Pro Glu Glu Gly Leu Lys Phe Met Val Tyr Leu Gln Lys Glu Asn
1               5                   10                  15

Ile Ile Asp Glu Ser
            20

<210> SEQ ID NO 103
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 103

Asn Gln Asn Lys Glu Phe Met Leu Leu Ile Ser Phe Gln Asn Glu Gln
1               5                   10                  15

Val Leu Gln Glu Thr
            20

<210> SEQ ID NO 104
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 104

Asn Gln Asn Lys Glu Phe Met Phe Leu Ile Ser Phe Gln Asn Glu Gln
1               5                   10                  15

Val Leu Gln Glu Met
            20

<210> SEQ ID NO 105
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 105

Ala Ala Gly Arg Gly Leu Gln Leu Leu Phe Tyr Ser Val Gly Ile Gly
1               5                   10                  15

Gln Ile Ser Ser Glu
            20

<210> SEQ ID NO 106
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 106

Ala Ala Gly Arg Gly Leu Gln Leu Leu Phe Tyr Ser Ile Gly Ile Asp
1               5                   10                  15

Gln Ile Ser Ser Glu
            20

<210> SEQ ID NO 107
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 107

Ile Leu Gly Gln Gly Pro Glu Leu Leu Val Gln Phe Gln Asp Glu Ser
1               5                   10                  15

Val Val Asp Asp Ser
            20

<210> SEQ ID NO 108
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 108

Asn Leu Gly Gln Gly Pro Glu Leu Leu Ile Arg Tyr Glu Asn Glu Glu
1               5                   10                  15

```
Ala Val Asp Asp Ser
        20

<210> SEQ ID NO 109
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 109

Ile Leu Gly Gln Gly Pro Lys Leu Leu Ile Gln Phe Gln Asn Asn Gly
1               5                   10                  15

Val Val Asp Asp Ser
        20

<210> SEQ ID NO 110
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 110

Ile Leu Gly Gln Lys Val Glu Phe Leu Val Ser Phe Tyr Asn Asn Glu
1               5                   10                  15

Ile Ser Glu Lys Ser
        20

<210> SEQ ID NO 111
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 111

Gly Pro Gly Gln Asp Pro Gln Phe Phe Ile Ser Phe Tyr Glu Lys Met
1               5                   10                  15

Gln Ser Asp Lys Gly
        20

<210> SEQ ID NO 112
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 112

Gly Pro Gly Gln Asp Pro Gln Phe Leu Ile Ser Phe Tyr Glu Lys Met
1               5                   10                  15

Gln Ser Asp Lys Gly
        20

<210> SEQ ID NO 113
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 113

Lys Ser Ser Gln Ala Pro Lys Leu Leu Phe His Tyr Tyr Asn Lys Asp
1               5                   10                  15
```

Phe Asn Asn Glu Ala
            20

<210> SEQ ID NO 114
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 114

Lys Ser Ser Gln Ala Pro Lys Leu Leu Phe His Tyr Tyr Asp Lys Asp
1               5                   10                  15

Phe Asn Asn Glu Ala
            20

<210> SEQ ID NO 115
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 115

Val Leu Lys Asn Glu Phe Lys Phe Leu Ile Ser Phe Gln Asn Glu Asn
1               5                   10                  15

Val Phe Asp Glu Thr
            20

<210> SEQ ID NO 116
<211> LENGTH: 21
<212> TYPE: PRT
<213> ORGANISM: Artificial Sequence
<220> FEATURE:
<223> OTHER INFORMATION: TCR CDR2 peptide.

<400> SEQUENCE: 116

Val Leu Lys Asn Glu Phe Lys Phe Leu Val Ser Phe Gln Asn Glu Asn
1               5                   10                  15

Val Phe Asp Glu Thr
            20

<210> SEQ ID NO 117
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 117
ggaaacccag aggcattgac                                              20

<210> SEQ ID NO 118
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 118
tcaggatctg gcccttgaac                                              20

<210> SEQ ID NO 119
<211> LENGTH: 19
<212> TYPE: DNA
<213> ORGANISM: Artificial Sequence -continued

```
<220> FEATURE:
<223> OTHER INFORMATION: Oligonucleotide primer.

<400> SEQUENCE: 119
ggcccttctc caggacaga                                                19

<210> SEQ ID NO 120
<211> LENGTH: 20
<212> TYPE: DNA
<213> ORGANISM: Artificial Sequence
<220> FEATURE:
<223> OTHER INFORMATION: Oligonucleotide primer.

<400> SEQUENCE: 120
gctgatcatg gctgggttgt                                               20
```

METHODS FOR DETECTING AND TREATING AUTOIMMUNE DISORDERS

CROSS REFERENCE TO RELATED APPLICATIONS

This application is the U.S. National Stage of International Application No. PCT/US2005/026915, filed Jul. 29, 2005, which was published in English under PCT Article 21(2), which in turn claims the benefit of U.S. Provisional Patent Application No. 60/592,431 filed Jul. 30, 2004 and U.S. Provisional Patent Application No. 60/667,820 filed Apr. 1, 2005, both of which are incorporated herein by reference in their entirety.

STATEMENT OF GOVERNMENT SUPPORT

This invention was made with United States government support pursuant to grants NS23444, NS45445 and NS23221 from the National Institutes of Health; grants from the Immune Tolerance Network, the National Multiple Sclerosis Society, The Nancy Davis MS Center Without Walls, and the Department of Veterans' Affairs. The United States government has certain rights in the invention.

FIELD OF THE DISCLOSURE

This disclosure relates to the field of autoimmune disorders, specifically to the treatment of multiple sclerosis.

BACKGROUND

Autoimmune diseases such as multiple sclerosis (MS) may result from the failure of tolerance mechanisms to prevent expansion of pathogenic T cells directed at myelin determinants or other self-tissue antigens. These tolerance mechanisms include CD4+CD25+ regulatory T cells (Treg cells) (Sakaguchi et al., *J. Immunol.* 155:1151-64, 1995) that may have specificity for TCR determinants (Buenafe et al., *J. Neurosci. Res.* 76:129-40, 2004; Kumar, *J. Clin. Invest.* 114: 1222-26, 2004). CD4+CD25+ Treg cells represent a unique lineage that maintains central tolerance in the thymus (Sakaguchi, *Cell* 101:455-58, 2000; Shevach, *Ann. Rev. Immunol.* 18:423-49, 2000). The Treg cells also exert their regulatory function in the periphery where they constitute ~5-10% of circulating CD4+ cells. However, peripheral Treg cells may also be induced from CD4+CD25-precursors (Walker et al., *J. Clin. Invest.* 112:1437-43, 2003).

Treg cells provide a critical level of protection against autoimmunity, transplant rejection and lymphoproliferative disease in several mouse models (Coffer and Burgering, *Nature Rev.* 4:889-99, 2004). The FOXP3 transcription factor is predominantly expressed by the Treg cell lineage and appears to act as a master regulator for cytokine production and cell-cell contact dependent inhibition of T effector cell activation (Fontenot et al., *Nature Immunol.* 4:330-36, 2003; Hori et al., *Science* 299:1057-61, 2003; Khattri et al., *Nature Immunol.* 4:337-42, 2003; Ramsdell, *Immunity* 19:165-68, 2003) that may involve membrane-bound perforin molecules (Grossman et al., *Immunity* 21:589-601, 2004). Recessive X-linked mutations in the FoxP3 gene in scurfy mice (Brunkow et al., *Nature Genet.* 27:68-73, 2001) and in humans with IPEX (inununodysregulation, polyendocrinopathy and enteropathy, X-linked) (Bennett et al., *Nature Genet.* 27:20-21, 2001; Gambineri et al., *Current Opin. Rheumatol.* 15:430-35, 2003; Wildin et al., *Nature Genet.* 27:18-20, 2001) lead to a fatal lymphoproliferative autoimmune condition.

Multiple sclerosis is a chronic, neurological, autoimmune, demyelinating disease. Multiple sclerosis can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. In the United States there are about 250,000 to 400,000 persons with MS, and every week about 200 new cases are diagnosed. Worldwide, MS may affect 2.5 million individuals. Because it is not contagious, which would require U.S. physicians to report new cases, and because symptoms can be difficult to detect, the incidence of disease is only estimated and the actual number of persons with MS could be much higher.

The pathology of MS is characterized by an abnormal immune response directed against the central nervous system. In particular, T lymphocytes are activated against the myelin sheath of the neurons of the central nervous system causing demyelination. In the demyelination process, myelin is destroyed and replaced by scars of hardened "sclerotic" tissue which is known as plaque. These lesions appear in scattered locations throughout the brain, optic nerve, and spinal cord. Demyelination interferes with conduction of nerve impulses, which produces the symptoms of multiple sclerosis. Most subjects recover clinically from individual bouts of demyelination, producing the classic remitting and exacerbating course of the most common form of the disease known as relapsing-remitting multiple sclerosis.

Multiple sclerosis develops in genetically predisposed individuals and is most likely triggered by environmental agents such as viruses (Martin et al., *Ann. Rev. Immunol.* 10:153-87, 1992). According to current hypotheses, activated autoreactive CD4+T helper cells (Th1 cells) which preferentially secrete interferon-gamma (IFN-γ) and tumor necrosis factors alpha/beta (TNF-α/β), induce inflammation and demyelination in MS (Martin et al., *Ann. Rev. Immunol.* 10:153-87, 1992). Available data suggest that the predisposition to mount a Th1-like response to a number of different antigens is an important aspect of MS disease pathogenesis. Proinflanunatory cytokines (such as IFN-γ, TNF-α/β) and chemokines secreted by Th1 cells contribute to many aspects of lesion development including opening of the blood-brain-barrier, recruitment of other inflammatory cells, activation of resident glia (micro- and astroglia) and the effector phase of myelin damage via nitrogen and oxygen radicals secreted by activated macrophages (Wekerle et al., *Trends Neuro Sci.* 9:271-77, 1986).

There are currently four approved treatments for relapsing-remitting MS, three types of IFN-β (the Interferon-B multiple sclerosis study group, *Neurology* 43:655-61, 1993; the IFNB Multiple Sclerosis Study Group and the University of British Columbia MS/MRI Analysis Group, *Neurology* 45:1277-85, 1995; Jacobs et al., *Ann. Neurol.* 39:285-94, 1996), and copolymer-1 (Johnson KP, Group tCMST, *J. Neural.* 242: S38, 1995). Treatment failures have been linked to the development of neutralizing anti-IFN-β antibodies, although their role is also not completely understood at present (the IFNB Multiple Sclerosis Study Group and the University of British Columbia MS/MRI Analysis Group, *Neurology* 47:889-94, 1996). Failure to respond to IFN-β is not a rare event, and therefore it is important to identify new therapeutic protocols.

SUMMARY OF THE DISCLOSURE

Disclosed herein is a method for inhibiting an autoimmune disease. The method includes administering to a subject a therapeutically effective amount of a composition that increases FOXP3 expression, thereby inhibiting the autoimmune disease.

In another embodiment, a method of inducing immunosuppression is also described herein. This method includes administering to a subject a therapeutically effective amount of a composition that increases FOXP3 expression, thereby inducing immunosuppression.

Further disclosed herein are methods for detecting in a subject an autoimmune disease or a predisposition to an autoimmune disease. Such methods involve determining that the expression of FOXP3 in a biological sample from a subject differs from a reference level of expression of FOXP3; wherein a difference in the expression of FOXP3 in the biological sample as compared to the reference detects in the subject an autoimmune disease or a predisposition to an autoimmune disease.

Also disclosed are methods for assessing the efficacy of a therapy for an autoimmune disease. These methods involve determining that the expression of FOXP3 in a first biological sample taken from a subject differs from the expression of FOXP3 in a second biological sample taken from the subject after a period of treatment with a therapy for an autoimmune disease; wherein a difference in the expression of FOXP3 in the first biological sample as compared to the second biological sample assesses the efficacy of a therapy for an autoimmune disease.

The foregoing and other features and advantages will become more apparent from the following detailed description of several embodiments, which proceeds with reference to the accompanying figures.

BRIEF DESCRIPTION OF THE FIGURES

FIG. 9A shows the pairwise comparison of FOXP3 message in five age and gender matched sets of MS patients and HC subjects. FOXP3 message was assessed by real-time PCR on magnetic bead-sorted cells. Average message ±standard deviation is shown in FIG. 9B. MS patients have significantly less FOXP3 message than HC subjects ($p=0.0475$, t-test).

FIG. 10A shows Western blot results from age and gender matched MS and HC. FOXP3 protein stains as two bands of approximately 50 kD. Densitometry was used to give a numerical value to the FOXP3 bands for each subject, and these results are depicted in the lower panel of FIG. 10A. Each MS patient shows less FOXP3 protein than the adjacent age and gender matched HC. The matched pairs are shown in the same order as in FIG. 9A. FIG. 10B shows mean FOXP3 protein expression ±standard deviation. There is a highly significant difference in the FOXP3 protein levels of HC vs. MS (p<0.01, t-test).

FIG. 11A shows the correlation between FOXP3 message and FOXP3 protein in 5 MS patients and 5 HC. FOXP3 message in CD4+CD25+ T cells was determined by real time PCR, and FOXP3 protein in CD4+CD25+ T cells was determined by western blot followed by densitometry. There is a significant positive correlation between FOXP3 message and FOXP3 protein in CD4+CD25+ T cells (p=0.04, Spearman rank-order test). FIG. 11B shows the highly significant correlation between FOXP3 message and $I_{50}$ values (p<0.01, Spearman rank order test). Lower $I_{50}$ values, which indicate better suppression, are correlated with higher levels of FOXP3 message in CD4+CD25+ T cells. FIG. 11C shows the highly significant correlation between $I_{50}$ values and FOXP3 protein in CD4+CD25+ T cells (p<0.01, Spearman rank-order test). Individuals with higher levels of FOXP3 protein in CD4+CD25+ T cells show better suppression (lower $I_{50}$ value).

SEQUENCE LISTING

Figure 1:
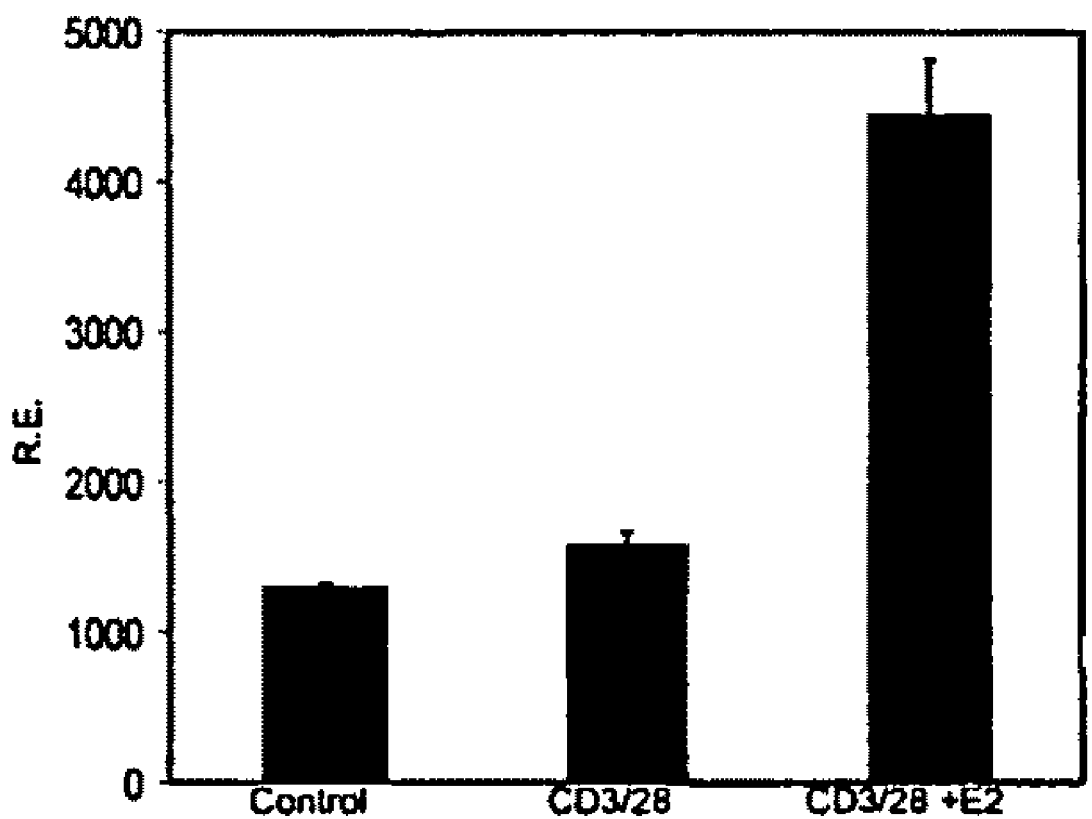
FIG. 1 is a graph illustrating real-time RT-PCR analysis of Foxp3 expression in vitro in purified (>99%) CD4+CD25− T cells. E2 in combination with TCR stimulation by anti-CD3 antibody for 24 hours induced Foxp3 mRNA approximately 3-fold over levels in untreated cells or in anti-CD3 stimulated cells in the absence of E2. Foxp3 levels are shown relative to the housekeeping gene L32. Error bars are standard deviation of triplicate samples. One representative result of three is shown.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-116 show the amino acid sequence of various TCR CDR2 peptides.

SEQ ID NOs: 117-120 show the nucleic acid sequence of various PCR primers.

DETAILED DESCRIPTION

I. Abbreviations
  CDR: complementarity determining region
  EAE: experimental autoimmune encephalomyelitis
  ELISA: enzyme-linked immunoabsorbent assay
  FACS: fluorescence activated cell sorting
  FBS: fetal bovine serum
  FITC: fluorescein isothiocyanate
  g: gram
  GVHD: graft-versus-host disease
  HC: healthy control(s)
  IFA: incomplete Freund's adjuvant
  i.p.: intraperitoneal
  IU: international units
  kg: kilogram
  mAb: monoclonal antibody
  mg: milligram
  PBMC: peripheral blood mononuclear cell(s)
  PE: phycoerythrin
  PEG: polyethylene glycol
  PI: propidium iodide
  PVP: polyvinylpyrrolidone
  RT-PCR: reverse transcriptase polymerase chain reaction
  SE: standard error
  Treg: regulatory T cell
  µg: microgram II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. The materials, methods and examples are illustrative only and not intended to be limiting.

In order to facilitate review of the various embodiments of this disclosure, the following explanations of specific terms are provided:

Adjuvant: A substance that non-specifically enhances the immune response to an antigen. Non-limiting examples include complete Freund's adjuvant (CFA), incomplete Freund's adjuvant (IFA), aluminum salts, Amplivax (CpG oligodeoxynucleotides; Mosemann et al., *J. Immunol.* 173:4433, 2004), and IVX-908 (ID Biomedical of Canada). Development of vaccine adjuvants for use in humans is reviewed in, for example, Singh et al. (*Nat. Biotechnol.* 17:1075-1081, 1999).

Animal: Living multi-cellular vertebrate organisms, a category that includes, for example, mammals and birds. The term mammal includes both human and non-human mammals. Similarly, the term "subject" or "patient" includes both human and veterinary subjects, for example, humans, non-human primates, dogs, cats, horses, and cows.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes.

Autoimmune Disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

Beta interferon: Any beta interferon including interferon-beta 1a and interferon-beta 1b. Interferonbeta 1a is a 166 amino acid glycoprotein with a predicted molecular weight of approximately 22,500 daltons. The interferonbeta 1a known as Avonex® is produced by recombinant DNA technology utilizing mammalian cells (Chinese Hamster Ovary cells) into which the human interferon-beta gene has been introduced. The amino acid sequence of Avonex® is identical to that of natural human interferon-beta. Interferon induced gene products and markers including 2',5'-oligoadenylate synthetase, $\beta_2$-microglobulin, and neopterin, have been measured in the serum and cellular fractions of blood collected from patients treated with Avonex®. Avonex® was approved in 1996 and is marketed by Biogen, Inc. Avonex® has been demonstrated to decrease the number of gadolinium (Gd)-enhanced lesions in subjects who were administered the drug for two years by up to 13% and to improve approximately 22% of subjects' Expanded Disability Status Scale (EDSS) scores.

Another interferonbeta 1a was approved in 2002 and is known as Rebif®, marketed by Serono, Inc. The interferonbeta 1a known as Rebif®, has recently been approved for treatment of relapsing-remitting MS. The primary difference between Avonex® and Rebif® is the approved method of administration—intramuscular injection for the former and subcutaneous injection for the latter. According to Samkoff, *Hosp. Phys.*, p. 21-7 (2002), Rebif® can reduce relapse rates by 33% in subjects taking the drug.

Interferonbeta 1b is a highly purified protein that has 165 amino acids and an approximate molecular weight of 18,500 daltons. An interferonbeta 1b known as Betaseron® was approved as a treatment for MS in 1993 and is marketed by Berlex Laboratories, Inc. Betaseron® is manufactured by bacterial fermentation of a strain of *Escherichia coli* that bears a genetically engineered plasmid containing the gene for human interferon-beta. The native gene was obtained from human fibroblasts and altered to substitute serine for the cysteine residue found at position 17. According to the *Physicians' Desk Reference* (1996), Betaseron® has been demonstrated to reduce the exacerbation rate in subjects taking the drug by about 31%. The mechanisms by which interferonbeta 1b exerts its actions in multiple sclerosis are not clearly understood. However, it is known that the biologic response-modifying properties of interferonbeta 1b are mediated through its interactions with specific cell receptors. The binding of interferonbeta 1b to these receptors induces the expression of a number of interferon induced gene products (e.g., 2',5'-oligoadenylate synthetase, protein kinase, and indoleamine 2,3-dioxygenase) that are believed to be the mediators of the biological actions of interferon-beta 1*b*.

CD4: Cluster of differentiation factor 4. A T-cell surface protein that mediates interaction with MHC class II molecules. This cell surface antigen is also known as T4, Leu-3, OKT4 or L3T4. CD4 is a 55 kDa transmembrane glycoprotein belonging to the immunoglobulin superfamily. A T-cell that expresses CD4 is a "CD4$^+$" T-cell. Likewise, a T-cell that does not express CD4 is a "CD4$^-$" T-cell.

CD25: Cluster of differentiation factor 25, the IL-2 receptor alpha chain. A T cell that expresses CD25 is a "CD25+" T cell.

Clinically isolated syndrome (CIS): In the context of concerns about multiple sclerosis, a clinically isolated syndrome (CIS) is a single clinical event that is indicative of demyelination—for example, an attack of optic neuritis in one eye, or an episode of numbness on one side—that is unaccompanied by any other clinical sign or symptom.

Individuals who experience a clinically isolated syndrome may or may not go on to develop multiple sclerosis. The challenge for the physician is to determine the likelihood that a person experiencing this type of demyelinating event is subsequently going to develop MS. Studies have shown that when the CIS is accompanied by MRI-detected brain lesions that are consistent with those seen in MS, there is a high risk of a second neurologic event, and therefore a diagnosis of clinically definite MS, within several years. Individuals who experience CIS with no evidence of MRI-detected lesions are at relatively low risk for developing MS over the same time period.

In some contexts, a "clinically isolated syndrome" is also referred to as a "confirmed isolated syndrome."

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many cytokines act as cellular survival factors by preventing programmed cell death. Cytokines include both naturally occurring peptides and variants that retain full or partial biological activity.

Estrogen: The term "estrogen" refers to the steroids commonly known as 17β-estradiol (E2), 17α-ethynil estradiol (EE), estrone (E1), and estriol (E3). Also included within the term "estrogen" are metabolites and derivatives of EE, E1, E2, and E3. Such metabolites and derivatives act as agonists of the estrogen receptor and have a similar core steroid structure as EE, E1, E2, or E3, but can have one or more different groups (for example, hydroxyl, ketone, halide, and the like) at one or more ring positions. Those skilled in the art can readily determine whether such metabolites and derivatives are agonists of estrogen by in vitro assays that measure signaling through the estrogen receptor.

FOXP3: A transcription factor also known as "FKH$^{sf}$" or "scurfin." Exemplary nucleic acids encoding FOXP3, and exemplary amino acids sequences of FOXP3 polypeptide are disclosed in published PCT Application No. 02/090600 A2, which is incorporated herein by reference. The FOXP3 transcription factor is predominately expressed by Treg cells. FOXP3 is a regulator of cytokine production and cell to cell contact dependent inhibition of T effector cell activation. Mutations in FOXP3 have been shown to be involved in scurfy mice and in humans with) IPEX (Immunodysregulation, Polyendocrinopathy, and Enteropathy, X-linked). FOXP3 expression confers suppressive function to peripheral CD4+CD25+ Treg cells.

Graft-Versus-Host Disease (GVHD): A common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor.

There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines.

Immune response: A response of a cell of the immune system, such as a B cell, T cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunosuppression: Nonspecific unresponsiveness of cellular and/or humoral immunity. Immunosuppression refers to the prevention or diminution of an immune response and occurs when T and/or B cells are depleted in number or suppressed in their reactivity, expansion or differentiation. Immunosuppression may arise from activation of specific or non-specific Treg cells, from cytokine signaling, in response to irradiation, or by drugs that have generalized immunosuppressive effects on T and B cells.

Immunosuppressive agent: A molecule, such as a chemical compound, small molecule, steroid, nucleic acid molecule, or other biological agent, that can decrease an immune response such as an inflammatory reaction. Immunosuppressive agents include, but are not limited to an agent of use in treating an autoimmune disorder. Specific, non-limiting examples of immunosuppressive agents are non-steroidal anti-inflammatory agents, cyclosporine A, FK506, and anti-CD4. In additional examples, the agent is a biological response modifier, such as Kineret® (anakinra), Enbrel® (etanercept), or Remicade® (infliximab), a disease-modifying antirheumatic drug (DMARD), such as Arava® (leflunomide), a nonsteroidal anti-inflammatory drug (NSAIDs), specifically a Cyclo-Oxygenase-2 (COX-2) inhibitor, such as Celebrex® (celecoxib) and Vioxx® (rofecoxib), or another product, such as Hyalgan® (hyaluronan) and Synvisc® (hylan G-F20).

Inflammation: A complex series of events, including dilatation of arterioles, capillaries and venules, with increased permeability and blood flow, exudation of fluids, including plasma proteins and leucocytic migration into the inflammatory focus. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

Inhibiting or Treating a Disease: Inhibiting the full development of a disease or condition, for example, in a subject who is at risk for a disease such as an autoimmune disease (e.g., MS), graft-versus-host disease, or rejection of a transplanted tissue or organ. "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated/purified: An "isolated" or "purified" biological component (such as a nucleic acid, peptide or protein) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell. Preferably, a preparation is purified such that the biological component represents at least 50%, such as at least 70%, at least 90%, at least 95%, or greater of the total biological component content of the preparation.

Leukocyte: Cells in the blood, also termed "white cells," that are involved in defending the body against infective organisms and foreign substances. Leukocytes are produced in the bone marrow. There are five main types of leukocytes, subdivided into two main groups: polymorphonuclear leukocytes (neutrophils, eosinophils, basophils) and mononuclear leukocytes (monocytes and lymphocytes).

Lymphocyte: Any of the mononuclear nonphagocytic leukocytes, found in the blood, lymph, and lymphoid tissues (such as the thymus), that are the body's immunologically competent cells and their precursors. Lymphocytes are divided on the basis of ontogeny and function into at least two classes, B and T lymphocytes (a.k.a., B and T cells), which are responsible for humoral and cellular immunity, respectively.

Magnetic Resonance Imaging: A noninvasive diagnostic technique that produces computerized images of internal body tissues and is based on nuclear magnetic resonance of atoms within the body induced by the application of radio waves. Brain MRI is an important tool for understanding the dynamic pathology of multiple sclerosis. $T_2$-weighted brain MRI defines lesions with high sensitivity in multiple sclerosis and is used as a measure of disease burden. However, such high sensitivity occurs at the expense of specificity, as $T_2$ signal changes can reflect areas of edema, demyelination, gliosis and axonal loss. Areas of gadolinium (Gd) enhancement demonstrated on $T_1$-weighted brain MRI are believed to reflect underlying blood—brain barrier disruption from active perivascular inflammation. Such areas of enhancement are transient, typically lasting <1 month. Gadolinium-enhanced $T_1$-weighted brain MRI are therefore used to assess disease activity. Most T2-weighted (T2) lesions in the central white matter of subjects with multiple sclerosis begin with a variable period of T1-weighted (T1) gadolinium (Gd) enhancement and that T1 Gd-enhancing and T2 lesions represent stages of a single pathological process. The brain MRI techniques for assessing T1 and T2 Gd-enhancing lesions are standard (e.g., see Lee et al., *Brain* 122 (Pt 7):1211-2, 1999).

Multiple sclerosis: An autoimmune disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesion's, hypointensive "black holes" (representing gliosis and axonal pathology), and brain atrophy on T1-weighted studies. Serial MRI studies can be used to indicate disease progression. The status of MS patients can be evaluated by longitudinal, monthly follow-up of magnetic resonance (MR1) activity in the brain of MS patients. MRI offers a unique set of outcome measures for phase I/II clinical trials in small cohorts of patients, and is thus well suited to establish data for proof of principle for novel therapeutic strategies (e.g., see Harris et al., *Ann. Neurol.* 29:548-555, 1991; MacFarland et al., *Ann. Neural.* 32:758-766, 1992; Stone et al., *Ann. Neurol.* 37:611-619, 1995).

Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form.

There are currently four approved treatments for relapsing-remitting MS, three types of IFN-β (the Interferon-B multiple sclerosis study group, *Neurology.* 43:655-661, 1993; the IFNB Multiple Sclerosis Study Group and the University of British Columbia MS/MRI Analysis Group, *Neurology.* 45:1277-1285, 1995; Jacobs et al., *Ann. Neurol.* 39:285-294, 1996), and copolymer-1 (Johnson K P, CMST, *J. Neurol.* 242:S38, 1995) (see also below).

Antibodies that bind the interleukin-2 receptor antibody have also been used in the treatment of multiple sclerosis. For example, an IL-2 receptor antibody that specifically binds Tac (p55), such as Zenapax® have been utilized. Other anti-p55 agents of use in treating multiple sclerosis include the chimeric antibody basiliximab (Simulect®), BT563 (see Baan et al., *Transplant. Proc.* 33:224-2246, 2001), and 7G8. Basiliximab has been reported to be beneficial in preventing allograft rejection (Kahan et al., *Transplantation* 67:276-84, 1999), and treating psoriasis (Owen & Harrison, *Clin. Exp. Dermatol.* 25:195-7, 2000). Another exemplary human anti-p55 antibody is HuMax-TAC, being developed by Genmab. Additional antibodies that specifically bind the IL-2 receptor are known in the art. For example, see U.S. Pat. No. 5,011,684; U.S. Pat. No. 5,152,980; U.S. Pat. No. 5,336,489; U.S. Pat. No. 5,510,105; U.S. Pat. No. 5,571,507; U.S. Pat. No. 5,587,162; U.S. Pat. No. 5,607,675; U.S. Pat. No. 5,674,494; U.S. Pat. No. 5,916,559.

Peptide: A polymer in which the monomers are amino acid residues which are joined together through amide bonds. When the amino acids are alpha-amino acids, either the L-optical isomer or the D-optical isomer can be used. The terms "peptide" or "polypeptide" as used herein are intended to encompass any amino acid sequence and include modified sequences such as glycoproteins. The term "peptide" is specifically intended to cover naturally occurring peptides, as well as those which are recombinantly or synthetically produced. The term "residue" or "amino acid residue" includes reference to an amino acid that is incorporated into a peptide, polypeptide, or protein.

The term "fragment" refers to a portion of a polypeptide that is at least 8, 10, 15, 20 or 25 amino acids in length. The term "functional fragments of a polypeptide" refers to all fragments of a polypeptide that retain an activity of the polypeptide (e.g., the binding of an antigen). Biologically functional fragments, for example, can vary in size from a polypeptide fragment as small as an epitope capable of binding an antibody molecule to a large polypeptide capable of participating in the characteristic induction or programming of phenotypic changes within a cell. The term "soluble" refers to a form of a polypeptide that is not inserted into a cell membrane.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of TCR peptides and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Pulsatile Dose: A dose administered as a bolus. A pulsatile dose can be administered to a subject as a single administration, such as by direct injection or by an intravenous infusion during a specified time period. Thus, the pulsatile dose can be a "push" or rapid dose, but need not be, as it can be administered over a defined time period, such as in an infusion. Repeated pulsatile doses can be administered to a subject, such as a bolus administered repeatedly, such as about every one, two, or three months, or about every one, two, three or four weeks or about every one, two or three days in a therapeutic regimen. In this embodiment, the administered dose can be the same amount of an agent, or can be different amounts administered at several time points separated by periods wherein the agent is not administered to the subject, or wherein a decreased amount of the agent is administered to the subject.

Regulatory T Cells (Treg): CD4+CD25+ T cells that prevent the activation and/or expansion of other cell populations, for example CD4+CD25− responder T cells. Reduction or functional alteration of Treg cells leads to the spontaneous development of various organ-specific autoimmune diseases, including, for example, autoimmune thyroiditis, gastritis, and type 1 diabetes (see, for example, Sakaguchi et al., *J. Immunol.* 155:1151-64, 1995; Suri-Payer et al., *J. Immunol.* 160: 1212-18, 1998; Itoh et al., *J. Immunol.* 162:5317-26, 1999). The FOXP3 transcription factor is predominantly expressed by the Treg cell lineage (Fontenot et al., *Nature Immunol* 4:330-36, 2003; Hon et al., *Science* 299:1057-61, 2003).

Responder T Cells: A subpopulation of mature T cells that facilitate an immune response through cell activation and/or the secretion of cytokines. In one embodiment, the responder T cells are CD4+CD25− T cells. In another embodiment, the responder T cells are CD8+ CD25− T cells. One specific, non-limiting example of a responder T cell is a T lymphocyte that proliferates upon stimulation by antigen or a stimulator cell, such as an allogenic stimulator cell. Another specific, non-limiting example of a responder T cell is a T lymphocyte whose responsiveness to stimulation can be suppressed by Treg cells.

Sample: A portion, piece, or segment that is representative of a whole. This term encompasses any material, including for instance samples obtained from a subject.

A "biological sample" is a sample obtained from a subject. As used herein, biological samples include all clinical samples useful for detection of FOXP3 in subjects, including, but not limited to, cells; tissues; bodily fluids, such as blood, derivatives and fractions of blood, such as serum; and biopsied or surgically removed tissue, including tissues that are, for example, unfixed, frozen, fixed in formalin and/or embedded in paraffin. In particular embodiments, the biological sample is obtained from a subject, such as blood or serum.

Subject: A human or non-human animal. In one embodiment, the subject has an autoimmune disease, such as multiple sclerosis.

A subject who has multiple sclerosis who has failed a therapeutic protocol (such as administration of interferon-beta or a TCR peptide) is a subject who does not respond or fails to respond adequately to the therapy, such that their condition has not improved sufficiently, not changed, or deteriorated in response to treatment with a therapeutically effective amount of the drug. As disclosed herein, this failure to respond can be measured by assessing FOXP3 in a sample from the subject. A subject who has failed a therapeutic protocol can require escalating doses of the drug to achieve a desired effect.

Symptom and sign: Any subjective evidence of disease or of a subject's condition, that is, such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with an autoimmune disease (e.g., MS).

T Cell: A lymphoid cell that mediates cell-mediated immune responses in the adaptive immune system. Adaptive cell-mediated immunity is immunity that confers resistance to pathogenic conditions (including, for example, neoplasia or infection by microbes, viruses, or bacteria) that are not susceptible to the innate immune response (for example, not susceptible to the antibody-making cells of the immune system). T cells mature in the thymus, circulate between blood and lymph, populate secondary lymphoid tissues, and are recruited to peripheral sites of antigen exposure. T cells generally cannot recognize foreign antigens without the help of antigen presenting cells (APC), such as macrophages, dendritic cells or B-cells that present antigen in conjunction with major histocompatibility complex.

T Cell Receptor (TCR) and TCR Receptor Peptides: Membrane-bound proteins composed of two transmembrane chains that are found on T cells. The T cell receptor recognizes antigen peptides presented in the context of the Major Histocompatibility Complex (MHC) proteins. In the case of CD4+ T cells, the antigen peptides must be presented on Class II MHC, and in the case of CD8+ T cells, the antigen peptides must be presented on Class I MHC. The T cell antigen receptor consists of either an alpha/beta chain or a gamma/delta chain associated with the CD3 molecular complex. The two transmembrane chains consist of two domains, called a "variable" and a "constant" domain, and a short hinge that connects the two domains. The V domains include V-, D-, and J-immunoglobulin like elements in the β chain and V- and J-like elements in the α chain.

A "TCR V" peptide is a portion of the variable (V) region of the TCR itself, such as a peptide that includes about 10, 20, 30, 40 or about 50 consecutive amino acids of the V region of the TCR, or a variant thereof. A "variant" of a TCR peptide is a molecule substantially similar to either the entire peptide or a fragment thereof, such as about 75%, 80%, 90%, 95%, or 99% similar. Variant peptides may be conveniently prepared by direct chemical synthesis or by molecular techniques well known to one of skill in the art. For example, amino acid sequence variants of a TCR V peptide can be prepared by mutations in the nucleic acid encoding the peptide. Such variants include, for example, deletions from, or insertions or substitutions of, residues within the amino acid sequence.

In one specific, non-limiting example, the TCR V peptide is a "TCR V β peptide. In another specific, non-limiting example, the TCR peptide corresponds to the VDJ region of the TCR β chain or the V region of the TCR V α chain. In another embodiment, the peptide corresponds to at least part of one of the three complementarity determining regions (CDR) of the TCR heterodimer, such as the second CDR (CDR2).

Therapeutically effective amount: A quantity of a specified agent sufficient to achieve a desired effect in a subject being treated with that agent. For example, this can be the amount of one or more TCR peptides useful in preventing, ameliorating, and/or treating an autoimmune disorder (e.g., MS) in a subject. Ideally, a therapeutically effective amount of an agent is an amount sufficient to prevent, ameliorate, and/or treat an autoimmune disorder (e.g., MS) in a subject without causing a substantial cytotoxic effect in the subject. The effective amount of an agent useful for preventing, ameliorating, and/ or treating an autoimmune disorder (e.g., MS) in a subject will be dependent on the subject being treated, the severity of the disorder, and the manner of administration of the therapeutic composition.

III. Overview of Several Embodiments

Provided herein in various embodiments is a method for inhibiting an autoimmune disease. In one embodiment, the method includes administering to a subject a therapeutically effective amount of a composition that increases FOXP3 expression, thereby inhibiting the autoimmune disease. In a specific, non-limiting example, the composition includes a therapeutically effective amount of a TCR CDR2 peptide and a therapeutically effective amount of IFA. Exemplary TCR CDR2 peptides include the amino acid sequences set forth in SEQ ID NOs: 1-116 and are shown in Table 1. In another specific example of the method, the composition further includes a therapeutically effective amount of estrogen. In yet another specific example of the method, the composition includes a therapeutically effective amount of estrogen. Exemplary autoimmune diseases include multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, and psoriasis. In one specific, non-limiting example, the subject has relapsing remitting multiple sclerosis.

A method for inducing immunosuppression is also described herein. This method includes administering to a subject a therapeutically effective amount of a composition that increases FOXP3 expression, thereby inducing immunosuppression. In a specific, non-limiting example, the subject has an autoimmune disease. In another specific example of the method, the subject has graft-versus-host disease. In yet another specific example of the method, the subject is a recipient of a transplanted organ. In still another specific example of the method, the method includes a method for treating or inhibiting inflammation.

Also described herein is a method for assessing the efficacy of a therapy for an autoimmune disease. This method includes determining that the expression of FOXP3 in a first biological sample taken from a subject differs from the expression of FOXP3 in a second biological sample taken from the subject after a period of treatment with the therapy for the autoimmune disease, wherein a difference in the expression of FOXP3 in the first biological sample as compared to the second biological sample assesses the efficacy of the therapy for the autoimmune disease. In a specific, non-limiting example, the therapy comprises administration of a therapeutically effective amount of a TCR CDR2 peptide and a therapeutically effective amount of IFA. Exemplary TCR CDR2 peptides include the amino acid sequences set forth in SEQ ID NOs: 1-116. In another specific example of the method, the composition further includes a therapeutically effective amount of estrogen. Exemplary autoimmune diseases include multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, and psoriasis.

A method for detecting in a subject a predisposition to an autoimmune disease is also described herein. This method includes determining that expression of FOXP3 in a biological sample from a subject differs from a reference level of expression of FOXP3, wherein a difference in the expression of FOXP3 in the biological sample as compared to the reference detects in the subject a predisposition to an autoimmune disease. Exemplary autoimmune diseases include multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, and psoriasis.

IV. Method for Inhibiting an Autoimmune Disease

Disclosed herein is a method for inhibiting an autoimmune disease. The method includes administering to a subject a therapeutically effective amount of a composition that increases FOXP3 expression, thereby inhibiting the autoimmune disease.

Examples of an autoimmune disease include, but are not limited to, multiple sclerosis, rheumatoid arthritis, systemic lupus erythematosis, type I diabetes mellitus, Crohn's disease; myasthenia gravis, Grave's disease, scleroderma, Sjogren's syndrome, ulcerative colitis, primary biliary cirrhosis, autoimmune hepatitis, Hashimoto's thyroiditis, ankylosing spondylitis, and psoriasis. The autoimmune disease can be an autoimmune disease related to blood disorders such as autoimmune hemolytic anemia, pernicious anemia and autoimmune thrombocytopenia. The autoimmune disease can also be temporal areritis, anti-phospholipid syndrome, vasculitides such as Wegener's granulomatosis and Behcet's disease. Other autoimmune diseases include polymyositis, drmatomyositis, spondyloarthropthies such as ankylosing spondylitis, anti-phospholipid syndrome, and polymyocysitis. In one specific, non-limiting example, the autoimmune disease is multiple sclerosis, such as relapsing remitting multiple sclerosis, primary progressive multiple sclerosis, secondary progressive multiple sclerosis, or clinically isolated syndrome.

In a specific, non-limiting example, the composition includes a therapeutically effective amount of a TCR CDR2 peptide.

Exemplary TCR CDR2 peptides include the amino acid sequences set forth in SEQ ID NOs: 1-116. The composition can include a single TCR CDR2 peptide or multiple TCR CDR2 peptides. For example, a composition can be administered a TCR CDR2 peptide including an amino acid sequence as set forth in SEQ ID NOs: 62, 73 or 90, or any combination thereof. The composition can include more than one isolated TCR CDR2 sequences, each including a different sequence (such as one of the sequences set forth as SEQ ID NOs: 1-116). Alternatively, a single TCR CDR2 peptide can include more than one of the sequences set forth as SEQ ID NOs: 1-116. One specific, but non-limiting example is a single peptide including SEQ ID NOs: 62, 73 and 90.

TCR peptides are well known in the art (see, e.g., U.S. Pat. No. 5,614,192 and U.S. Pat. No. 5,776,459, both of which are incorporated by reference herein in their entirety). TCR peptides are marketed under various trademarks such as NEUROVAX®. The TCR peptide can contain the complete V chain, or any immunogenic portion of the V region that is characteristic of the particular TCR V gene or gene family of interest. Such a peptide can have a sequence that is identical to that of the naturally occurring V chain. In one embodiment, a TCR V peptide includes one or more substitutions, such as a TCR V peptide that contains 1,2 or several substitutions that do not alter its specificity for the TCR V gene or gene family of interest.

Useful TCR V peptides will generally be from about 8 to about 100 amino acids in length, such as from about 10 to about 50 amino acids, including from about 15 to about 30 amino acids. TCR V peptides having any amino acids sequence of interest can be prepared by methods known in the art, including chemical synthesis and recombinant methods.

The CDR2 region, which corresponds to amino acids 38-58 of alpha (A) V and beta (B) V chains, is a region that is characteristic of each TCR V chain. The amino acid sequences of peptides corresponding to amino acids 38-58 of each of the 116 known AV and BV chains are known. Within a given family (e.g., BV6) or subfamily (e.g. BV6S1) of V chains, amino acids 38-58 generally differ at only one or several positions. Accordingly, if desired, a consensus CDR2 peptide can be prepared, which does not necessarily have the exact sequence of any naturally occurring V chain, but which stimulates T cells that are reactive against all members of the family or subfamily.

Appropriate TCR V peptides to use in the methods disclosed herein can be determined by those skilled in the art. Exemplary peptides are set forth in Table I (see the examples section). These peptides can be used alone or in combination. The immunogenicity of a given peptide can be predicted using well-known algorithms that predict T cell epitopes (see, e.g., Savoie et al., *Pac. Symp. Biocomput.* 1999:182-89, 1999; Cochlovius et al., *J. Immunol.* 165:4731-41, 2000). Both the immunogenicity and the specificity of a given peptide can be confirmed by standard immunological assays that measure in vivo or in vitro T cell responses (e.g., T cell proliferation assays, delayed type hypersensitivity assays, ELISA assays, ELISPOT assays and the like). In one example, BV5S2, BV6S5 and BV13S1 are utilized. However, other combinations of peptides can be utilized such as BVIOS1P, BV19S20, BV13S7, BV12S2A2T, BVIISIA1T, BV21SA1T, AV15S1, BV12S1A1N1, BV5S2, BV6S5 and BV13S1.

Additional agents can be administered to the subject. For example, a therapeutically effective amount of estrogen can be administered to the subject. The composition(s) can also include a therapeutically effective amount of an adjuvant, such as, but not limited to, complete Freund's adjuvant (CFA), incomplete Freund's adjuvant (IFA), immunomodulatory Oligonucleotides including Immunomers (Wang et al., Int J Oncol 2004, 24: 901-08.) and CpG oligodeoxynucleotides (Mosemann et al., J. Immunol. 173:4433, 2004), or IVX-908 (ID Biomedical of Canada). Further additional agents that can be administered to the subject include, for example, a therapeutically effective amount of: an interferon (such as IFN β1a or IFN β1b), an interleukin (such as IL-4), an antibody to an interleukin (such as anti-IL-12 or anti-IL-23), Glatiramer acetate (also known as Copolymer 1), Natalizumab, Mitoxantrone, and/or FTY720 (Novartis, Basil, Switzerland).

In one embodiment, an additional therapeutic agent is administered to the subject with an autoimmune disorder. These therapeutic agents can be administered at the same time, or at a different time (sequentially) as the agent that increases the expression of FOXP3. For example, if the subject has multiple sclerosis, an agent that increases the expression of FOXP3 can be administered in combination with other therapeutic agents. These agents include, but are not limited to, interferon-beta and antibodies that bind the IL-2 receptor. These agents can be included in a same composition as the agent that increases the expression of FOXP3, or can be administered in separate compositions.

Administration of a therapeutically effective amount of an agent that increases the expression of FOXP3 can be utilized whenever desired, for example, at the first sign of symptoms of an autoimmune disease, such as multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, or psoriasis, or at the first sign of symptoms of inflammation, such as pain, edema and elevated temperature.

Alternatively, administration of a therapeutically effective amount of an agent that increases the expression of FOXP3 can be done prophylactically (i.e., before any overt systems of autoimmune disease onset). In one non-limiting example, the agent is one or more TCR CDR2 peptide(s), alone or in combination with a therapeutically effective amount of IFA.

Therapeutically effective amounts of an agent that increases the expression of FOXP3 can be administered by a number of routes, including parenteral administration, for example, intravenous, intraperitoneal, intramuscular, intradermal, intrasternal, or intraarticular injection, or infusion. One of skill in the art can readily determine the appropriate route of administration. For example, a TCR CDR2 peptide and a therapeutically effective amount of IFA can be administered by injection.

The therapeutically effective amount of an agent that increases the expression of FOXP3, will be dependent on the subject being treated, the severity and type of the affliction, and the manner of administration. For example, a therapeutically effective amount of a TCR CDR2 peptide can vary from about 1-500 µg/injection. The exact amount of a TCR CDR2 peptide is readily determined by one of skill in the art based on the age, weight, sex, and physiological condition of the subject. Effective doses can be extrapolated from dose-response curves derived from in vitro or animal model test systems.

Generally, a therapeutically effective amount of an agent that increases FOXP3 expression, such as, but not limited to, one or more TCR CDR2 peptide(s), is that amount that achieves a desired effect in a subject being treated. For instance, this can be the amount of the agent that increases FOXP3 expression can be an amount that inhibits the advancement, or causes regression of an autoimmune disease, or which is capable of relieving symptoms caused by an autoimmune disease, such as pain and inflammation. The amount of the agent that increases FOXP3 expression administered to the subject can be the amount necessary to relieve symptoms associated with inflammation, such as pain, edema and elevated temperature. It can also be the amount necessary to diminish rejection of a transplanted organ. Similarly, if the agent is administered to a subject with multiple sclerosis, the amount can be an amount sufficient to show a therapeutic effect as evaluated by MRI of the subject.

The agent that increases the expression of FOXP3 can be administered in a pharmaceutically acceptable carrier, such as buffered saline or another medium suitable for administration to a subject. For example, one or more TCR peptides can be administered in a pharmaceutically acceptable carrier, such as a carrier formulated for injection. It should be noted that a single agent that increases the expression of FOXP3 can be administered, or multiple agents that increase the expression of FOXP3 can be administered to a subject of interest (such as a subject with an autoimmune disorder). In one specific, non-limiting example, estrogen is administered in conjunction with one or more TCR CDR2 peptides and an adjuvant, such as IFA.

In one embodiment, the agent that increases the expression of FOXP3 can be administered in conjunction with one or more additional pharmaceutical agents. The additional agents can be administered at the same time as the agent that increases the expression of FOXP3, or sequentially with the agent that increases the expression of FOXP3. In one non-limiting example, the agent is an additional immunosuppressive agent.

Such additional pharmaceutical agents can be administered before, during, or after administration of the agent that increases the expression of FOXP3, depending on the desired effect. This administration of the agent that increases the expression of FOXP3 and the additional agent can be by the same route or by different routes, and either at the same site or at a different site.

For administration at the same time, the additional agents can be formulated in the same composition that includes the agent increases the expression of FOXP3. For, example, that such as one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 and transforming growth factor-beta), hormones (for example, estrogen), or a vaccine.

For the treatment of a subject with multiple sclerosis, the agent that increases the expression of FOXP3 can be administered, for example, in combination with an antibody that binds the IL-2 receptor (such as DACLIZUMAB®) or interferon beta (such as with BETASERON®). In one example, on or more TCR CDR2 peptides that increase the expression of FOXP3 is administered in conjunction with an antibody that binds the IL-2 receptor or interferon beta. These agents can be administered as a single composition, or as two compositions (simultaneously or sequentially).

In a specific, non-limiting example, a therapeutically effective amount of estrogen is administered. The therapeutically effective amount of estrogen will be dependent on the subject being treated, the severity and type of the affliction, and the manner of administration. For example, a therapeutically effective amount of estrogen can vary from an amount sufficient to raise the serum concentration of the subject to about 10 pg/ml to an amount sufficient to raise the serum concentration of the subject to about 35,000 pg/ml, such as an amount sufficient to raise the serum concentration of the subject to about 100 pg/ml to an amount sufficient to raise the serum concentration of the subject to about 1,000 pg/ml, or an amount sufficient to raise the serum concentration of the subject to about 2,000 pg/ml to an amount sufficient to raise the serum concentration of the subject to about 3,000 pg/ml. The exact amount of estrogen is readily determined by one of skill in the art based on the age, weight, sex, and physiological condition of the subject (see, e.g., Published PCT Application No. WO 01/85154). Effective doses can be extrapolated from dose-response curves derived from in vitro or animal model test systems. Those skilled in the art can determine an appropriate time and duration of therapy to achieve the desired preventative or ameliorative effects on the immune pathology.

Estrogen can be prepared in any convenient form and administered by any convenient route known in the art. Estrogen can be administered orally, transdermally, subcutaneously, intravenously, intramuscularly, by a respiratory route (e.g., inhalation), intranasal, enteral, topical, sublingual, or rectal means. Estrogen can also be administered directly to the site of the pathology, for example into skin lesions, inflamed joints. For continuous release of defined concentrations of estrogen, administration via micropwnps, biopolymers, liposomes and other slow-release vehicles is advantageous.

In one specific, non-limiting example, estrogen can be administered with another agent that increases the expression of FOXP3, such as, but not limited to, one or more TCR CDR2 peptide and/or IFA. In this example, estrogen can be administered either before, at the same time, or after administration of a TCR CDR2 peptide and WA; either by the same route or by a different route, and either at the same site or at a different site. The administration of a TCR CDR2 peptide and WA can also be combined with administration of estrogen and an additional immunotherapeutic agent.

V. Method for Inducing Immunosuppression

Disclosed herein is a method for inducing immunosuppression. The method includes administering to a subject a therapeutically effective amount of a composition that increases FOXP3 expression, thereby inducing immunosuppression. Methods of administration of agents that increase FOXP3, and the administration of agents that increase the expression of FOXP3 in conjunction with other agents are disclosed above.

In a specific, non-limiting example, the method includes administering to a subject a therapeutically effective amount of a TCR CDR2 peptide and a therapeutically effective amount of IFA to induce immunosuppression. As discussed above, exemplary TCR CDR2 peptides include the amino acid sequences set forth in SEQ ID NOs: 1-116. In another specific example of the method, the composition further includes a therapeutically effective amount of estrogen. An adjuvant can optionally be included (see above). Generally, any of the compositions disclosed above to be of use in the methods of treating an autoimmune disorder can be used to treat inflammation and/or induce immunosupression.

Immunosuppression can be evaluated using many methods well known in the art. In one embodiment, a white blood cell count (WBC) is used to determine the responsiveness of a subject's immune system. A WBC measures the number of white blood cells in a subject. Using methods well known in the art, the white blood cells in a subject's blood sample are separated from other blood cells and counted. Normal values of white blood cells are about 4,500 to about 10,000 white blood cells/µl. Lower numbers of white blood cells can be indicative of a state of immunosuppression in the subject.

In another embodiment, immunosuppression in a subject may be determined using a T lymphocyte count. Using methods well known in the art, the white blood cells in a subject's blood sample are separated from other blood cells. T lymphocytes are differentiated from other white blood cells using standard methods in the art, such as, for example, immunofluorescence or FACS. Reduced numbers of T cells, or a specific population of T cells can be used as a measurement of immunosuppression. A reduction in the number of T-cells, or in a specific population of T cells, compared to the number of T cells (or the number of cells in the specific population) prior to treatment can be used to indicate that immunosuppression has been induced.

Immunosuppression can be induced in a subject has an autoimmune disease. Examples of an autoimmune disease include, but are not limited to, multiple sclerosis, rheumatoid arthritis, systemic lupus erythematosis, type I diabetes mellitus, Crohn's disease; myasthenia gravis, Grave's disease, scleroderma, Sjogren's syndrome, ulcerative colitis, primary biliary cirrhosis, autoimmune hepatitis, Hashimoto's thyroiditis, ankylosing spondylitis, and psoriasis. The autoimmune disease can be an autoimmune disease related to blood disorders such as autoimmune hemolytic anemia, pernicious anemia and autoimmune thrombocytopenia. The autoimmune disease can also be temporal areritis, anti-phospholipid syndrome, vasculitides such as Wegener's granulomatosis and Behcet's disease. Other autoimmune diseases include polymyositis, drmatomyositis, spondyloarthropthies such as ankylosing spondylitis, anti-phospholipid syndrome, and polymyocysitis. In another embodiment, the subject has graft-versus-host disease.

In yet another embodiment the subject is the recipient of a transplanted organ. Examples of a transplanted organ include kidney, liver, skin, or heart. A therapeutically effective amount of a TCR CDR2 peptide and a therapeutically effective amount of IFA can be administered prior to transplantation, concurrently with transplantation, or following transplantation.

In a further embodiment, administration of a therapeutically effective amount of an agent that increases the expression of FOXP3 to a subject treats or inhibits inflammation in the subject. IN one specific non-limiting example, the method includes administering a therapeutically effective amount of one or more TCR CDR2 peptide and a therapeutically effective amount of IFA to the subject to inhibit the inflammatory process.

Effective treatment or inhibition of inflammation can be measured by many methods known to those of skill in the art. For example, neutrophil infiltration at the site of inflammation can be measured. In order to assess neutrophil infiltration myeloperoxidase activity can be measured. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration, and can serve as a measure of inhibition of inflammation.

In another example, effective treatment or inhibition of inflammation in a subject can be assayed by measuring cytokine levels in the subject. Cytokine levels in body fluids or cell samples are determined by conventional methods. For example, an immunospot assay, such as the enzyme-linked immunospot or "ELISPOT" assay, as described herein, can be used.

VI. Diagnostic Methods and Method for Monitoring Treatment

It is disclosed herein that FOXP3 levels differ between subjects with an autoimmune disease and healthy controls (including, the FOXP3 gene, transcript and/or protein). Accordingly, it is now possible to use FOXP3 (whether the FOXP3 gene, transcript and/or protein) to detect an autoimmune disease or a predilection to an autoimmune disease in a subject, and/or to monitor the efficacy of autoimmune disease therapies. These methods can include determining whether the level of expression and/or activity of FOXP3 in one or more biological samples taken from a subject differ from each other or from another reference point. The reference point can be a standard value, or a control with a known amount of FOXP3 protein or mRNA. However, the reference point can also be another sample from the subject of interest. For example, prior to the onset of the therapy, a first sample is taken from the subject. Following onset of therapy, a second sample is taken from the subject. The expression of FOXP3 is evaluated in the first sample and in the second sample. If FOXP3 expression is increased in the second sample as compared to the first sample, the therapy is having the desired effect (and thus could be continued). However, if FOXP3 expression is decreased or remains the same in the first sample as compared to the second sample, then the therapy is not having the desired effect (and thus could be discontinued).

A biological sample that is useful in a disclosed method includes any part of the subject's body that can be obtained and reduced to a form that can be analyzed for the expression and/or activity of FOXP3 (e.g., gene, transcript, or protein). Typically, a biological sample will contain DNA, RNA and/or protein in amounts sufficient to conduct the desired analysis. Suitable biological samples include, for example, blood, or the components of blood, such as serum or isolated white blood cells. In one example, the expression of FOXP3 can be evaluated in CD4+ cells, such as CD4+CD25+ T cells. Thus, the method can include the isolation of CD4+ cells, such as CD4+CD25+ cells.

Biological samples can be obtained from normal, healthy subjects or from subjects who are predisposed to or who are suffering from any one of a variety of autoimmune diseases such as, but not limited to, multiple sclerosis, rheumatoid arthritis, systemic lupus erythematosis, type I diabetes mellitus, Crohn's disease; myasthenia gravis, Grave's disease, Hashimoto's thyroiditis, ankylosing spondylitis, and psoriasis. The disclosed methods contemplate as a subject any living organism capable of experiencing an autoimmune disease, including veterinary subjects (such as, felines, canines, rodents (e.g., mice and rats), equines, bovines, ovines, and the like) and human subjects (including, adults, adolescents, and children).

In one embodiment, at least two biological samples are obtained from a single subject over time, such as during a therapeutic regimen. In one non-limiting example, the samples are obtained form the same subject during the administration of a pulsatile doses of any therapeutic agent. The expression of FOXP3 is assessed in the first sample and the second sample. An increase in the expression of FOXP3 in the second sample as compared to the second sample indicates that the therapy is effective. A decrease of expression of FOXP3 in the second sample indicates that the therapy is ineffective.

A variety of therapies that are administered over a specified time period can be evaluated using the methods disclosed herein. In some embodiments, at least two biological samples are obtained from a single subject over time, such as during a therapeutic regimen. In one non-limiting example, the samples are obtained from the same subject during the administration of a low dose maintenance therapy. A lack of change in the expression of FOXP3 in the second sample as compared to the first sample indicates that the therapy is effective, and maintains desired clinical effect. A decrease in the expression of FOXP3 in the second sample as compared to the first sample indicates that the therapy is not effective, and indicates that the dose of the agent is insufficient or that a different therapeutic agent should be utilized in the subject. An increase in the level of FOXP3 indicates that either the therapeutic agent is effective and/or suggests that the dose of the therapeutic agent could be lowered to possibly achieve the desired effect.

The expression level and/or protein activity of FOXP3 can be detected in a disclosed method, including the expression of a transcript from, and/or expression or activity of a polypeptide encoded by, the FOXP3 gene. In particular examples, the expression of FOXP3 is determined by measuring mRNA levels (for example using a gene array, RT-PCR, quantitative PCR, in situ hybridization, Northern blot, or other method(s) commonly known in the art). In other examples, the expression of FOXP3 is determined by measuring the level or activity of FOXP3 protein (for example, using an antibody array, immunofluorescence, Western blot, radioimmunoassay, sandwich immunoassays (including ELISA), Western blot, affinity chromatography (affinity ligand bound to a solid phase), in situ detection with labeled antibodies, or any of a number of functional assays described herein).

In some disclosed methods, the upregulation or downregulation of FOXP3 can be detected, leading to a relative increase or decrease, respectively, in corresponding transcript and/or protein levels. In other disclosed methods, an increase or decrease in an activity of FOXP3 protein relative to a reference can be determined. Particular methods involve detecting a downregulation (and/or decrease in an activity) of FOXP3.

In certain method embodiments, an expression level (transcript or protein) and/or activity (protein) of FOXP3 is different with respect to a reference level of expression and/or activity of FOXP3. A variety of reference points can be used. In some instances, a reference point is the expression and/or activity of FOXP3 in a biological sample collected from a subject not suffering from an autoimmune disease (such as a control subject). In other examples, a reference point is an average (or "normal-range") value for the expression and/or activity of FOXP3 in subjects not suffering from an autoimmune disease, which normal-range value has been determined from population studies. In additional embodiments the control is a standard value, such as a sample with a known amount of FOXP3 mRNA or FOXP3 protein. In particular applications, such as some methods for determining the efficacy of an autoimmune disease therapy, a reference also can be, for example, the expression and/or activity of FOXP3 in a biological sample from the subject prior to onset of the therapy, and/or after some period of time following (or during) the therapy. Alternatively, the efficacy of an autoimmune disease therapy can be determined by comparing the expression and/or activity of FOXP3 in a test subject, who is receiving therapy, as compared to a second subject suffering from an autoimmune disease, who is receiving a placebo rather than therapy. In this latter situation, it is expected that the expression levels and/or activities of FOXP3 in the treated subject would diverge from those of a placebo-treated subject, with such expression levels and/or activities in an effectively treated subject approaching corresponding values observed in a healthy control subject.

In some disclosed methods, an expression level and/or activity of FOXP3 (e.g., gene, transcript or protein) can differ from a reference expression level and/or activity by at least ±10%; for example, by at least about ±15%, at least about 25%, at least about 40%, at least about ±50%, at least about ±60%, at least about ±75%, or at least about ±90%.

In the methods disclosed herein, FOXP3 expression levels are measured. A variety of methods can be used to detect and quantify FOXP3 expression by T cells. In some embodiments, FOXP3 mRNA is measured. FOXP3 mRNA can be measured by any method known to one of skill in the art. For example, polymerase chain reaction (PCR) can be used. Briefly, total RNA is extracted from T cells by any one of a variety of methods well known to those of ordinary skill in the art. Sambrook et al. (*In Molecular Cloning: A Laboratory Manual*, CSHL, New York, 1989) and Ausubel et al. (In *Current Protocols in Molecular Biology*, Greene Publ. Assoc. and Wiley-Intersciences, 1992) provide descriptions of methods for RNA isolation. The extracted RNA is then used as a template for performing reverse RT-PCR amplification of FOXP3 cDNA. FOXP3-specific primers for the PCR reaction can be obtained, for example, from Applied Biosystems (Foster City, Calif.). Methods and conditions for PCR are described in Kawasaki et al., (In *PCR Protocols, A Guide to Methods and Applications*, Innis et al. (eds.), 21-27, Academic Press, Inc., San Diego, Calif., 1990). In other examples, Northern blotting or RNA dot blots can also be used to detect FOXP3 mRNA.

An additional method for measuring FOXP3 expression levels utilizes measurements of FOXP3 protein. Antibodies to FOXP3 have been described (see for example, PCT Publication No. WO 02/090500 A2, which is incorporated herein by reference). These antibodies can be used in methods such as immunoassays (for example RIAs and ELISAs), immunohistochemistry, and Western blotting to assess the expression of FOXP3.

Briefly, for Western blotting, total cellular protein is extracted from T cells and electrophoresed on a sodium dodecyl sulfate-polyacrylamide gel. The proteins are then transferred to a membrane (for example, nitrocellulose or PVDF) by Western blotting, and an anti-FOXP3 antibody (e.g., a rabbit anti-human FOXP3 antibody) preparation is incubated with the membrane. After washing the membrane to remove non-specifically bound antibodies, the presence of specifically bound antibodies is detected by the use of (by way of example) an anti-rabbit antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase.

One method embodiment for detecting or diagnosing in a subject an autoimmune disease or a predisposition to an autoimmune disease, involves (a) determining the expression and/or activity of FOXP3 (e.g., gene, transcript and/or protein) in a biological sample from a subject; and (b) comparing the expression and/or activity of the FOXP3 in the biological sample to the expression and/or activity of the FOXP3 in a reference sample, wherein a difference in the expression and/or activity of the FOXP3 in the biological sample and the reference sample detects or diagnoses in the subject an autoimmune disease or a predisposition to an autoimmune disease.

In another method embodiment, the efficacy of an autoimmune disease therapy can be determined by (a) obtaining a first biological sample from a first subject suffering from an autoimmune disease; (b) treating the first subject with a candidate therapy; (c) obtaining a second biological sample from at least one of the following: (i) the first subject following treatment; (ii) an individual not suffering from an autoimmune disease; or (iii) a second subject suffering from an autoimmune disease receiving a placebo rather than therapy; and (d) comparing the expression and/or activity of FOXP3 in the first and second biological samples, wherein a change in the expression and/or activity of FOXP3 indicates that the candidate therapy is effective at treating the autoimmune disease in the first subject. In other methods, steps (a)-(d) can be repeated on the first subject after altering the dose or dosing regimen of the candidate therapy.

In more specific embodiments, a method for monitoring an outcome of an autoimmune disease therapy in a subject, involves (a) obtaining a first biological sample from a subject suffering from an autoimmune disease; (b) treating the subject with an autoimmune disease therapy; (c) obtaining a second biological sample from the subject following a period of treatment with the autoimmune disease therapy; and (d) comparing the expression and/or activity of FOXP3 in the first and second biological samples, wherein a relative change in the expression and/or activity of FOXP3 in the first and second biological sample monitors an outcome of the candidate therapy.

In some embodiments, the sample is a histological sample. In other embodiments, the sample is a biological fluid, such as blood, serum, sputum, pleural fluid, or spinal fluid. In additional embodiments, the cells are isolated from the sample prior to performing the assay. For example, T cells are isolated from the sample. The T cells can be any T cells of interest, such as, but not limited to, CD3+, CD4+, and/or CD25+ T cells. In one specific non-limiting example, CD4+ CD25+ T cells can be isolated, and the expression of FOXP3 can be assessed in the CD4+CD25+ T cells.

Methods for the isolation and quantitation of T cells, such as CD4+, CD4+CD25+, and CD4+CD25− T cells, are well known in the art. Typically, labeled antibodies specifically directed to one or more cell surface markers are used to identify and quantify the T cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate (FITC), tetramethylrhodamine isothiocyanate, phycoerythrin (PE), allophycocyanins and Texas Red. For additional fluorochromes that can be conjugated to antibodies see Haugland, R. P., *Handbook of Fluorescent Probes and Research Products*, published by Molecular Probes, 9$^{th}$ Edition (2002). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated to or incorporated into the antibodies are known to the art, and include, but are not limited to, technetium 99 ($^{99}$Tc), $^{125}$I, and amino acids comprising any radionuclides, including, but not limited to, $^{14}$C, $^{3}$H and $^{35}$S.

Fluorescence activated cell sorting (FACS) can be used to sort cells that are CD4+, CD25+, or both CD4+ and CD25+, by contacting the cells with an appropriately labeled antibody. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic Petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well known in the art.

Unbound cells then can be eluted or washed away with physiologic buffer after sufficient time has been allowed for the cells expressing a marker of interest (e.g., CD4 and/or CD25) to bind to the solid-phase linked antibodies. The bound cells are then separated from the solid phase by any appropriate method, depending mainly upon the nature of the solid phase and the antibody employed, and quantified using methods well known in the art. In one specific, non-limiting example, bound cells separated from the solid phase are quantified by FACS.

Antibodies may be conjugated to biotin, which then can be removed with avidin or streptavidin bound to a support, or fluorochromes, which can be used with FACS to enable cell separation and quantitation, as known in the art.

In additional embodiments, cytokine expression levels in the biological sample of interest are also measured. A variety of methods can be used to detect and quantify cytokine expression by T-cells. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well known in the art and are described, for example, in Czerkinsky et al., *J. Immunol. Methods* 110:29-36, 1988; Olsson et al. *J. Clin. Invest.* 86:981-985, 1990; and EP 957359.

Briefly, the immunospot assay uses microtiter plates containing membranes that are precoated with a capture agent, such as an anti-cytokine antibody, specific for the cytokine to be detected. T cells of interest are plated together with a composition (e.g., a therapeutically effective amount of a TCR CDR2 peptide and a therapeutically effective amount of WA). The T cells that respond to the composition secrete various cytokines. As a cytokine to be quantified is locally released by the T cells, it is captured by the membrane-bound antibody. After a suitable period of time the cell culture is terminated, the T cells are removed and the plate-bound cytokine is visualized by an appropriate detection system. Each cytokine-secreting T cell will ideally be represented as a detectable spot. The number of spots, and thus the number of T cells secreting the particular cytokine of interest, can be counted manually (for example, by visualization via light microscopy) or by using an automated scanning system (for example, an Immunospot Reader from Cellular Technology Ltd., Cleveland, Ohio).

Variations of the standard immunospot assay are well known in the art and can be used to detect alterations in cytokine production in the methods of the disclosure. For example, U.S. Pat. No. 5,939,281 describes an improved immunospot assay that uses a hydrophobic membrane instead of the conventional nitrocellulose membrane, to bind the cytokine capture reagent. This variation can be used to reduce the non-specific background and increase the sensitivity of the assay. Other modifications to the standard immunospot assay that increase the speed of processing multiple samples, decrease the amount of reagents and T cells needed in the assay, or increase the sensitivity or reliability of the assay, are contemplated herein and can be determined by those skilled in the art.

U.S. Pat. No. 6,218,132 describes a modified immunospot assay in which T cells are allowed to proliferate in response to stimulation before detection of the cytokine of interest. This method, although more time-consuming, can be used to increase the sensitivity of the assay for detecting T cells present at a low frequency in the starting population.

Antibodies suitable for use in immunospot assays, which are specific for secreted cytokines, as well as detection reagents and automated detection systems, are well known in the art and generally are commercially available. Appropriate detection reagents are also well known in the art and commercially available, and include, for example, secondary antibodies conjugated to fluorochromes, colored beads, and enzymes whose substrates can be converted to colored products (for example, horseradish peroxidase and alkaline phosphatase). Other suitable detection reagents include secondary agents conjugated to ligands (for example, biotin) that can be detected with a tertiary reagent (for example, streptavidin) that is detectably labeled as above.

Other methods for detecting and quantifying cytokine expression are well known in the art, and can be used as an alternative to immunospot assays. Such methods include the enzyme-linked immunoabsorbent assay (ELISA), which can be used to measure the amount of cytokine secreted by T cells into a supernatant (see, e.g., Vandenbark et al., Nature Med. 2:1109-1115, 1996). Alternatively, the expression of cytokine mRNA can be determined by standard immunological methods, which include reverse transcriptase polymerase chain reaction (RT-PCR) and in-situ hybridization.

In the methods disclosed herein, suppression of cell proliferation by T cells from the sample of interest can also be measured. Suppression of proliferation can be evaluated using many methods well known in the art. In one embodiment, cell proliferation is quantified by measuring $[^3H]$-thymidine incorporation. Proliferating cells incorporate the labeled DNA precursor into newly synthesized DNA, such that the amount of incorporation, measured by liquid scintillation counting, is a relative measure of cellular proliferation. In another embodiment, cell proliferation is quantified using the thymidine analogue 5-bromo-2'-deoxyuridine (BrdU) in a proliferation assay. BrdU is incorporated into cellular DNA in a manner similar to thymidine, and is quantified using anti-BrdU mAbs in an ELISA.

In a further embodiment, cell proliferation may be determined based upon the reduction of the tetrazolium salt 3,[4, 5-dimethylthiazol-2-yl]-2,5-diphenyltetrazolium bromide (MTT). The tetrazolium ring of MTT is reduced to formazan, which is blue in color, by the succinate-tetrazolium reductase system active only in viable cells. The intensity of the resulting color change indicates the enzymatic activity of living cells. In actively proliferating cells, MTT conversion increases, whereas in senescent and dying cells, the rate of MTT conversion slows. Comparison of this value to an untreated control provides a measure of the change in cellular proliferation.

The subject matter of the present disclosure is further illustrated by the following non-limiting Examples.

EXAMPLES

Example 1

E2 Augments Foxp3 Expression in vitro

The capacity of E2 to induce Foxp3 expression in vitro in purified (>99%) CD4+CD25− T cells was tested. E2 in combination with TCR stimulation by anti-CD3 antibody for 24 hours induced Foxp3 mRNA approximately 3-fold over levels in untreated cells, while TCR stimulation with anti-CD3 without E2, failed to induce Foxp3 (FIG. 1). In addition, E2 increased the fraction of CD25+ cells over TCR stimulation alone, consistent with induction of Treg.

Example 2

E2 Treatment Before EAE Induction Augments Foxp3 Expression In Vivo

Mice

Female naïve or syngeneic pregnant (19 days) C57BL/6 mice were purchased from Jackson Laboratory (Bar Harbor, Me.). Estrogen receptor alpha knockout (Esr1$^{-/-}$) mice were purchased from Taconic (Germantown, N.Y.). Most experiments represent cells pooled from at least five mice per experimental condition.

Hormone Treatment

For E2 therapy, a 3 mm pellet containing 2.5 mg or 15 mg (as indicated) 17β-estradiol (Innovative Research of America, Sarasota, Fla.) was implanted s.c. (dorsally) 7 days prior to immunization (EAE) or 14 days prior to analysis of naïve mice. These pellets are designed to release their contents at a constant rate over 60 days. Control animals were implanted with pellets containing saline. Serum levels of E2 were monitored by RIA.

Induction of EAE

Briefly, mice were immunized s.c. in the flanks with 200 µg MOG-35-55 peptide in CFA (Difco Laboratories, Detroit, Mich.). Mice were also given pertussis toxin i.p on days 0 (75 ng) and 2 (200 ng).

E2 Treatment Before EAE Induction Augments Foxp3 Expression in vivo

Figure 2:
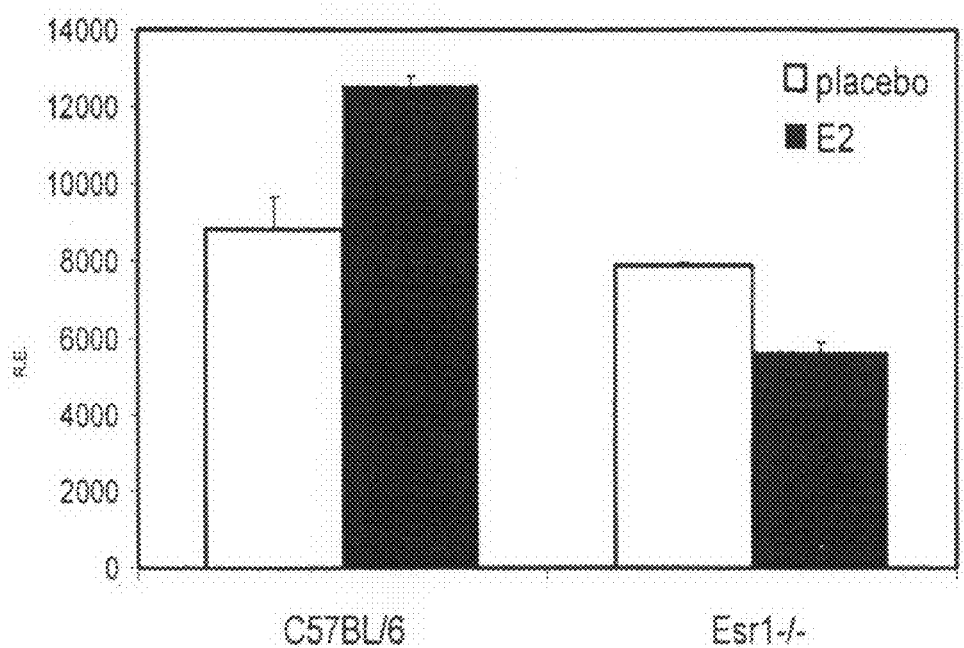
FIG. 2 is a graph illustrating real-time RT-PCR analysis of Foxp3. C57BL/6 and Esr$^{-/-}$ mice were implanted with placebo or 2.5 mg E2 pellets and immunized 1 week later with 200 µg MOG-35-55 peptide in CFA with pertussis toxin on days 0 and +2. At the peak of clinical disease, mice were sacrificed and splenocytes sorted for CD4+ cells. cDNA was prepared and analyzed by real-time PCR to determine Foxp3 mRNA levels. Data are presented as Foxp3 relative to housekeeping gene L32. Error bars are standard deviation of triplicate samples.
Figure 3:
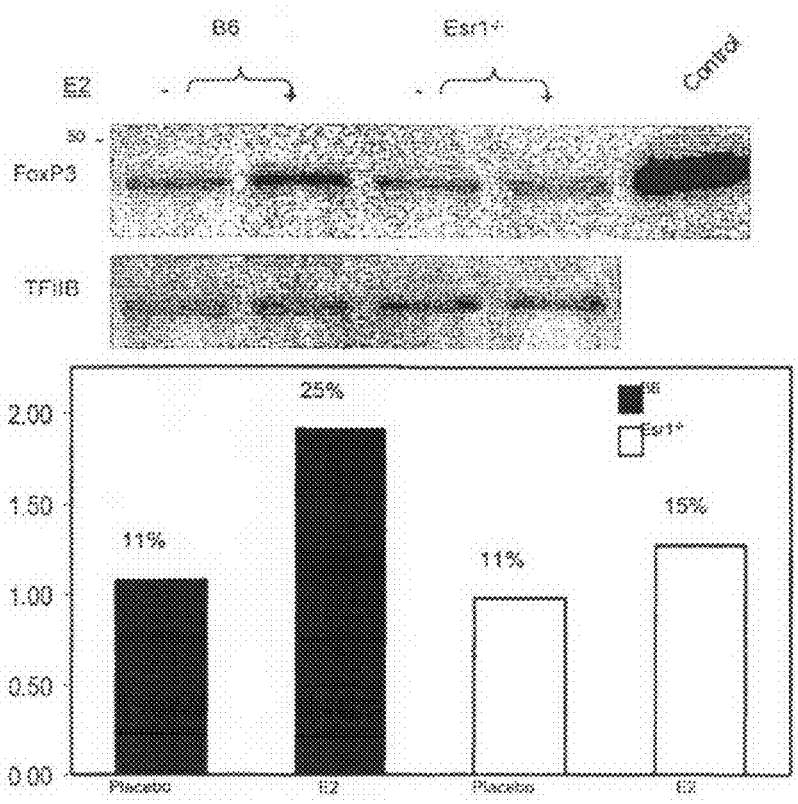
FIG. 3 shows Foxp3 western blot analysis of samples from FIG. 2. Densitometry shows Foxp3 expression level relative to the loading control TFIIB. Control lane is lysate of 293T cells transfected with Foxp3 cDNA. The CD25+ fraction (among CD4+) of each sample is noted above bars.

To determine if the ability of E2 to protect mice from EAE correlates with an effect on the Treg compartment, Foxp3 expression levels in the presence or absence of E2 treatment were analyzed at the peak of disease. Therapeutic doses of E2 significantly increased Foxp3 mRNA levels in CD4+ T cells from MOG-35-55 peptide-immunized wild-type C57BL/6 mice that were protected from EAE, but not in CD4+ T cells from Esr1$^{-/-}$ mice lacking estrogen receptor-a that developed severe signs of EAE (FIG. 2). In addition, FoxP3 protein expression and CD25+ number in E2-treated mice were substantially lower in Esr1$^{-/-}$ than in wild-type animals (FIG. 3), indicating a deficient expansion of Treg in the absence of normal E2 responsiveness. Changes in FoxP3 protein level correlated well with changes in CD25+ number in response to E2 by each genotype (FIG. 3).

Example 3

E2 Expands the Treg Compartment in vivo

Cell Preparation and Culture

Single-cell suspensions were prepared from spleens and RBCs lysed. Non-immunized mice receiving E2 pellets were sacrificed 14 days after implantation, while immunized mice were sacrificed at the peak of EAE disease severity, approximately 17 days after induction. Purified CD4+ cells were obtained by magnetically activated cell sorting (MACS) according to manufacturer's protocols (Miltenyi Biotec, Bergisch Gladbach, Germany). For flow cytometry, cells were stained with FITC-anti-CD4 and PE-anti-CD25 (BD PharMingen, San Diego, Calif.). CD4+CD25− cells were obtained from purified CD4+ using a FACSVantage (BD Immunocytornetry Systems, San Jose, Calif.). For in vitro experiments, CD4+CD25− cells were stimulated with 5 µg/ml anti-CD3ε and 1 µg/ml anti-CD28 (145-2C11 and 37.51, respectively, BD PharMingen). In some experiments, cells were treated with E2 alone in the absence of antibody stimulation.

Evaluation of Foxp3 Expression

For real-time RT-PCR analysis, total RNA was prepared using the Total RNeasy kit (Qiagen, Germantown, Md.) and cDNA was prepared using random hexamer primers (Invitrogen, Grand Island, N.Y.). Foxp3 message expression was quantified using the ABI 7000 Real-Time PCR System (Applied Biosystems, Foster City, Calif.). Amplification was performed in a total volume of 25 µl for 40 cycles and products were detected using SYBR Green I dye (Molecular Probes, Eugene, Oreg.). Samples were run in triplicate and relative expression level was determined by normalization to L32 with results presented as relative expression (RE) units. Primer sequences used were as follows: L32, forward: GGA AAC CCA GAG GCA TTG AC (SEQ ID NO: 117), reverse: TCA GGA TCT GGC CCT TGA AC (SEQ ID NO: 118); Foxp3, forward: GGC CCT TCT CCA GGA CAG A (SEQ ID NO: 119), reverse: GCT GAT CAT GGC TGG GTT GT (SEQ ID NO: 120). For analysis of FoxP3 protein, cells were washed in PBS then lysed and sonicated in lysis buffer {25 mM Tris pH 8.5, 2% lithium dodecyl sulfate, 1 mM EDTA, 10 mM sodium fluoride, 1 mM sodium orthovanadate, and 1× Complete protease inhibitors (Roche Diagnostics, Mannheim, Germany)} and quantified by BCA (Pierce, Rockford, Ill.). Lysates were separated on 4-12% gradient bis-tris gels (Invitrogen, Carlsbad, Calif.) and transferred to nitrocellulose (GE Osmonics, Minnetonka, Minn.) followed by blocking in TBS/0.1% Tween-20 with 5% nonfat dry milk. FoxP3 was detected with rabbit-anti-FoxP3 antiserum and standard chemiluminescence. For loading control, blots were stripped and re-probed for TFIIB (Santa Cruz, Santa Cruz, Calif.). Positive control lysate was from 293T cells transfected with FoxP3 cDNA. Films were analyzed by volumetric pixel integration using ImageQuant v5.2 (Amersham Biosciences, Uppsala, Sweden).

E2 Expands the Treg Compartment In Vivo

Figure 4:
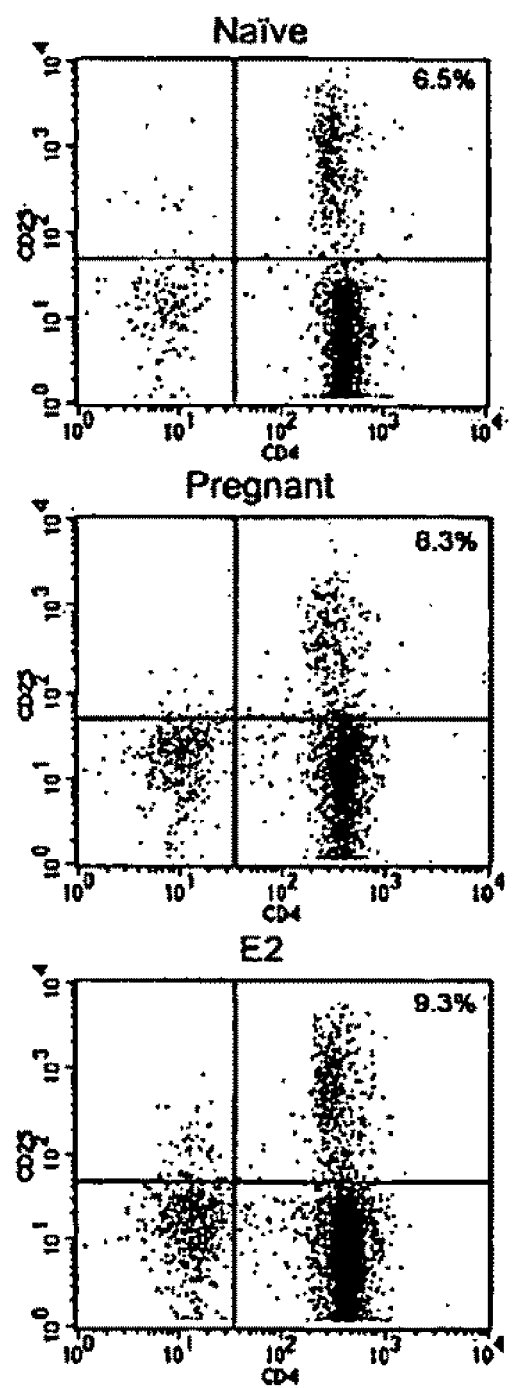
FIG. 4 shows Flow cytometric analysis comparing CD4+ CD25+ populations in naïve (nulliparous), 19 day pregnant and 14 day E2-treated mice. Quadrant statistics noted are percent of live gate.

Many of the surface markers for Treg (such as CD25 and GITR) are also markers of activated effector CD4+ T cells. In order to avoid a significant contribution of activated T cells to the analysis of the Treg compartment (as in MOG-immunized animals), naïve C57B1J6 mice were treated with E2 for 14 days and CD25 and FoxP3 expression were assessed among CD4+ T cells. A significant increase (43%) in the fraction of CD25+ cells among all CD4+ cells in E2-treated versus untreated mice was observed (FIG. 4). This increase in CD25+ cells was attended by an increase in Foxp3 mRNA (FIG. 5) and protein (FIG. 6), indicating that the cells generated are Treg and not activated effector CD4+ cells.

Figure 7:
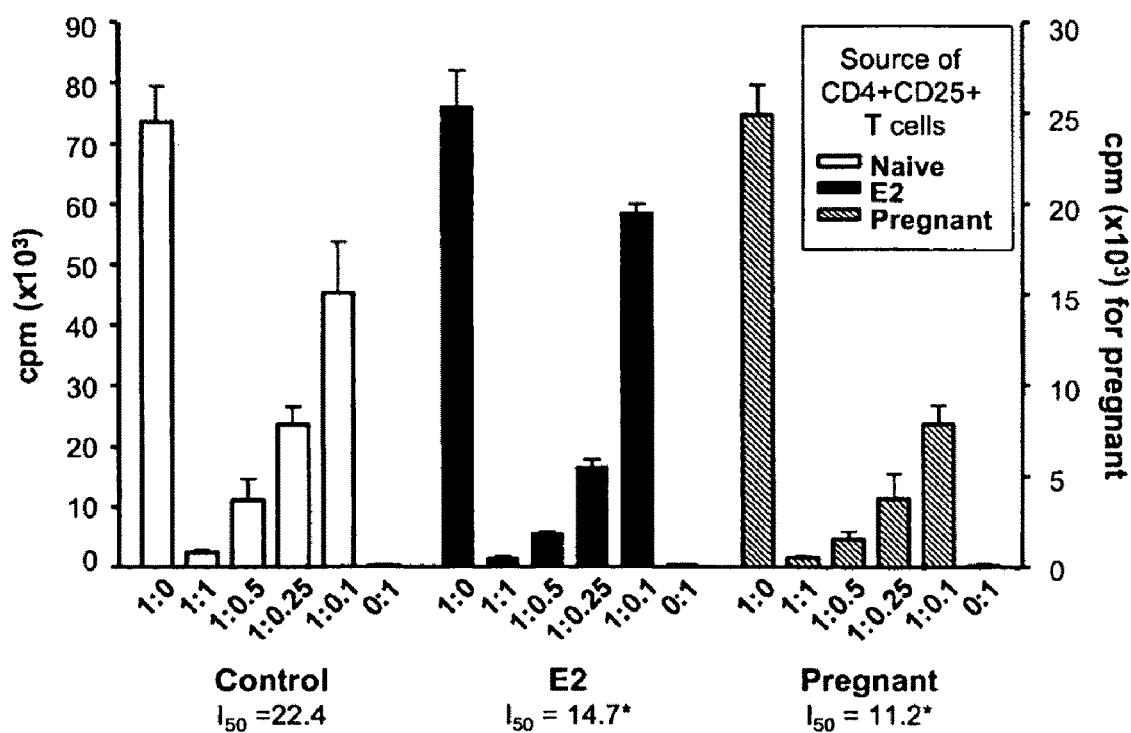
FIG. 7 illustrates the suppressive activity of CD4+CD25+ T cells recovered from placebo, E2-treated and pregnant mice was measured by their ability to suppress the growth of CD4+ CD25−responder cells. Varying numbers of sorted CD4+ CD25+ Treg cells from placebo-treated, E2-treated, and pregnant mice were co-cultured in triplicate for 3 days without (0:1 ratio) or with a constant number ($5\times10^4$) of CD4+CD25− responder cells and APC ($10^5$) from naïve donors, and 0.5 µg/ml anti-CD3 mAb. Responder cells were also cultured alone (1:0 ratio). Proliferation was monitored by uptake of [$^3$H]-thymidine (1 µCi/well) for the last 12 h of culture. Data are representative of three independent experiments. *$I_{50}$ values (% CD4+CD25+ cells that could inhibit the proliferation of anti-CD3-activated CD4+CD25−responder cells by 50%) represent the average of two or more independent experiments.
Figure 8:
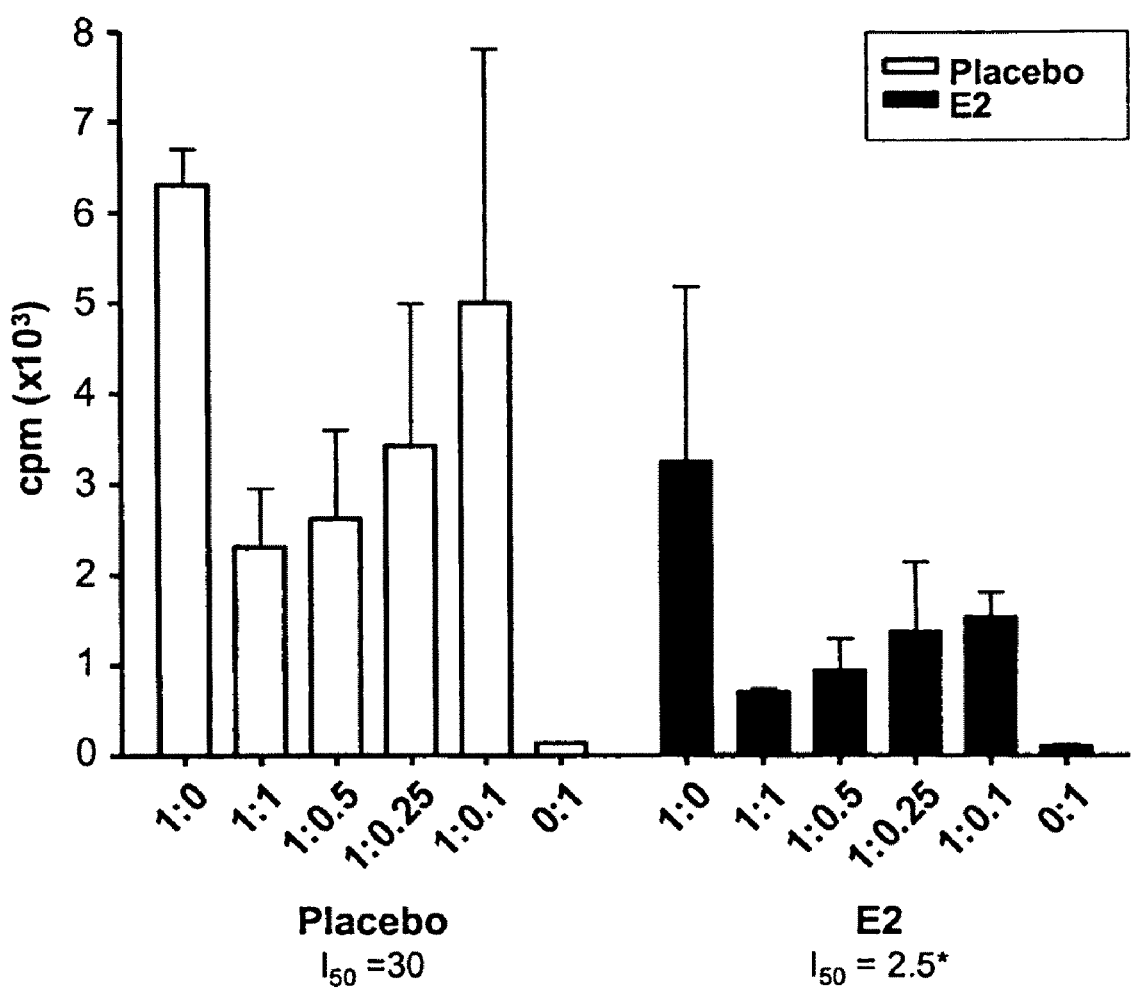
FIG. 8 shows an evaluation of Treg suppressive activity in E2-protected vs. placebo-treated mice with EAE. Female C57BL/6 mice were pretreated with 17β-estradiol (E2) or placebo for 7 days prior to challenge with MOG-35-55 peptide/CFA/PM to induce EAE. At the peak of EAE in the placebo group (day 15 after induction), cells were harvested from both the placebo-treated mice (score=4.5-5) and E2-treated mice (score=0). Cell mixtures were combined within each treatment group. Five$\times10^4$ CD4+CD25− responder cells in combination with $5\times10^4$ APC and the indicated ratios of CD4+CD25+ suppressor cells were stimulated in triplicate wells with anti-CD3 mAb for 3 days, with addition of [$^3$H]-thymidine for the last 12 h of culture. Representative data from two independent experiments are shown. Treg cells from E2 pretreated donors showed greater suppressive activity than Treg cells from placebo controls, as determined by $I_{50}$. *=significance difference ($p<0.05$) between E2-pretreated and placebo-pretreated groups, as determined by Student's t test.

As is shown in FIG. 7, the average $I_{50}$ value for CD4+ CD25+ Treg cells isolated from E2-treated mice was significantly lower than for Treg isolated from naïve mice, (14.7±0.3% vs 22.4±3.1% respectively, n=3 experiments, p<0.05), indicting increased suppression. Similarly, the average $I_{50}$ values for CD4+CD25+ Treg cells from pregnant mice tested on gestational days 7-14 were also significantly lower than from control mice (11.2±2.0% vs. 22.4±3.1% respectively, FIG. 7, p<0.05). As is shown in FIG. 8, Treg suppressive activity in E2-protected mice was strikingly enhanced ($I_{50}$=2.5%) versus control mice with EAE ($I_{50}$=30%).

Figure 5:
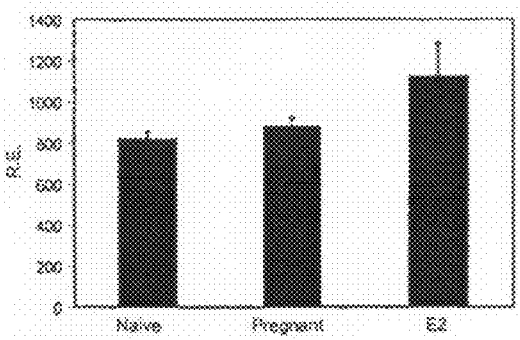
FIG. 5 is a graph illustrating real-time PCR analysis of Foxp3 mRNA in CD4+ cells from FIG. 4. Data are presented as Foxp3 relative to housekeeping gene L32. Error bars are standard deviation of triplicate samples.
Figure 6:
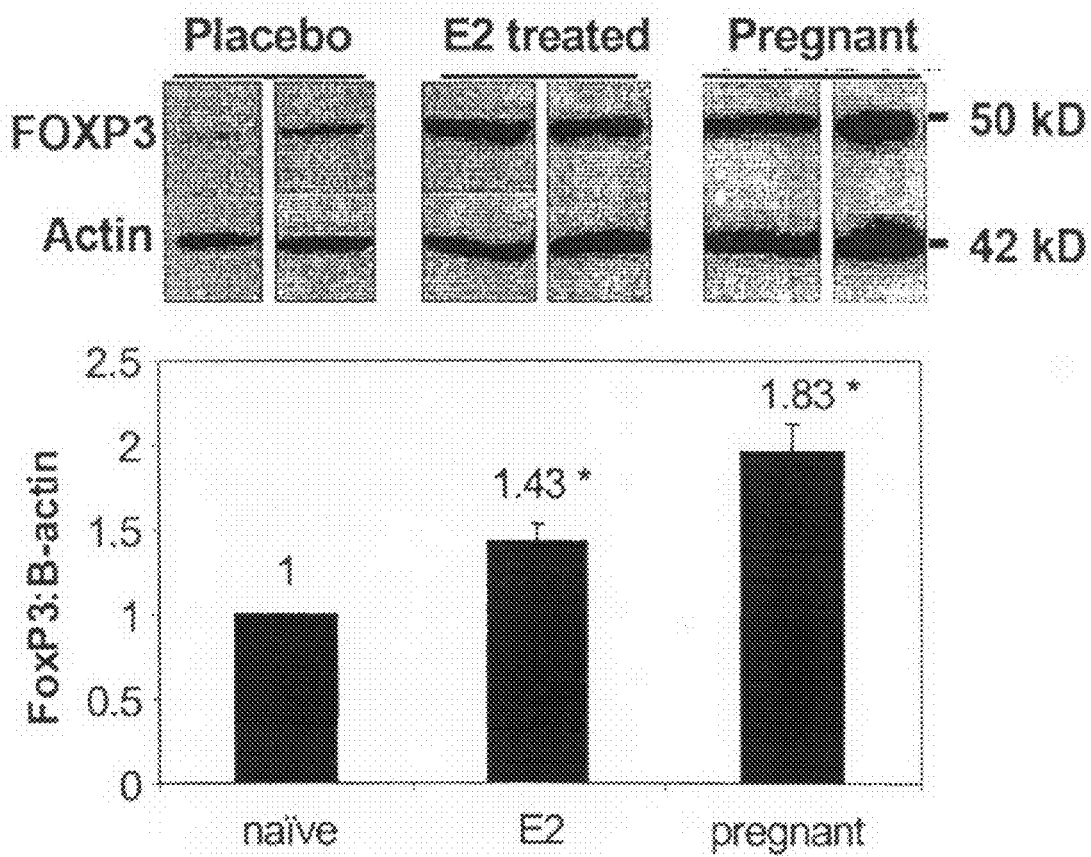
FIG. 6 shows FoxP3 versus β-actin Western blot analyses of FACS sorted CD4+CD25+ T cells isolated from the spleens of placebo, E2-treated, and pregnant mice. Cells were pooled from 8-10 mice before sorting. Figure shows blots from cells collected in two of eight separate experiments. Densitometry shows fold induction of FoxP3:β-actin ratio in E2-treated or pregnant mice relative to placebo mice. *=significant difference in ratios determined using Student's t test ($p<0.05$).

Pregnancy represents a natural instance of sustained high levels of estrogen, as well as a challenge to peripheral tolerance since the fetus bears paternal and alloantigens that can be presented to maternal T cells. It has been reported that pregnancy in humans is attended by an increase in CD4+CD25+ numbers, potentially Treg, yet the signal for this increase is unknown. CD4+ T cells from pregnant (19 days) C57BL/6 mice were examined for expression of CD25, Foxp3 mRNA, and FoxP3 protein. There were significant increases in both the fraction of CD25+ cells (28%, FIG. 4) and the level of FoxP3 protein (FIG. 6). However, there was no significant difference in Foxp3 mRNA level between naïve and pregnant mouse CD4+ T cells (FIG. 5).

Example 4

Expression of FOXP3 in Multiple Sclerosis Patients

Subjects

Blood was obtained by venipuncture from nineteen HC donors (15 females and 4 males, age 22-61 years, mean 40 years) and nineteen MS patients (16 females and 3 males, age 23-61 years, mean 47 years) with relapsing-remitting (n=11), primary progressive (n=1), or secondary progressive (n=7) MS (disease duration of 15.3 years) enrolled in an ongoing open label clinical trial. The MS patients were not receiving any treatments at the time of sampling, having concluded a >3 month washout period from previous therapies.

Isolation of T Cell Subpopulations Using Magnetic Beads

Blood was collected into heparinized tubes and mononuclear cells separated by Ficoll density centrifugation. The indicator (CD4+CD25−) and suppressor (CD4+CD25+) cells were isolated from 70 million PBMC using the Miltenyi magnetic bead separation protocol. These cells were first incubated with the Miltenyi CD4+ No Touch T Cell kit containing antibodies that remove non-CD4+ cells, including CD8+ and γδ+ T cells, B cells NK cells, monocytes, dendritic cells, granulocytes, platelets, and erythroid cells. The CD4+ cells were then separated using anti-CD25 mAb conjugated magnetic beads into the CD25+ suppressor T cell fraction (>90% pure) and the remaining CD25− fraction that are used as indicator cells.

Real-Time Polymerase Chain Reaction

T cell subpopulations were analyzed for FOXP3 expression using real-time PCR. Briefly, total RNA was isolated from frozen cell pellets using the Total RNeasy kit (Qiagen, Germantown, Md.). RNA was DNase-treated using Turbo-DNA free (Ambion, Austin, Tex.) and cDNA was synthesized in a 20 uL volume using Superscript II reverse transcriptase (Life Technologies, Gaithersburg, Md.) and random primers (Invitrogen, Grand Island, N.Y.) following manufacturer's recommendations. FOXP3 message expression was determined by the TaqMan method of real-time PCR, using HPRT1 as an endogenous control. TaqMan Universal PCR Master Mix, and both the FOXP3 primer/probe sets and the HPRT1 primer/probe sets were purchased from Applied Biosystems (Foster City, Calif.). HPRT1 was chosen as an endogenous control after comparing several different housekeeping genes (e.g., 18sRNA, PGK1, GAPDH, HPRT1) with the goal of finding one which did not vary with the type of sorted cell population, or the culture conditions used.

Western Blot Analysis

Sorted cells were lysed in lysis buffer (25 mM Tris-Cl pH8.8, 1 mM EDTA and 2% SDS) and analyzed by Western blotting with 10% SDS-PAGE gels. Rabbit anti-human FOXP3 antibody (1:1000) (Dr. Ziegler, Benaroya Research Institute, Seattle, Wash.) and goat anti-rabbit IgG HRP-conjugated antibody (1:20,000) (Pierce, Rockford, Ill.) and the enhanced ECL system (Amersham, Arlington Heights, Ill.) were used for the detection of FOXP3 protein. Actin was subsequently detected with mouse anti-actin antibody (1:1000) (Chemicon, Temecula, Calif.) and goat anti-mouse IgG HRP-conjugated antibody (1:20,000) (Pierce, Rockford, Ill.) as an internal control.

Treg Suppression Assay Using Bead-Sorted Cells

All suppression assays were performed in 96-well round bottom plates (Becton Dickinson, Franklin Lakes, N.J.) in a final volume of 200 µl/well of 1% type AB human serum complete media (Bio Whittaker, Walkersville, Md.). Prior to assay setup, 18 wells each in the 96 well plates were coated with 100 µl of a final concentration of 2.0 µg/ml anti-CD3+ anti-CD28 mAbs, or 1.0, 0.5, and 0.1 µg/ml anti-CD3 mAb only (Caltag Labs, Burlingame, Calif.), and the plates were incubated overnight at 4° C. All wells were washed before assay setup. The CD4+CD25− cells were plated at $2.0 \times 10^4$/well alone or in combination with CD4+CD25+ cells in triplicate at $0.4 \times 10^4$, $1.2 \times 10^4$, $2.0 \times 10^4$, and $4.0 \times 10^4$/well, and the CD4+CD25+ cells were cultured alone at $2.0 \times 10^4$/well. Thus the cells were co-cultured at the following ratios of: 1:0, 1:0.1, 1:0.3, 1:1, 1:2, and 0:1. To the wells containing 1.0, 0.5, and 0.1 µg/ml plate bound anti-CD3 mAb, 5 µg/ml anti-CD28 mAb and $1.0 \times 10^4$ irradiated (2,500Rads) PBMC were added as APC. On day 5, 0.5 µCi of $^3$H-thymidine (NEN, Boston, Mass.) was added to each well for the final 16 hours of culture. The cells were then harvested on glass fiber filters and assessed for uptake of the labeled thymidine by liquid scintillation. Percent suppression was determined at each mixed cell ratio compared to responses of CD4+CD25+ (suppressor cells) and CD4+CD25− T cells (indicator T cells) alone as follows:

$$\frac{\text{Mean } cpm(\text{indicator cells}) - \text{mean } cpm(\text{mixed cell culture})}{\text{mean } cpm(\text{indicator cells}) - \text{mean } cpm(\text{suppressor cells})}$$

The percent suppression was plotted versus increasing percentage of suppressor:indicator cells and a regression line was calculated. $I_{50}$ values were determined as the ratio of suppressor:indicator cells that produced 50% suppression.

Statistical Analyses

Spearman rank-order correlation was used to test the correlation between paired samples of FOXP3 message and FOXP3 protein, FOXP3 message and $I_{50}$, and FOXP3 protein and $I_{50}$. A t-test was used to test the significance of the difference between the mean FOXP3 protein in HC and MS, between FOXP3 message in HC and MS, and between average $I_{50}$ values in HC and MS for each concentration of anti-CD3.

Decreased FOXP3 Expression in Multiple Sclerosis Patients

Figure 9:
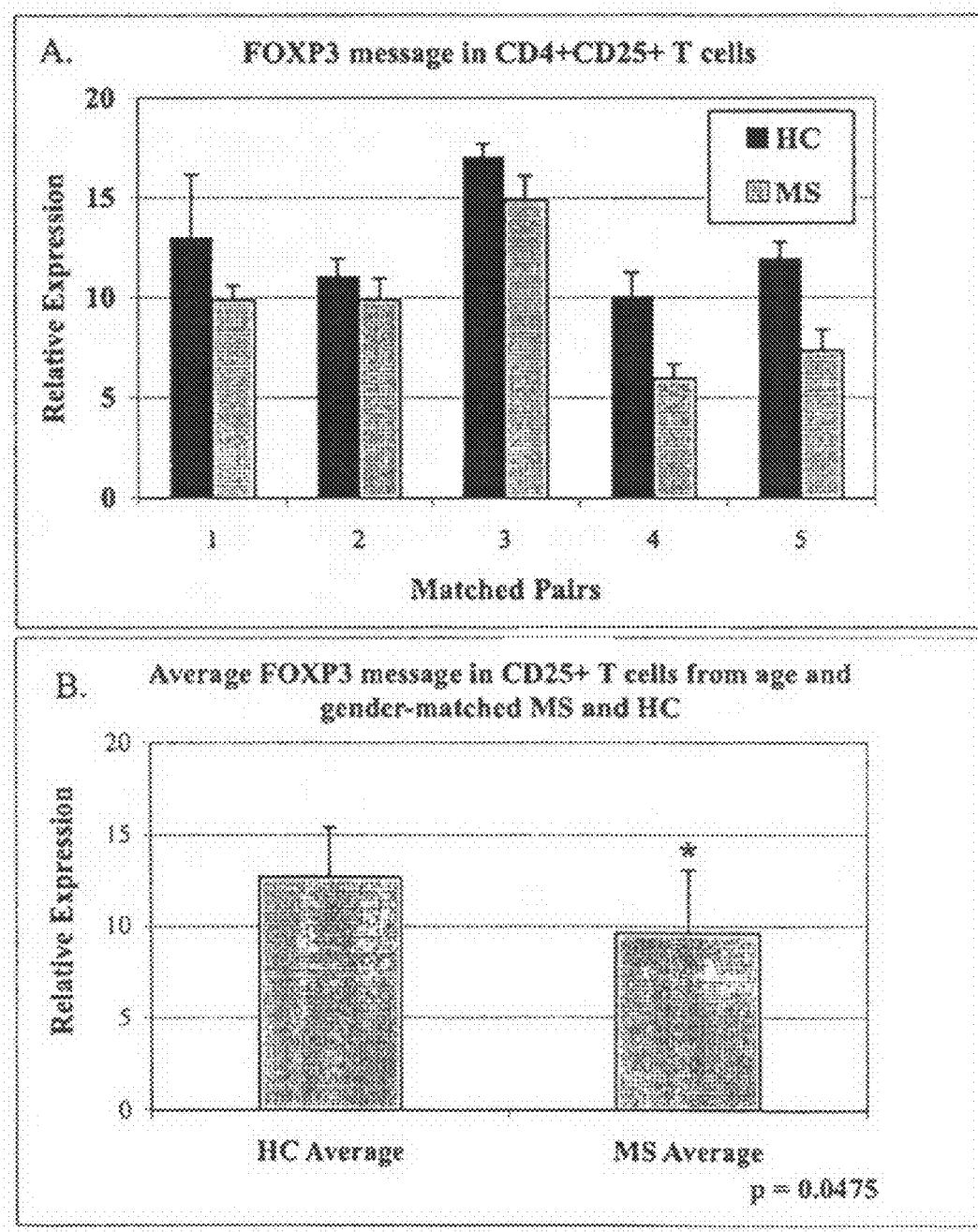
FIGS. 9A-9B are a pair of graphs illustrating FOXP3 message in CD4+CD25+ T cells from MS patients and healthy controls (HC).
Figure 10:
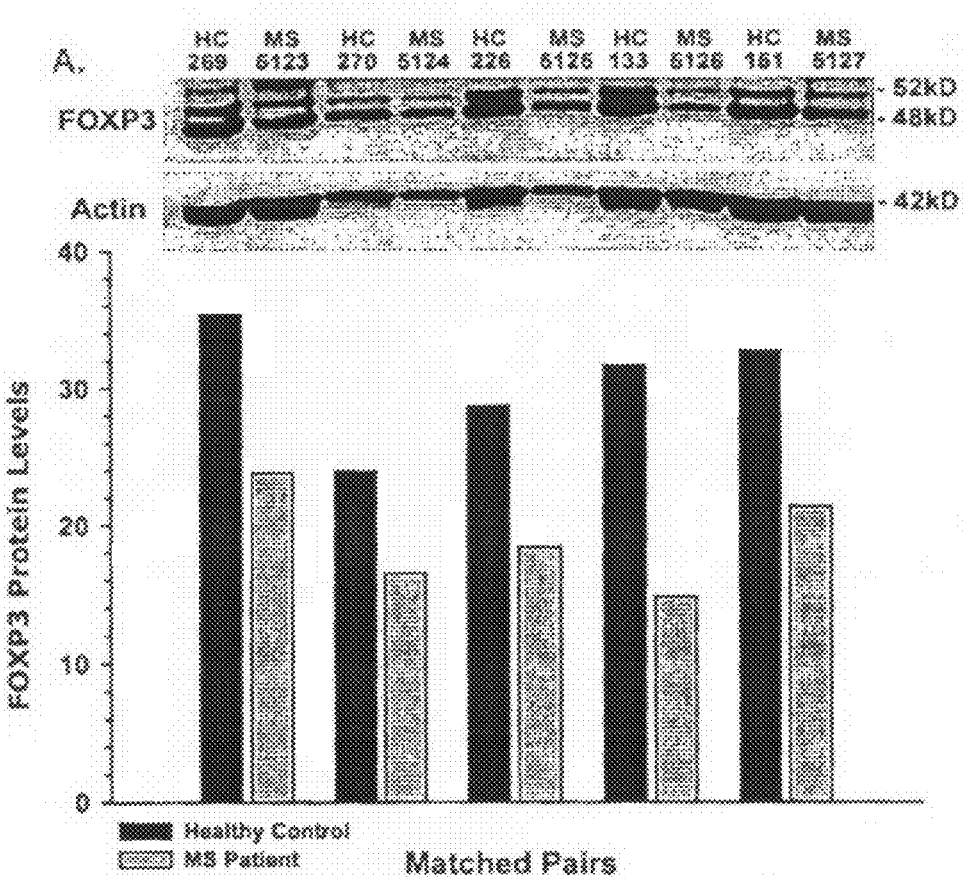
FIGS. 10A-10B shows FOXP3 protein in CD4+CD25+ T cells from MS patients and HC.
Figure 10:
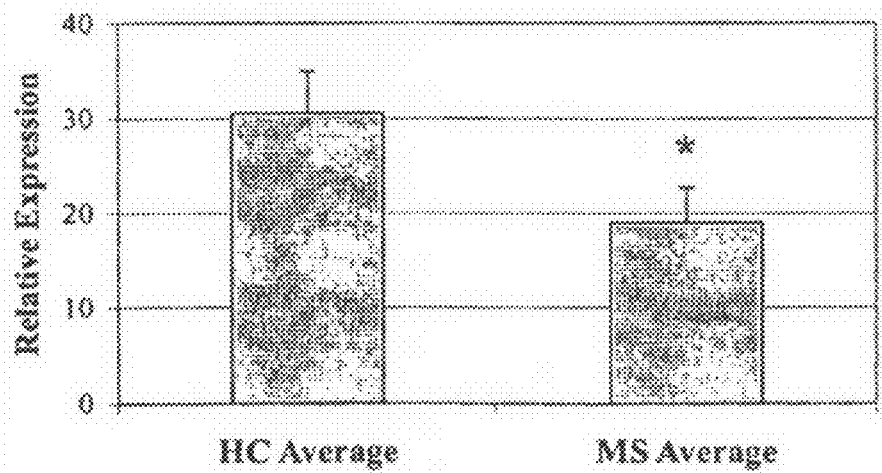

The expression of FOXP3 in the CD4+CD25+ fraction of PBMC using both mRNA and protein detection assays in 5 MS patients enrolled sequentially in an open label clinical trial versus 5 age and gender matched HC donors was determined. A comparison of FOXP3 mRNA expression by quantitative real-time PCR revealed reduced message levels in CD4+CD25+ T cells from each of the MS patients versus paired HC (FIG. 9A), and a significant difference between the two groups (p<0.0475, FIG. 9B). Similarly, comparison of FOXP3 protein expression by Western blots of CD4+CD25+ T cells isolated from the same five donor pairs demonstrated a consistent reduction in FOXP3 protein (range 31-53%, FIG. 10A) and a highly significant difference between the two groups (p<0.01, FIG. 10B).

To assess functional suppression from these 5 paired MS and HC donors, various ratios of CD4+CD25− indicator cells mixed with CD4+CD25+ T cells (1:0, 1:2, 1:1, 1:0.3, 1:0.1, and 0:1, respectively) were stimulated using super-optimal (2 ug/ml), optimal (1 and 0.5 ug/ml), as well as sub-optimal (0.1 ug/ml) concentrations of plate-bound anti-CD3 antibody plus anti-CD28 antibody. At the sub-optimal anti-CD3 concentration, CD4+CD25+ T cells from MS patients consistently produced less suppression than those from matched HC. For each concentration of anti-CD3, an $I_{50}$ value (percentage of CD4+CD25+ cells needed to cause a 50% suppression of proliferation response by the CD4+CD25− indicator cells) was calculated based on dose-dependent suppression observed at various cell ratios. Thus, higher $I_{50}$ values indicate less suppression. MS patients had higher $I_{50}$ values (less suppression) vs. matched HC at all four concentrations of anti-CD3 antibody, with the lowest concentration (0.1 ug/ml) showing the greatest difference between groups (72±13 vs. 48±6, p<0.05).

Reduced expression of FOXP3 and less suppression in MS might be explained by a decreased percentage of CD4+CD25+ T cells in PBMC. However, this was not the case, since the two groups had essentially identical levels of CD4+CD25+ T cells (4.6±1.5% for HC vs. 4.7±1.3% for MS). Because the CD4+CD25+ compartment contains a mixture of both activated effector T cells and Treg cells, it is possible that reduced Treg function might be explained by a reduced percentage of Treg cells. Activation of purified CD4+CD25+ Treg cells alone with anti-CD3 antibody typically produces lower responses than the CD4+CD25− indicator cells due to the anergic nature of the Treg suppressor cells. Moreover, the better the Treg enrichment within the CD4+CD25+ compartment, the lower the expected proliferation response. Therefore, responses of the purified CD4+CD25+ cells from MS versus HC donors without any indicator cells present (the 1:0 ratio) were compared. Purified CD4+CD25+ T cells from MS patients consistently had more proliferation than the same number of CD4+CD25+ T cells from HC donors, particularly at the 2 ug/ml anti-CD3 concentration, demonstrating reduced Treg cell activity in MS patients.

Figure 11:
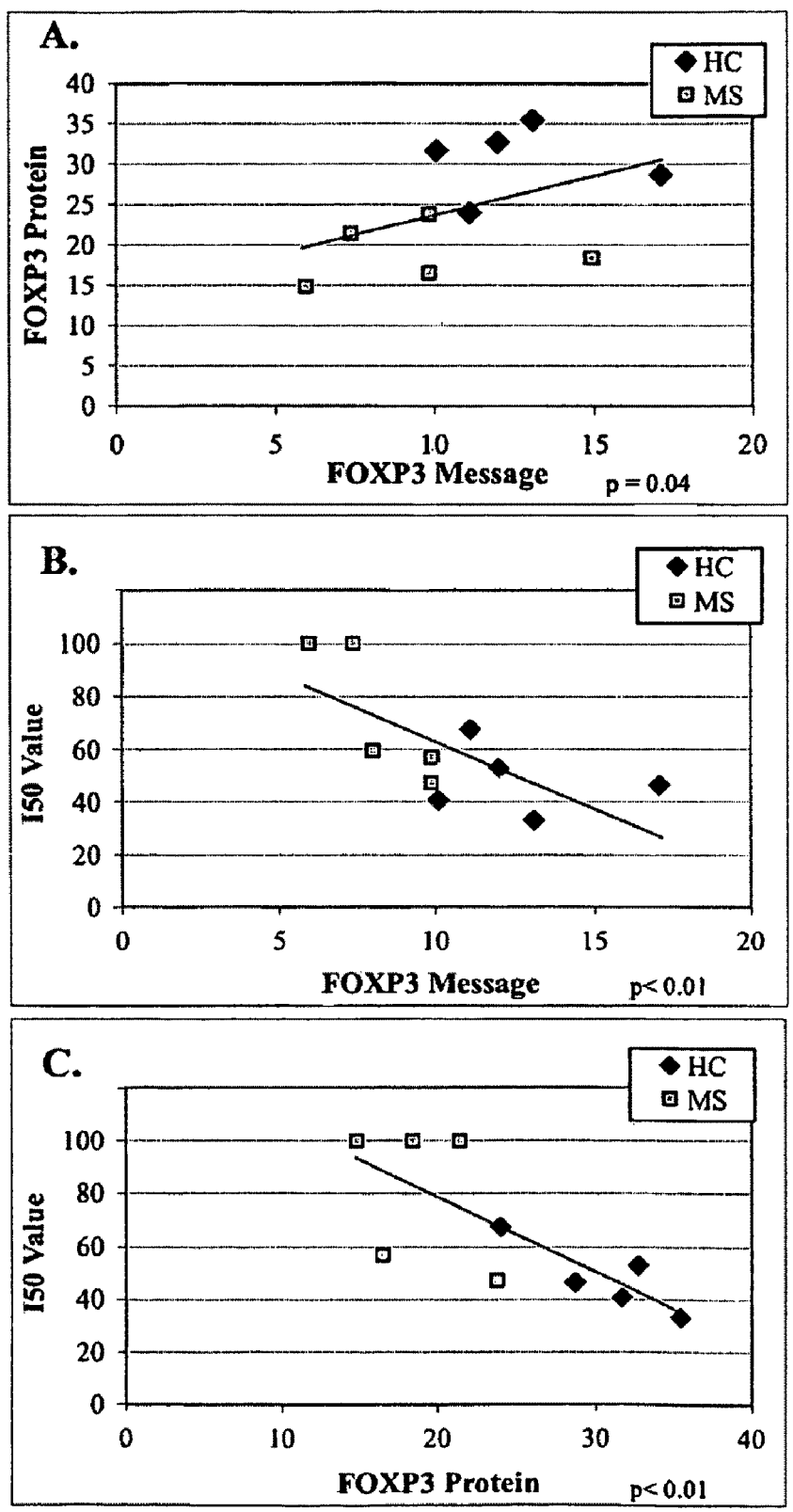
FIGS. 11A-11C are a series of graphs illustrating the correlation between FOXP3 message, FOXP3 protein, and $I_{50}$ values.

An additional question of interest is whether a correlation exists between functional suppression as determined by $I_{50}$ values and expression of FOXP3 message and FOXP3 protein. As shown in FIG. 11A, there was a significant correlation between FOXP3 message and protein levels when evaluated for all MS and HC donors (p<0.05). Moreover, there was a highly significant negative correlation between FOXP3 mRNA levels and $I_{50}$ suppression values determined at all concentrations of anti-CD3 mAb (p<0.01, FIG. 11B), and between FOXP3 protein levels and $I_{50}$ suppression values determined at the 0.1 ug/ml concentration of anti-CD3 mAb (p<0.01, FIG. 11C). These statistically significant correlations validate FOXP3 expression levels as an indicator of ex vivo suppression assessed during sub-optimal activation with anti-CD3.

Figure 12:
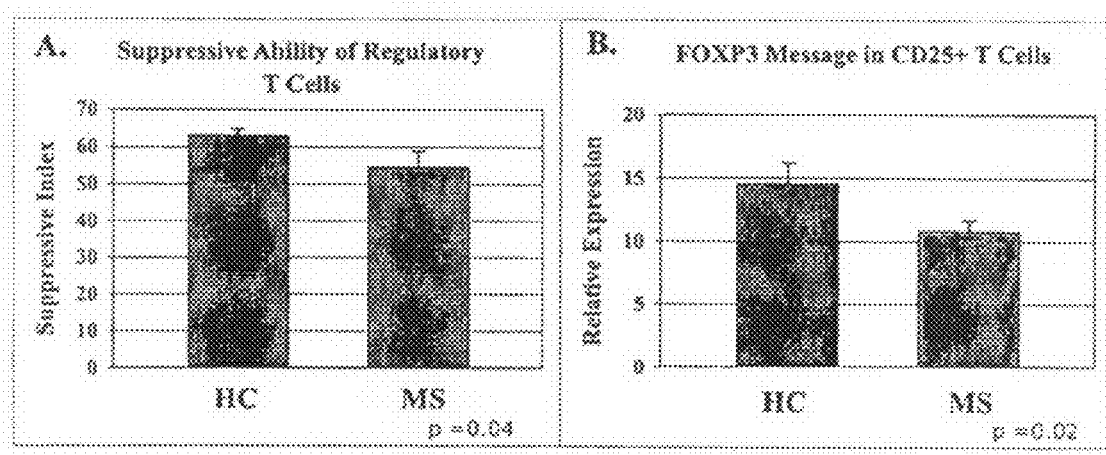
FIGS. 12A-12B are bar graphs show the suppressive regulatory ability of T cells and the FOXP3 message in T cells, respectively. A. PBMC from healthy control subjects (HC) and unvaccinated MS patients (MS) were sorted into CD4+CD25+ and CD4+CD25–fractions by magnetic beads. The CD25+ cells were tested for suppressive ability in a regulatory T cell assay, using CD25– cells as indicators. CD4+CD25– T cells were stimulated with plate-bound anti-CD3 and anti-CD28 in the presence of increasing numbers of CD4+CD25+ regulatory T cells (Tregs). The percentage of Tregs needed to reduce proliferation of the indicator cells by 50% was subtracted from 100 to give a Suppressive Index. A higher Suppressive Index indicates better suppression. There was a significant difference in the Suppressive Index between HC and MS (p=0.04, t-test). B. Another aliquot of the CD25+ cells was examined for FOXP3 expression using real-time PCR. There was a significant difference between HC and MS in FOXP3 expression (p=0.02, t-test). Error bars=SEM FIGS. 13A-13B PBMC from healthy controls (HC) and MS patients respond differentially to TCR CDR2 peptides. A. Production of IL-10 and IFN-gamma was measured in the PBMC response to TCR BV CDR2 peptides (left) and TCR AV CDR2 peptides (right) representing the entire TCR BV and AV gene repertoire as measured by ELISPOT assay. PBMC responses to ConA were equivalent in HC and MS patients (not shown). B. Summary of cytokine-producing cells in which IL-10 or IFN-gamma production was summed for responses to all BV+AV CDR2 peptides. Total cytokine production represents the summation of IL-10-+IFN-gamma-secreting cells for all peptides. *P<0.05 comparing the frequency in HC vs. MS patients. The HC group consisted of five individuals, three females and two males. The MS patient group consisted of three individuals, two females with relapsing, remitting MS, both symptomatic, and one male with secondary, progressive MS.

To further compare Treg suppression and FOXP3 expression in a larger sampling of MS patients and HC, functional suppression and mRNA expression by real-time PCR was assessed in a total of 19 MS patients enrolled in the open label study (including the 5 patients described above) versus a total of 19 HC controls (including the 5 described above). As is shown in FIG. 12 for all donors, functional suppression (expressed as the suppressive index=100 minus the $I_{50}$ value) (FIG. 12A) and FOXP3 expression (FIG. 12B) were significantly reduced in the MS patients versus HC donors (p=0.04 and 0.02, respectivley). No significant differences were found in FOXP3 expression in RRMS versus SPMS patients, although there was a trend towards lower FOXP3 levels in RRMS patients.

Example 5

Natural Recognition of TCR Determinants in Healthy Control Donors

ELISPOT Assay

To determine antigen-specific T cell frequency by ELISPOT, blood mononuclear cells were separated by Ficoll density gradient centrifugation, resuspended in 2% human AB serum, and aliquotted at 0.5 and 0.25 million cells in triplicate wells of nitrocellulose-coated microliter plates (Becton Dickinson, Franklin Lakes, N.J.) pretreated with anti-IFN-γ (Mabtech, Sweden) or anti-IL-10 (PharMingen, San Diego, Calif.) mAb. Peptides, ConA, and medium were added and the plates incubated at 37C for 24 hours (IFN-γ) or 48 hours (IL-10). Biotin-labeled secondary mAb for each cytokine was added, followed by streptavidin-alkaline phosphatase (Dako Corp., Carpinteria, Calif.) and substrate (BCIP/NBT phosphatase substrate, KPL Laboratories, Gaithersburg, Md.) to develop optimal blue staining. Cytokine spots were quantified using an AID Immunospot Analyzer (AID, Cleveland, Ohio) equipped with a high resolution lens camera and analytical software designed for use with the AID system. Mean spots/well were calculated for each Ag, and net counts established after subtraction of background (no Ag). The frequency of Ag-specific spot-forming cells per million PBMC was determined from the average net response observed at two different cell concentrations. The mean net frequency +SEM was calculated for MS patients and HC, and differences compared by Student's t test for significance (p<0.05).

Detection of Cytokine Producing Cells

PBMC were removed from plates by washing with 3× with PBS and 3× with PBS/0.05% Tween, pH 7.6. To each well was added 100 μl of either anti-IFN-γ (1 μg/ml, Mabtech, Sweden) or anti-IL-10 (2 μg/ml, PharMingen, San Diego, Calif.) and incubated for 4 hours at room temperature in the dark. Plates were washed 4× with PBS/Tween, then 100 μl per well of alkaline-phosphatase-conjugated streptavidin (DAKO) (1:1000 of stock) was added and plates were incubated for 45 minutes at room temperature. Plates were washed 4× with PBS/Tween and 6× with PBS, 1 minute each. 100 μl of BCIP/NBT substrate (KPL Laboratories, Gaithersburg, Md.) was added and the color reaction was allowed to develop for 3-7 minutes. Plates were rinsed 3× with distilled water and dried overnight at room temperature.

Analysis of ELISPOTS

Plates were scanned with an Immunospot Reader (Cellular Technology Limited, Cleveland, Ohio) with optimized lighting conditions and analyzed according to the predetermined parameters of sensitivity, spot size, and background. The background counts were subtracted, and data was then normalized to cytokine secreting cells per million PBMC plated.

T Cell Frequency

To evaluate native recognition of TCR determinants, the frequency of IL-10 and IFN-γ secreting T cells from the blood of 5 HC (3 females, 2 males, average age 28) was assessed using the ELISPOT assay, to detect responses to a comprehensive panel of 113 unique CDR2 peptides representing nearly all of the AV and BV repertoires (Table 1). Only 3 peptides, AV1 S4A1N1T, BV15S1 and BV20S1A1N1, could not be tested due to solubility and toxicity problems. Peptide-specific T cells secreting either IL-10 or IFN-γ were detected in response to nearly all of the TCR peptides tested (FIG. 13A). Frequencies varied considerably from peptide to peptide and from donor to donor, but overall, were not markedly different between males and females. The average frequency of IL-10-secreting T cells recognizing BV peptides was >600 cells/million PBMC, and for AV peptides, >300 cells/million. The most reactive IL-10-inducing BV peptide (>2000 cells/million PBMC) was BV10S1P, a pseudogene presumed not to be present as a functional TCR, whereas the most reactive AV peptide (>1000 cells/million PBMC) was a rare AV29S1A2T allele. BV10S1P induced minimal frequencies of IFN-γ secreting cells, suggesting a strongly biased Th2 response.

IFN-γ responses to TCR peptides were less vigorous than IL-10 responses, with an average frequency of 250 cells/million BV-reactive T cells and an average frequency of 182 cells/million AV-reactive T cells. The most reactive IFN-γ-inducing peptide (900 cells/million PBMC) was BV19S1P, another pseudogene. These results show reduced or absent T cell tolerance (higher responses) to self TCR sequences that are rarely expressed in vivo, but only partial tolerance (lower but clearly detectable responses) to the more abundant TCR sequences that are utilized most often by autoreactive T cells known to be present in both HC and MS donors. The responses detected in HC donors normally help to prevent autoreactive T cells from becoming pathogenic.

The total frequencies of TCR-reactive T cells, calculated by summing the individual frequencies, showed only a 2-fold range of responses among the 5 HC donors (FIG. 13B). The frequency of IL-10-secreting T cells was higher than that of IFN-γ-secreting T cells for all 5 donors, and in most cases, frequencies of BV peptides were higher than AV peptides. These data suggest that on average, as much as 8% of total circulating T cells (78,484 cells/million PBMC) were responsive to TCR CDR2 sequences. Thus, CDR2-reactive T cells represent a substantial portion of the CD4+CD25+ Treg population in healthy controls that has been estimated to be between 5 and 10% of T cells.

TABLE 1

| Name | Amino Acid Sequence | SEQ ID NO: |
|---|---|---|
| AV1S1 | YPGQHLQLLLKYFSGDPLVKG | 1 |
| AV1S2A1N1T | YPNQGLQLLLKYTSAATLVKG | 2 |
| AV1S2A4T | YPNQGLQLLLKYTTGATLVKG | 3 |
| AV1S2A5T | YPNQGLQLLLKYTSAATLVKG | 4 |
| AV1S3A1T | YPNQGLQLLLKYLSGSTLVES | 5 |

TABLE 1-continued

| Name | Amino Acid Sequence | SEQ ID NO: |
|---|---|---|
| AV1S3A2T | YPNQGLQLLLKYLSGSTLVKG | 6 |
| AV1S4A1N1T | SPGQGLQLLLKYFSGDTLVQG | 7 |
| AV1S5 | HPNKGLQLLLKYTSAATLVKG | 8 |
| AV2S1A1 | YSGKSPELIMFIYSNGDKEDG | 9 |
| AV2S1A2 | YSGKSPELIMSIYSNGDKEDG | 10 |
| AV2S2A1T | YSRKGPELLMYTYSSGNKEDG | 11 |
| AV2S2A2T | YSRIGPELLMYTYSSGNKEDG | 12 |
| AV2S3A1T | DCRKEPKLLMSVYSSGNEDGR | 13 |
| AV3S1 | NSGRGLVHLILIRSNEREKHS | 14 |
| AV4S1 | LPSQGPEYVIHGLTSNVNNRM | 15 |
| AV4S2A1T | IHSQGPQYIIHGLKNNETNEM | 16 |
| AV4S2A3T | IHSQGPQNIIHGLKNNETNEM | 17 |
| AV5S1 | DPGRGPVFLLLIRENEKEKRK | 18 |
| ADV6S1A1N1 | SSGEMIFLIYQGSYDQQNATE | 19 |
| AV6S1A2N1 | SSGEMIFLIYQGSYDEQNATE | 20 |
| AV7S1A1 | HDGGAPTFLSYNALDGLEETG | 21 |
| AV7S1A2 | HDGGAPTFLSYNGLDGLEETG | 22 |
| AV7S2 | HAGEAPTFLSYNVLDGLEEKG | 23 |
| AV8S1A1 | ELGKRPQLIIDIRSNVGEKKD | 24 |
| AV8S1A2 | ELGKGPQLIIDIRSNVGEKKD | 25 |
| AV8S2A1N1T | ESGKGPQFIIDIRSNMDKRQG | 26 |
| AV9S1 | YSRQRLQLLLRHISRESIKGF | 27 |
| AV10S1A1 | EPGEGPVLLVTVVTGGEVKKL | 28 |
| AV11S1A1T | FPGCAPRLLVKGSKPSQQGRY | 29 |
| AV12S1 | PPSGELVFLIRRNSFDEQNEI | 30 |
| AV13S1 | NPWGQLINLFYIPSGTKQNGR | 31 |
| ADV14S1 | PPSRQMILVIRQEAYKQQNAT | 32 |
| AV15S1 | EPGAGLQLLTYIFSNMDMKQD | 33 |
| AV16S1A1T | YPNRGLQFLLKYITGDNLVKG | 34 |
| ADV17S1A1T | FPGKGPALLIAIRPDVSEKKE | 35 |
| AV18S1 | ETAKTPEALFVMTLNGDEKKK | 36 |
| AV19S1 | HPGGGIVSLFMLSSGKKKHGR | 37 |
| AV20S1 | FPSQGPRFIIQGYKTKVTNEV | 38 |
| AV2S1A1N1 | YPAEGPTFLSISISSIKDKNED | 39 |
| AV22S1A1N1T | YPGEGLQLLLKATKADDKGSN | 40 |
| AV23S1 | DPGKGLTSLLLIQSSQREQTS | 41 |
| AV24S1 | DTGRGPVSLTIMTFSENTKSN | 42 |
| AV25S1 | DPGEGPVLLIALYKAGELTSN | 43 |
| AV26S1 | KYGEGLIFLMMLQKGGEEKSH | 44 |

TABLE 1-continued

| Name | Amino Acid Sequence | SEQ ID NO: |
|---|---|---|
| AV27S1 | DPGKSLESLFVLLSNGAVKQE | 45 |
| AV28S1A1T | QEKKAPTFLFMLTSSGIEKKS | 46 |
| AV29S1A1T | KHGEAPVFLMILLKGGEQMRR | 47 |
| AV29S1A2T | KHGEAPVFLMILLKGGEQKGH | 48 |
| AV30S1A1T | DPGKGPEFLFTLYSAGEEKEK | 49 |
| AV31S1 | YPSKPLQLLQRETMENSKNFG | 50 |
| AV32S1 | RPGGHPVFLIQLVKSGEVKKQ | 51 |
| BV1S1A1N1 | SLDQGLQFLIQYYNGEERAKG | 52 |
| BV1S1A2 | SLDQGLQFLIHYYNGEERAKG | 53 |
| BV2S1A1 | FPKQSLMLMATSNEGSKATYE | 54 |
| BV2S1A3N1 | FPKKSLMLMATSNEGSKATYE | 55 |
| BV2S1A4T | FPKQSLMLMATSNEGCKATYE | 56 |
| BV2S1A5T | FPKXSLMQIATSNEGSKATYE | 57 |
| BV3S1 | DPGLGLRLIYFSYDVKMKEKG | 58 |
| BV4S1A1T | QPGQSLTLIATANQGSEATYE | 59 |
| BV5S1A1T | TPGQGLQFLFEYFSETQRNKG | 60 |
| BV5S1A2T | TLGQGLQFLFEYFSETQRNKG | 61 |
| BV5S2 | ALGQGPQFIFQTYEEEERQRG* | 62 |
| BV5S3A1T | VLGQGPQFIFQYYEKEERGRG | 63 |
| BV5S4A1T | ALGLGLQLLLWYDEGEERNRG | 64 |
| BV5S4A2T | ALGLGLQFLLWYDEGEERNRG | 65 |
| BV5S6A1T | ALGQGPQFIFQYYREEENGRG | 66 |
| BV6S1A1N1 | SLGQGPEFLIYFQGTGAADDS | 67 |
| BV6S1A3T | SLGQGPELLIYFQGTGAADDS | 68 |
| BV6S2A1N1T | ALGQGPEFLTYFQNEAQLDKS | 69 |
| BV6S3A1N1 | ALGQGPEFLTYFNYEAQQDKS | 70 |
| BV6S4A1 | TLGQGPEFLTYFQNEAQLEKS | 71 |
| BV6S4A4T | NPGQGPEFLTYFQNEAQLEKS | 72 |
| BV6S5 | LGQGPEFLTYFQNEAQLEKS | 73 |
| BV6S6A1T | ALGQGPEFLTYFNYEAQPDKS | 74 |
| BV6S8A2T | TLGQGSEVLTYSQSDAQRDKS | 75 |
| BV7S1A1N1T | KAKKPPELMFVYSYEKLSINE | 76 |
| BV7S2A1N1T | SAKKPLELMFVYSLEERVENN | 77 |
| BV7S3A1T | SAKKPLELMFVYNFKEQTENN | 78 |
| BV8S1 | TMMRGLELLIYFNNNVPIDDS | 79 |
| BV8S3 | TMMQGLELLAYFRNRAPLDDS | 80 |
| BV9S1A1T | DSKKFLKIMFSYNNKELIINE | 81 |
| BV10S1P | KLEEELKFLVYFQNEELIQKA | 82 |
| BV10S2O | TLEEELKFFIYFQNEEIIQKA | 83 |

TABLE 1-continued

| Name | Amino Acid Sequence | SEQ ID NO: |
|---|---|---|
| BV11S1A1T | DPGMELHLIHYSYGVNSTEKG | 84 |
| BV12S1A1N1 | DPGHGLRLLHYSYGVKDTDKG | 85 |
| BV12S2A1T | DLGHGLRLIHYSYGVQDTNKG | 86 |
| BV12S2A2T | DLGHGLRLIHYSYGVKDTNKG | 87 |
| BV12S2A3T | DLGHGLRLIHYSYGVHDTNKG | 88 |
| BV12S3 | DLGHGLRLIYYSAAADITDKG | 89 |
| BV13S1 | GLRLIHYSVGAGITDQGEV | 90 |
| BV13S2A1T | DPGMGLRLIHYSVGEGTTAKG | 91 |
| BV13S3 | DPGMGLRLIYYSASEGTTDKG | 92 |
| BV13S4 | DPGMGLRRIHYSVAAGITDKG | 93 |
| BV13S5 | DLGLGLRLIHYSNTAGTTGKG | 94 |
| BV13S6A1N1T | DPGMGLKLIYYSVGAGITDKG | 95 |
| BV13S7 | DPGMGLRLIYYSAAAGTTDKE | 96 |
| BV14S1 | DPGLGLRQIYYSMNVEVTDKG | 97 |
| BV15S1 | DPGLGLRLIYYSFDVKDINKG | 98 |
| BV16S1A1N1 | VMGKEIKFLLHFVKESKQDES | 99 |
| BV17S1A1T | DPGQGLRLIYYSQIVNDFQKG | 100 |
| BV17S1A2T | DPGQGLRLIYYSHIVNDFQKG | 101 |
| BV18S1 | LPEEGLKFMVYLQKENIIDES | 102 |
| BV19S1P | NQNKEFMLLISFQNEQVLQET | 103 |
| BV19S2O | NQNKEFMFLISFQNEQVLQEM | 104 |
| BV20S1A1N1 | AAGRGLQLLFYSVGIGQISSE | 105 |
| BV20S1A1N3T | AAGRGLQLLFYSIGIDQISSE | 106 |
| BV21S1 | ILGQGPELLVQFQDESVVDDS | 107 |
| BV21S2A1N2T | NLGQGPELLIRYENEEAVDDS | 108 |
| BV21S3A1T | ILGQGPKLLIQFQNNGVVDDS | 109 |
| BV22S1A1T | ILGQKVEFLVSFYNNEISEKS | 110 |
| BV23S1A1T | GPGQDPQFFISFYEKMQSDKG | 111 |
| BV23S1A2T | GPGQDPQFLISFYEKMQSDKG | 112 |
| BV24S1A1T | KSSQAPKLLFHYYNKDFNNEA | 113 |
| BV24S1A2T | KSSQAPKLLFHYYDKDFNNEA | 114 |
| BV25S1A1T | VLKNEFKFLISFQNENVFDET | 115 |
| BV25S1A3T | VLKNEFKFLVSFQNENVFDET | 116 |

*Bv5S2 in the native form has a Y (in place of a T) at position 49 (which corresponds to amino acid 12 of SEQ ID NO: 62).

Example 6

Deficient TCR-Reactive T Cells in MS Patients

Figure 13:
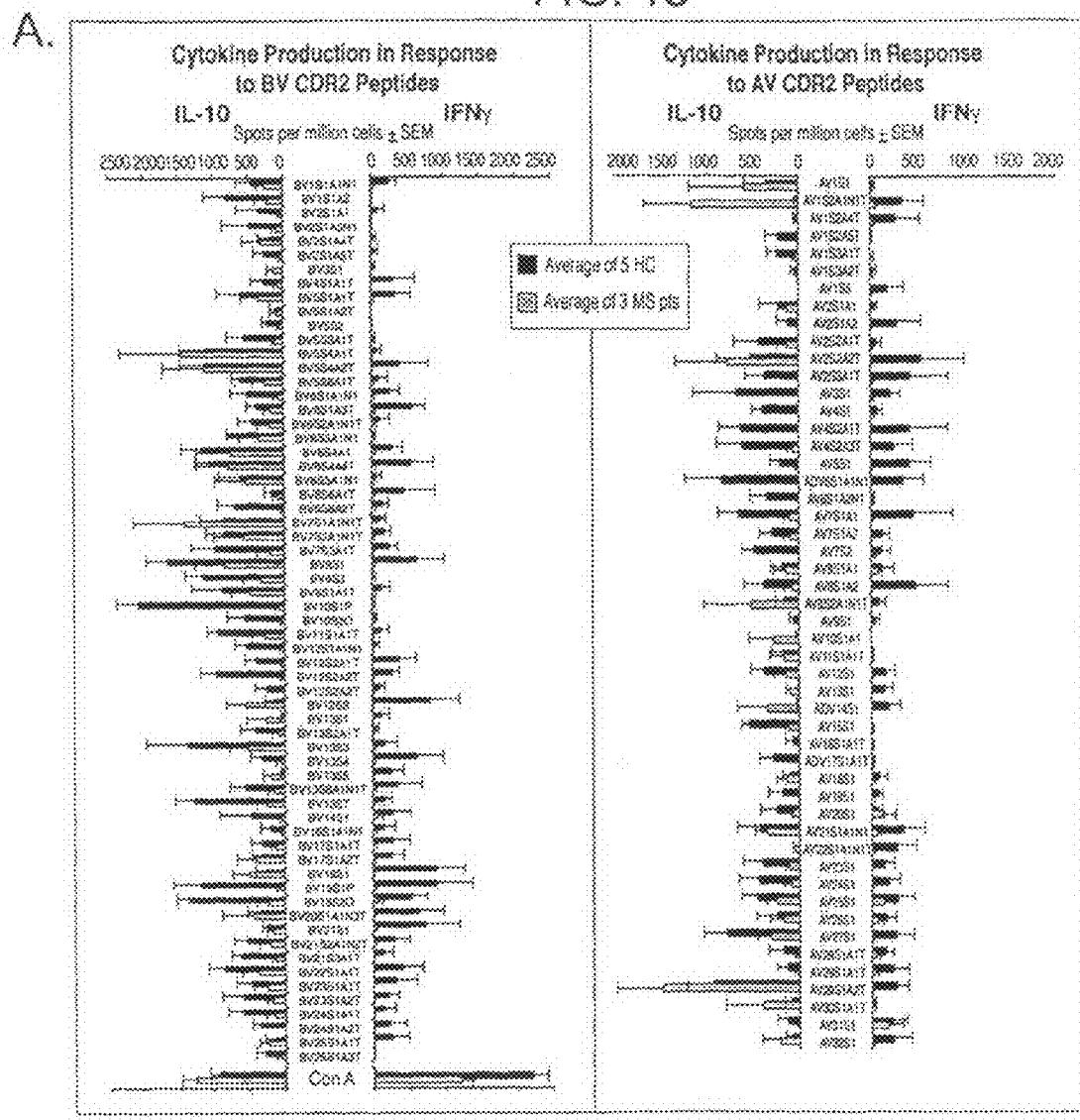
Figure 13:
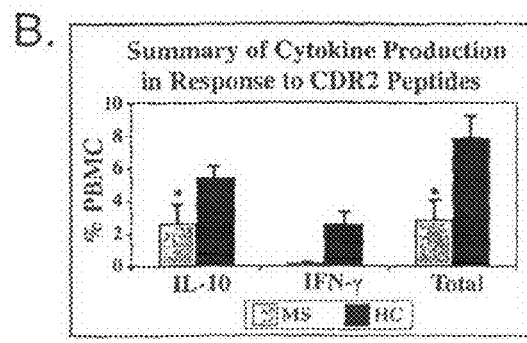

The frequencies of IL-10-secreting PBMC specific for CDR2 peptides from BV5S2, Y49TBV5S2 and BV6S1 were significantly lower in MS patients versus HC (FIG. 13A). However, there was no difference in response to ConA for either IL-10 or IFN-γ secreting cells, indicating that MS patients were not generally immunosuppressed. Moreover, there were no significant differences in frequencies related to age, gender, disability, or treatment of the donors. This analysis has been expanded to the nearly complete panel of 113 AV and BV CDR2 peptides in 3 MS patients (2 relapsing remitting-RRMS, and 1 secondary progressive-SPMS) for comparison with the 5 HC presented above. The results showed striking differences in both the magnitude and pattern of response in the MS patients versus HC. The reduction in IL-10 responses to BV5S2 and BV6S1 peptides shown previously (FIG. 13A), was again evident in the expanded analysis. Overall, the total frequency of T cells responding to the panel of CDR2 peptides was significantly reduced (p=0.03) by 65% compared to HC (27,706 cells/million=2.8% in MS versus 78,484 cells/million=7.8% in HC; FIG. 13B). This reduction was especially marked (>90%) in the frequencies of IFN-γ-secreting T cells in all three MS patients, but was also evident in IL-10-secreting T cells (>50% decrease versus HC), with a significant reduction (p=0.045) in response to BV peptides (17,845 cells/million in MS versus 38,595 cells/million in HC). Moreover, the pattern of response was different in MS patients, showing overall reduced frequencies to most peptides (FIG. 13). However, for a few peptides (e.g., AV1S2A1N1T and AV29S1A2T), as well as for the positive control, ConA, the MS patients responded as well or better than HC, demonstrating that there was not a global deficit in the ability of MS T cells to respond to activation through the TCR, as has been suggested in Type I diabetes patients.

Example 7

Identification of a Subset of Discriminatory TCR Peptides that Reflects Deficient Anti-TCR Responses in MS Patients Versus Healthy Controls To facilitate evaluations of additional MS patients and HC donors, a subset of TCR peptides was identified that optimally discerned differences in IL-10 responses between HC and MS patients. Seven BV peptides and 1 AV peptide were found that were individually recognized significantly better by all of the HC than the MS patients (designated as Pool #1). Further comparison revealed a total frequency of 8,351+1, 134 IL-10 secreting T cells/million PBMC in the 5 HC versus 1,197+838 in MS patients. This difference was highly significant (p<0.001) and discriminating (a net difference of 7154 cells/million PBMC), even though the sampling of patients was very small. However, use of the peptide subset both reflected and enhanced the ability to detect the general deficiency in TCR-reactive IL-10 secreting T cells in MS, initially detected by the complete set of CDR2 peptides (p<0.001 versus p=0.03). Using a similar approach for analyzing IFN-γ responses to TCR peptides, only 2 BV peptides (BV12S2A1T and BV12S2A2T) and one AV peptide (ADV6S1A1N1) were found that induced IFN-γ-secreting T cells in all 5 HC, but that were poorly recognized by MS patients (designated as Pool #2). The two BV12S2 alleles were also quite similar to each other, with only one difference in sequence in CDR2 (A1=Q; A2=K at position 16), but they produced distinct responses in individual donors. Although differences in recognition of each individual IFN-γ-inducing peptide were not significant in HC versus MS donors, the difference in the total frequency (994+528 in HC versus 13+21 in MS) was significant (p=0.021) and discriminating (a net difference of 981 cells/million). The identification of these discriminatory peptides streamlines efforts to identify MS patients with deficient ELISPOT responses.

Example 8

Development and Validation of Treg Activity in PBMC from Healthy Control Donors

To develop a standard procedure for assessing inhibitory activity of CD4+CD25+ Treg cells in vitro, CD4+CD25+ T cells isolated using a FACSVantage cell sorter (Becton Dickinson, Franidin Lakes, N.J.) versus magnetic beads were compared. FACS sorted cells were collected to enrich CD25 high cells versus CD25low cells, with indicator cells isolated from the CD4+CD25− population. The bead sorting method involved negative selection for CD4+ T cells from PBMC, using magnetic beads coated with antibodies to CD8+ T cells, macrophages, B cells, and NK cells, giving >90% purity of the CD4+ fraction. The CD4+ T cells were further separated into CD25+ versus CD25− T cells using anti-CD25-coated beads, and after removal of the beads, there was >90% purity of the CD25+ T cells and >98% purity of the CD25− T cells. These FACS and bead sorted. CD4+CD25+ and CD4+CD25− T cell populations were cultured alone or were mixed at varying ratios using a constant number of CD4+CD25− responder T cells. The cells were stimulated with plate-bound anti-CD3+ anti-CD28 mAbs for 6 days at an optimal stimulatory concentration (0.2 µg/ml) in the absence of additional APC, and after 6 days, were assessed for proliferation responses using 3H-Tdy uptake.

The CD4+CD25− T cells alone (1:0 ratio) proliferated well in response to stimulation with anti-CD3/CD28, although the response using the FACS sorted CD4+CD25− population gave a stronger signal than the bead-sorted CD4+CD25− population. In contrast, the FACS and bead sorted CD4+CD25+ T cells alone (0:1 ratio) had essentially no response to stimulation as expected. There was a dose-dependent inhibition of the response of CD4+CD25− indicator cells in the presence of increasing percentages of CD4+CD25+ Treg cells, with all CD4+CD25+ fractions totally inhibiting the indicator cells at the 1:2 ratio, and with partial inhibition at the 1:1 ratio. The percent CD4+CD25+ cells in the mixed culture versus the percent inhibition were plotted, and the $I_{50}$ value (percent of CD4+CD25+ Treg cells giving 50% inhibition of CD4+CD25− indicator cells) was calculated. The best inhibition was observed with the FACS-sorted CD4+CD25+ high cells ($I_{50}$=37%), with a very similar level of inhibition in the FACS-sorted CD4+CD25+ low population ($I_{50}$=38%). The bead-sorted CD4+CD25+ T cells were somewhat less inhibitory ($I_{50}$=47%), especially at the 1:1 ratio, due in part to the reduced reactivity of the CD4+CD25− indicator cells.

Two additional comparisons of FACS versus bead-sorted populations established that on average, the FACS-sorted CD4+CD25+ high cells ($I_{50}$=38%) were more potent than the FACS-sorted CD4+CD25+ low cells ($I_{50}$=58%) or the bead-sorted CD4+CD25+ cells ($I_{50}$=60%). These results indicate that Treg activity is enriched in the CD4+CD25+ high population, although substantial Treg activity can also be detected in the CD4+CD25+ low population. Comparable suppressive activity was also detected in the bead-sorted population, which includes a wider spectrum, and thus a more complete representation of Treg cells present in the CD4+CD25+ fraction of PBMC from each donor. The FACS-sorted and bead sorted CD4+CD25+ T cell populations were relatively enriched for Treg cells versus the CD4+CD25− indicator cells, as determined using RT-PCR technique to quantify the expression of FOXP3. Bead-sorted CD4+CD25+ T cells had a 2-5-fold enhancement of FOXP3 expression, whereas FACS sorted CD4+CD25+ T cells showed an 8-28-fold enhancement versus the CD4+CD25− indicator cells.

As qualitatively similar Treg activity could be detected in the more plentiful and convenient bead-sorted CD4+CD25+ T cells, this method was utilized for further experiments. However, to verify activity for selected mechanistic questions, additional comparisons were made between bead and FACS-sorted cells as needed. Further evaluation of the CD4+CD25+ T cells sorted by the bead method demonstrated that the Treg activity was cell-cell contact dependent, and could be completely reversed by addition of IL-2 or antibodies to CTLA-4, glucocorticoid induced TNF receptor (GITR), IL-10, and IL-17, but not TGF-β. These characteristics are essentially identical to Treg cells reported in mice and humans, and indicate that the bead method indeed, selects for classical Treg cells. Overall, these data support the involvement of CTLA-4, GITR, and IL-17 in the mechanism of suppression by TCR reactive Treg cells, and are compatible with the consistent production of IL-10 observed in TCR-reactive T cell populations (FIG. 13).

Example 9

Suppressive Activity in CD4+CD25+ T Cells Declines with Age and is a Fixed Trait in Each Healthy Control Donor Treg activity in 27 HC donors was evaluated to determine if there were age or gender dependent differences. Treg responses (showing percent suppression at the 1:2 ratio of indicator:suppressor cells) were vigorous in young HC donors, but suppression declined with age. Some HC donors appeared to lack detectable Treg activity altogether. Overall, there were no differences in the total number of CD4+CD25+ T cells among HC who had varying degrees of suppressive activity, indicating that Treg activity cannot be predicted by simply measuring the percentage of CD4+CD25+ T cells in blood. In contrast to the age-dependency, there was no gender effect on Treg activity, with the mean level of suppression being 33+40% in 17 females (age 33+9), versus 37+39 in 10 males (age 36+13) (p>0.5). Repeated testing of both responsive and nonresponsive HC donors verified that the initial result was reproducible in all cases, with an average of <10% SEM for repeat tests among 6 responders. This result demonstrates that the presence or absence of Treg activity is a fixed trait in each donor, although the degree of suppression may vary somewhat over time.

CD4+CD25-CD45RO+ T cells are more reactive indicator cells for the Treg assay and allow detection of Treg activity in non-suppressive HC donors. The reduced responsiveness of the CD4+CD25− indicator cell population obtained by the bead sorting method compared to the FACS sorting method, especially in older donors, suggested that there might be a mixture of more versus less responsive cells in this fraction. Thus, subfractions of the CD4+CD25− population based on the CD45RO (memory) marker were evaluated. CD4+CD25-CD45RO+ memory T cells had a much more vigorous response to stimulation with anti-CD3/CD28 than CD4+CD25-CD45RO− naive T cells. This enhanced responsiveness provided a much stronger signal in the indicator cell population than unfractionated CD4+CD25− T cells, and in addition, allowed detection of Treg responsiveness in about a third of HC donors tested that originally did not have demonstrable Treg activity using unfractionated CD4+CD25− indicator cells. In one HC donor, the less responsive CD4+CD25−

CD45RO− T cells inhibited the corresponding CD4+CD25−CD45RO+ indicator cell fraction, indicating that Treg activity could also reside in this non-activated naive T cell population. These results demonstrate that HC donors may have Treg function distributed among different CD4 subpopulations.

Example 10

TCR-Reactive T Cells Possess Treg Activity

To establish a connection between TCR-reactive T cells and Treg cells, whether TCR reactivity could be found in the CD4+CD25+ Treg cell subpopulation isolated directly from HC was first determined. Thus, CD4+CD25+ versus CD4+CD25− populations were isolated and stimulated with a pool of eight TCR CDR2 peptides that optimally distinguished differences in IL-10 responses between HC and MS patients (designated as Pool #1), or with control antigens, including Copolymer 1, a pool of neuropeptide antigens, and the recall antigen, TT. Enhanced proliferation to Pool #1 TCR peptides was observed in the CD4+CD25+, compared with the CD4+CD25− population in four of five HC donors with measurable Treg activity. These populations showed no proliferative response above background to Cop-1 or to a pool of neuroantigen peptides. In contrast, responses to TT stimulation were present mainly in the CD4+CD25− fraction. Three additional HC donors showed no Treg activity and no enhanced proliferation to Pool #1 peptides in the CD4+CD25+ fraction. One of these three HC donors demonstrated essentially equivalent levels of proliferation to Pool #1 in both the CD25+ and the CD25− fractions that might not have allowed detectable suppression of one population over the other. In the other two HC donors without Treg activity, proliferation responses to Pool #1 peptides were observed in the CD4+CD25− fraction, indicating that the TCR-reactive T cells had moved to a non-activated status. In addition, five treatment-naïve MS patients had no response to Pool #1 peptides in either the CD4+CD25+ or CD4+CD25− fractions and also had no detectable Treg activity. Six MS patients undergoing standard treatment also lacked response to Pool #1 peptides and Treg activity. These experiments demonstrate a highly significant correlation ($P=0.006$) between responsiveness to Pool #1 peptides and the presence of suppressive Treg function. Moreover, the CD4+CD25+ fraction consistently did not respond to non-TCR antigens.

Figure 14:
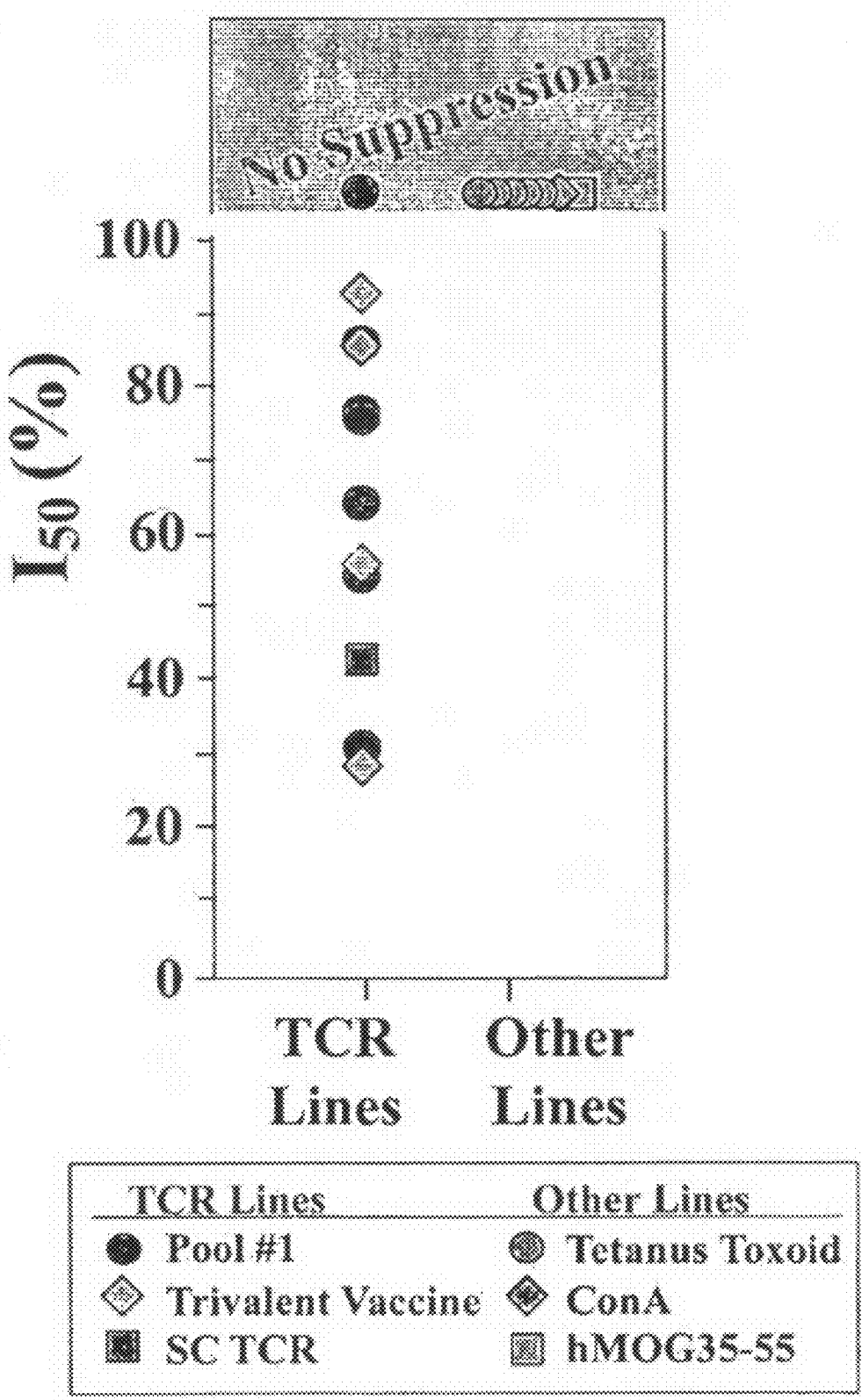
FIG. 14 is a graph illustrating that suppressive activity correlates with T cell specificity for TCR determinants. Treg activity determined by suppression assay (expressed as $I_{50}$ value) was measured for 12 T cell lines specific for TCR determinants (TCR CDR2 pool 1 peptides, trivalent CDR2 peptide vaccine, or scTCR protein) and seven T cell lines specific for non-TCR determinants (TT, ConA, human MOG-35-55 peptide). Treg activity was significantly associated with TCR reactivity (p<0.00016, Fisher's exact test).

To further test the association between TCR reactivity and Treg function, T cell lines specific for TCR determinants (Pool #1 peptides, CDR2 peptides from BV5S2, BV6S5, and BV13S1, or a soluble single chain AV23/BV6 protein) or control antigens (TT, ConA, or MOG peptide) were isolated and evaluated for suppressive activity. Similar to PBMC, the CD4+CD25+ T cells from 11 of 12 TCR-reactive T cell lines also demonstrated Treg activity when tested in combination with CD4+CD25− indicator cells, whereas 0 of 7 T cell lines specific for non-TCR antigens derived from the same fraction had detectable Treg activity. These results showing Treg function in TCR-reactive T cell lines, but not in T cell lines specific for other antigens tested are illustrated in FIG. 14. The correlation between TCR reactivity and suppressor function in T cell lines was highly significant ($P=0.00016$), directly demonstrating Treg activity in the TCR-reactive T cells. Treg activity observed in the TCR reactive T cell lines was also cell-cell contact dependent, and reversed completely by addition of IL-2 and antibodies to CTLA-4, GITR, IL-10, and IL-17, and partially with anti-TGF-β, indicating that the T line cells possessed Treg characteristics that were essentially identical to Treg cells from PBMC.

Example 11

TCR Vaccination Study

Unlike mouse models of EAE, the TCRs of pathogenic neuroantigen-reactive Th1 cells in MS patients are diverse. This general lack of a clearly focused response complicates studies of network regulation in healthy humans and in patients with autoimmune diseases. To address the V gene issue in MS, TCR expression in 150 MBP-specific T cell clones from 24 MS patients were evaluated. This evaluation revealed that several AV and BV gene families were predominant, including BV2, BV5, BV6, BV13, AV2, and AV8. From this expression pattern and from related studies in CSF, three BV genes, BV5S2 (SEQ ID NO: 62), BV6S5 (SEQ ID NO: 73) and BV13S1 (SEQ ID NO: 90), were targeted for the trivalent TCR peptide composition. However, in spite of the heightened expression of these BV genes, proliferation and cytokine responses to these peptides were relatively low or undetectable in most HC and MS patients. Limiting dilution assays demonstrated on average a frequency <1 cell/million PBMC of proliferating T cells responding to each of the three peptides in the composition. After vaccination with the trivalent TCR peptide composition, TCR-reactive T cell frequencies in MS patients increased dramatically to nearly 20 cells/million PBMC on average.

Figure 15:
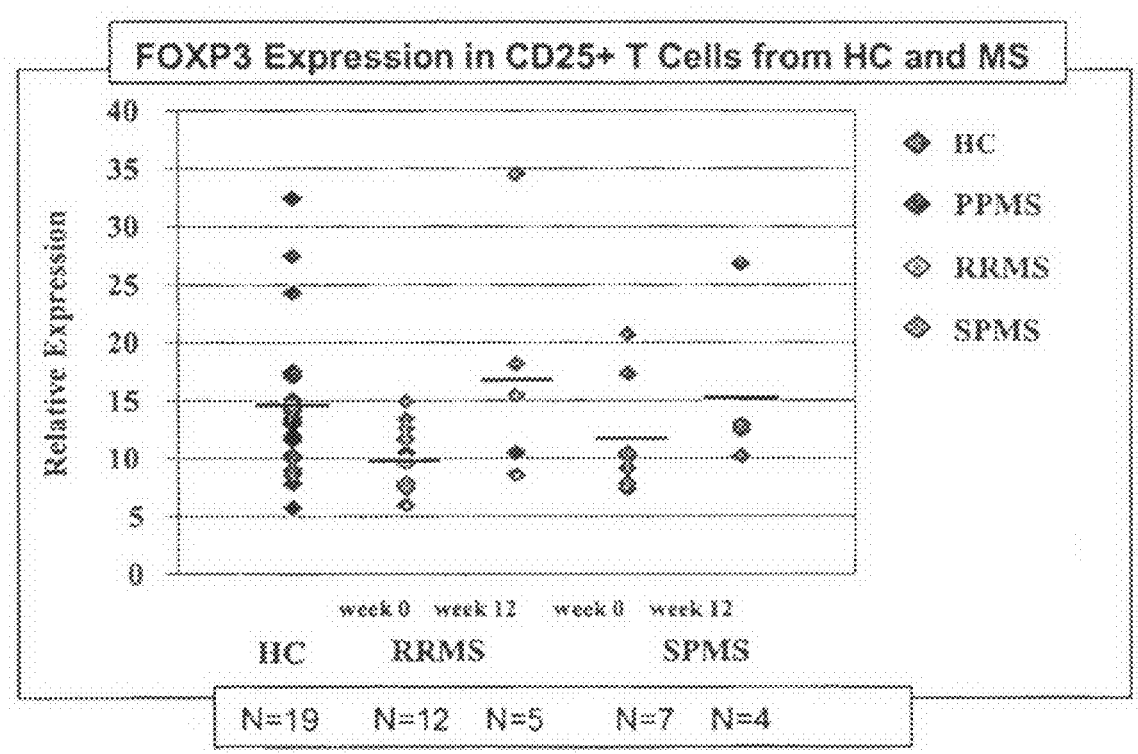
FIG. 15 is a graph showing FOXP3 expression in CD25+ T cells from healthy controls and relapsing-remitting (RR) and secondary progressive (SP) MS subjects. In both cases FOXP3 rose to control levels following vaccination with TCR peptides for 12-52 weeks.
Figure 16:
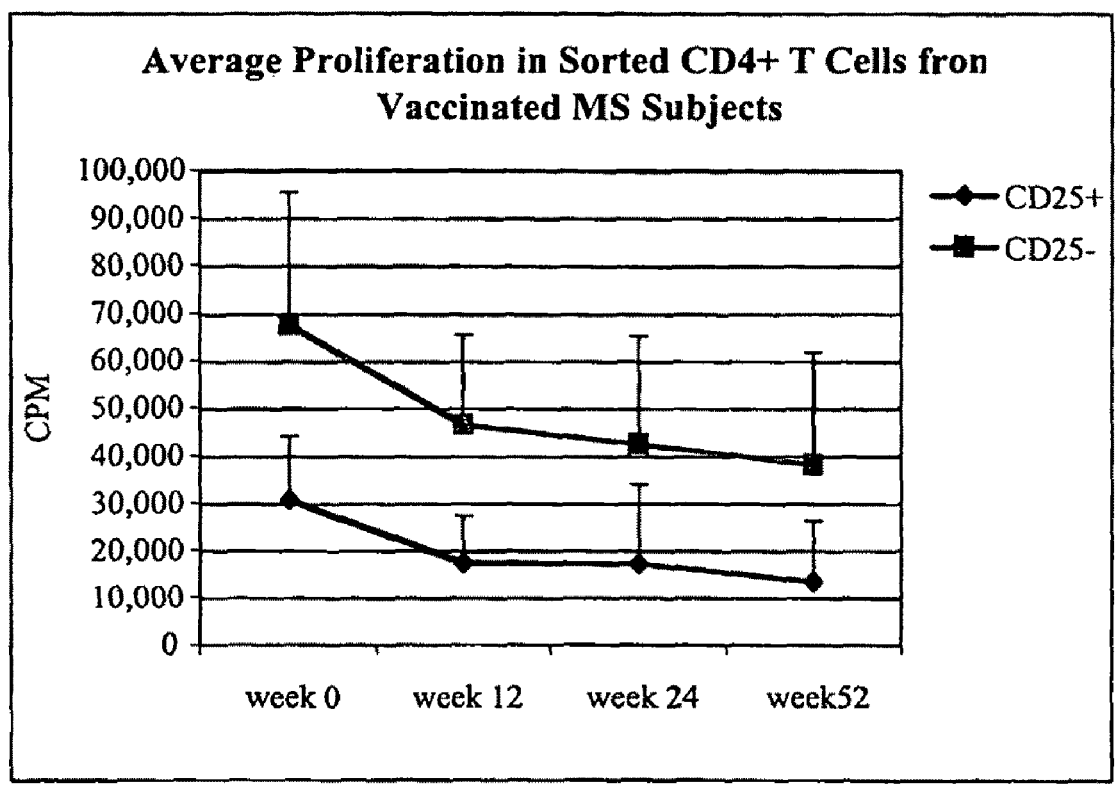
FIG. 16 is a line graph showing the average proliferation of sorted CD4+ T cells from vaccinated MS subjects. There was a significant difference in proliferation between week 0 and week 52 for the CD25+ cells (p<0.01), but not for CD25– cells (p=0.1). Five of the six individuals showed a decrease in proliferation for CD25+ and CD25–, but one subject showed an increase in the proliferation for both fractions.
Figure 17:
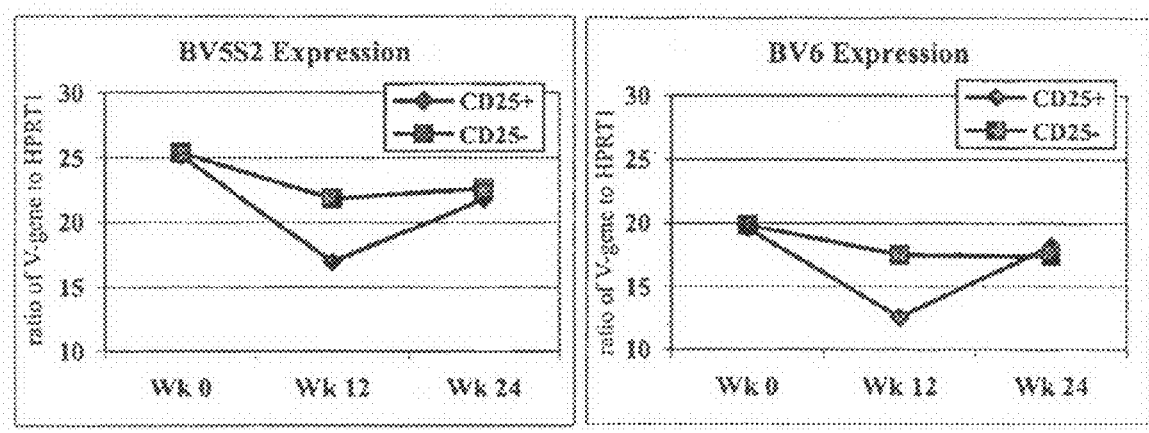
FIG. 17 is a set of line graphs showing BV5S2 expression and BV6 expression before and after vaccination with CDR2 peptides. V-gene expression levels for BV5S2 and BV6 are similar in both CD25+ and CD25– T cells before vaccination. At week +12, after receiving three injections, subject MS5113 shows a reduction in V-gene expression which is most pronounced in the CD25+ T cell fraction. By week +24, V-gene expression levels in the CD25+ fraction have rebounded to match CD25– T cells. Cells were obtained from PBMC that were then sorted by magnetic beads into CD4+CD25+ and CD4+CD25– fractions, and V-gene expression was determined by RT-PCR using a fluorescent-labeled primer. PCR products were run on a gel, and quantitated using a fluorescent scanner. V-gene expression is normalized to the endogenous control, HPRT1.

After an initial battery of clinical and immunological testing, 20 relapsing and progressive MS patients received 12 monthly intramuscular injections of 100 μg each of BV5S2 (SEQ ID NO: 62), BV6S5 (SEQ ID NO: 73) and BV13S1 (SEQ ID NO: 90) peptides emulsified in IFA. PBMC were collected from the patients at entry and over the course of the study, separated into CD4+CD25+ and CD4+CD25− fractions by magnetic beads, and evaluated for Treg cell activity by expression of Foxp3 mRNA (CD4+CD25+ cells only, FIG. 15), for changes in their ability to proliferate in response to anti-CD3/CD28 mAb (FIG. 16), and for changes in expression of targeted vs. non-targeted TCR V genes present in the TCR vaccine (FIG. 17). As is shown in FIG. 15, Foxp3 expression was decreased in both RR- and SPMS patients versus HC donors at entry, but expression of Foxp3 was restored to normal levels in both groups of patients after 12-52 weeks of monthly injections of TCR peptides. Moreover, as is shown in FIG. 16, TCR vaccination resulted in a decreased proliferation response in the CD4+CD25+ fraction, suggesting enhanced Treg function (Treg cells typically have low proliferation in response to TCR stimulation), and in the CD4+CD25− fraction, indicating a general suppressive effect on proliferation responses resulting from TCR vaccination. Additionally, as is shown in FIG. 17, BV5S2 expression and BV6 expression were evaluated before and after vaccination with CDR2 peptides. V-gene expression levels for BV5S2 and BV6 were similar in both CD25+ and CD25− T cells before vaccination. At week +12, after receiving three injections, subject MS5113 showed a reduction in V-gene expression which was most pronounced in the CD25+ T cell fraction. By week +24, V-gene expression levels in the CD25+ fraction rebounded to match CD25− T cells. A similar evaluation of non-targeted V genes (BV2 and BV3) showed much smaller changes, indicating that a more pronounced effect on TCR expression in T cells expressing TCRs corresponding to CDR2 peptides in the'vaccine vs. T cells expressing non-targeted V genes.

PBMC samples (isolated from each patient prior to vaccination (week −4) and at weeks 8, 20, and 48 after vaccination was initiated; as well as from age and gender matched healthy controls) can be evaluated for TCR tripeptide-specific CSFE proliferation, phenotyping, intracellular cytokine staining, cytokine secretion profiles, and FOXP3 mRNA/protein expression in order to characterize their heterogeneity pre- and post tripeptide administration. This information can then be correlated with results of neurological exam testing for EDSS and functional parameters that can obtained during the trial to determine if different TCR response profiles can be related to changes in clinical status.

To obtain cytokine secretion profiles, replicates of 0.5 million PBMC with and without added tripeptides (25 ug/ml of each) for 72 h were cultured. Supernatants were collected and pooled for cytokine bead array analysis of secreted IFN-γ, TNF-α, IL-4, IL-10, IL-13, and TGF-β. The pools provide sufficient supernatant for a complete cytokine analysis, and replicate measurements allow statistical comparisons of pre- versus post-vaccination levels. An analysis of cytokines from two vaccinated MS patients versus two age and gender matched HC donors demonstrated pronounced secretion of IL-10 (>4.5 nM in one of the vaccinated MS patients and >700 μM in the other), with lesser secretion of IL-4 and TNF-α. These responses were present in both unstimulated as well as TCR-peptide stimulated wells, indicating that induction of cytokines by TCR peptide vaccination had occurred systemically prior to cell culturing.

In addition, the cell pellets from the same wells can be pooled and mRNA extracted for evaluation of a wider set of cytokines, chemokines, and chemokine receptors by quantitative RT-PCR. An additional set of replicate wells containing 0.5 million PBMC stimulated with peptide versus wells without peptide can be set up and the cells labeled with CSFE dye. The cells from groups of wells can be pooled after 72 h and FACS analyzed by 4-color fluorescence to detect proliferating cells (CSFE dilution), CD4+ or CD8+ cells, and intracellular IFN-γ versus IL-4 or IL-10. To evaluate Treg cells, CD4+CD25+ T cells can be isolated from thawed PBMC and evaluated for mRNA and protein levels of FOXP3 using RT-PCR and Western blotting as described herein, as well as for FACS staining using FOXP3-specific antibodies.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. A method for assessing the efficacy of a therapy in a subject with multiple sclerosis, comprising
    determining the expression of FOXP3 in a first biological sample taken from a subject;
    determining the expression of FOXP3 in a second biological sample taken from the subject after a period of treatment with the therapy,
    wherein a difference in the expression of FOXP3 in the first biological sample as compared to the second biological sample assesses the efficacy of the therapy for treating multiple sclerosis in the subject, and wherein the first biological sample and the second biological sample comprise white blood cells,
    wherein the therapy comprises administration of a therapeutically effective amount of a TCR CDR2 peptide.

2. The method of claim 1, wherein the therapy further comprises administration of an adjuvant.

3. The method of claim 1, wherein the TCR CDR2 peptide comprises one or more amino acid sequences as set forth in SEQ ID NOs: 1-116.

4. The method of claim 1, wherein the therapy comprises a TCR CDR2 peptide comprising the amino acid sequence as set forth in or a TCR CDR2 peptide comprising the amino acid sequence set forth as SEQ ID NO: 73 or a TCR CDR2 peptide comprising the amino acid sequence set forth as SEQ ID NO: 90, or a combination thereof.

5. The method of claim 1, wherein the first biological sample and the second biological sample are isolated CD4+ CD25+ T cells.

6. The method of claim 4, wherein an increase in the expression of FOXP3 in the second biological sample as compared to the expression of FOXP3 in the first biological sample indicates that the therapy is effective.

7. The method of claim 4, wherein an decrease in the expression of FOXP3 in the second biological sample as compared to the expression of FOXP3 in the first biological sample indicates that the therapy is ineffective.

8. The method of claim 4, wherein the therapy comprises a TCR-CDR2 peptide selected from the group consisting of aTCR CDR2 polypeptide comprising the amino acid sequence as set forth in SEQ ID NO: 62, a TCR CDR2 polypeptide comprising the amino acid sequence set forth as SEQ ID NO: 73 and a TCR CDR2 polypeptide comprising the amino acid sequence set forth as SEQ ID NO: 90.

9. The method of claim 8, wherein the therapy further comprises administering a therapeutically effective amount of estrogen to the subject.

10. The method of claim 1, wherein the therapy further comprises administration of a therapeutically effective amount of estrogen to the subject.

11. The method of claim 2, wherein the adjuvant is incomplete Freud's adjuvant.

12. The method of claim 1, wherein the multiple sclerosis comprises relapsing remitting multiple sclerosis, secondary progressive multiple sclerosis or clinically isolated syndrome.

* * * * *